United States Patent [19]

Chua et al.

[11] Patent Number: 5,536,657
[45] Date of Patent: Jul. 16, 1996

[54] RECOMBINANT DNA ENCODING HUMAN RECEPTOR FOR INTERLEUKIN-12

[75] Inventors: Anne O. Chua, Wayne; Ulrich A. Gubler, Glen Ridge, both of N.J.

[73] Assignee: Hoffmann-La Roche Inc., Nutley, N.J.

[21] Appl. No.: 248,532

[22] Filed: May 31, 1994

Related U.S. Application Data

[63] Continuation-in-part of Ser. No. 094,713, Jul. 19, 1993, abandoned.

[51] Int. Cl.$^6$ .............................. C12N 5/10; C12N 15/12
[52] U.S. Cl. ................ 435/252.3; 435/69.1; 435/320.1; 435/69.52; 536/23.5
[58] Field of Search .................... 435/69.1, 69.52, 435/320.1, 240.2, 172.1, 252.3; 530/351; 536/23.5

[56] References Cited

U.S. PATENT DOCUMENTS

| | | | |
|---|---|---|---|
| 4,578,335 | 3/1986 | Urdal et al. | 435/68 |
| 4,816,565 | 3/1989 | Honjo et al. | 530/367 |
| 5,180,812 | 1/1993 | Dower et al. | 530/351 |
| 5,198,359 | 3/1993 | Taniguchi et al. | 435/252.3 |

OTHER PUBLICATIONS

Kaczmarski et al, Blood Rev. 5: 193–203 (1991).
Cosman, DNA + Prot. Eng. Tech., 2 1–3 (1990).
Harada et al PNAS 87 857–861 (1990).
Renauld et al PNAS 89 5690–94 (1992).
R. Chizzonite, et al., *J. Cell. Biol.*, 17: 73 (1993).
A. Chua, et al., *J. Immunol.*, 153: 128–136 (1994).
B. Desai, et al., *J. Immunol.*, 150: 270A (1993).
Gubler, et al., Proc. Natl. Acad. Sci. USA, 88: 4143–4147 (1991).
Stern, et al., Proc. Natl. Acad. Sci. USA, 87: 6808–6812 (1990).
Wolf, et al., J. Immunol., 146: 3074–3081 (1991).
Chan, S. H., et al., *J. Exp. Med.*, 173: 869 (1991).
Chizzonite, R., et al., *J. Immunol.*, 148: 3117 (1992).
Cosman, David, *Cytokine*, vol. 5, No. 2, pp. 95–106 (Mar., 1993).
Desai, B., et al., *J. Immunol.*, 148: 3135 (1992).
Doherty, G. M., et al. *J. Immunol.*, 149: 1666 (1992).
Fanslow, et al., *Science*, 248: 739–41 (May 11, 1990).
Gately, M., et al., *Cell Immunology*, 143: 127 (1992).
Gately, M. K., et al., *J. Immunol.*, 147: 874 (1991).
Gearing, D. P.,et al., *Cell*, 66: 9 (1991).
Hsieh, C.-S., et al., *Science*, 260: 547 (1993).
Kobayashi, M., et al., *J. Exp. Med.*, 170: 827 (1989).
Manetti, R., et al., *J. Exp. Med.*, 177: 1199 (1993).
Mizuhima, S., and S. Nagata, *Nucl. Acids. Res.*, 18: 5322 (1990).
Remington's Pharmaceutical Science, 16th Ed., Mack Eds., 1980.
Schoenhaut, D., et al., *J. Immunology*, 148: 3433 (1992).

*Primary Examiner*—John Ulm
*Attorney, Agent, or Firm*—George M. Gould; George W. Johnston; Alan P. Kass

[57] ABSTRACT

This invention relates to substantially pure Interleukin-12 receptor cDNAs and protein and uses therefore. The Interleukin-12 receptor is shown to be a member of the cytokine receptor superfamily and has a high homology to human gp130.

10 Claims, 25 Drawing Sheets

```
   1  GGTGGCTGAA CCTCGCAGGT GGCAGAGAGG CTCCCCTGGG GCTGTGGGGC
  51  TCTACGTGGA TCCGATGGAG CCGCTGGTGA CCTGGGTGGT CCCCCTCCTC
 101  TTCCTCTTCC TGCTGTCCAG GCAGGGCGCT GCCTGCAGAA CCAGTGAGTG
 151  CTGTTTTCAG GACCCGCCAT ATCCGGATGC AGACTCAGGC TCGGCCTCGG
 201  GCCCTAGGGA CCTGAGATGC TATCGGATAT CCAGTGATCG TTACGAGTGC
 251  TCCTGGCAGT ATGAGGGTCC CACAGCTGGG GTCAGCCACT TCCTGCGGTG
 301  TTGCCTTAGC TCCGGGCGCT GCTGCTACTT CGCCGCCGGC TCAGCCACCA
 351  GGCTGCAGTT CTCCGACCAG GCTGGGGTGT CTGTGCTGTA CACTGTCACA
 401  CTCTGGGTGG AATCCTGGGC CAGGAACCAG ACAGAGAAGT CTCCTGAGGT
 451  GACCCTGCAG CTCTACAACT CAGTTAAATA TGAGCCTCCT CTGGGAGACA
 501  TCAAGGTGTC CAAGTTGGCC GGGCAGCTGC GTATGGAGTG GGAGACCCCG
 551  GATAACCAGG TTGGTGCTGA GGTGCAGTTC CGGCACCGGA CACCCAGCAG
 601  CCCATGGAAG TTGGGCGACT GCGGACCTCA GGATGATGAT ACTGAGTCCT
 651  GCCTCTGCCC CCTGGAGATG AATGTGGCCC AGGAATTCCA GCTCCGACGA
 701  CGGCAGCTGG GGAGCCAAGG AAGTTCCTGG AGCAAGTGGA GCAGCCCCGT
 751  GTGCGTTCCC CCTGAAAACC CCCACAGCC TCAGGTGAGA TTCTCGGTGG
 801  AGCAGCTGGG CCAGGATGGG AGGAGGCGGC TGACCCTGAA AGAGCAGCCA
 851  ACCCAGCTGG AGCTTCCAGA AGGCTGTCAA GGGCTGGCGC CTGGCACGGA
 901  GGTCACTTAC CGACTACAGC TCCACATGCT GTCCTGCCCG TGTAAGGCCA
 951  AGGCCACCAG GACCCTGCAC CTGGGGAAGA TGCCCTATCT CTCGGGTGCT
1001  GCCTACAACG TGGCTGTCAT CTCCTCGAAC CAATTTGGTC CTGGCCTGAA
1051  CCAGACGTGG CACATTCCTG CCGACACCCA CACAGAACCA GTGGCTCTGA
1101  ATATCAGCGT CGGAACCAAC GGGACCACCA TGTATTGGCC AGCCCGGGCT
1151  CAGAGCATGA CGTATTGCAT TGAATGGCAG CCTGTGGGCC AGGACGGGGG
1201  CCTTGCCACC TGCAGCCTGA CTGCGCCGCA AGACCCGGAT CCGGCTGGAA
```

*FIG. 1A*

| | | | | |
|---|---|---|---|---|
| 1251 | TGGCAACCTA | CAGCTGGAGT | CGAGAGTCTG | GGGCAATGGG | GCAGGAAAAG |
| 1301 | TGTTACTACA | TTACCATCTT | TGCCTCTGCG | CACCCCGAGA | AGCTCACCTT |
| 1351 | GTGGTCTACG | GTCCTGTCCA | CCTACCACTT | TGGGGGCAAT | GCCTCAGCAG |
| 1401 | CTGGGACACC | GCACCACGTC | TCGGTGAAGA | ATCATAGCTT | GGACTCTGTG |
| 1451 | TCTGTGGACT | GGGCACCATC | CCTGCTGAGC | ACCTGTCCCG | GCGTCCTAAA |
| 1501 | GGAGTATGTT | GTCCGCTGCC | GAGATGAAGA | CAGCAAACAG | GTGTCAGAGC |
| 1551 | ATCCCGTGCA | GCCCACAGAG | ACCCAAGTTA | CCCTCAGTGG | CCTGCGGGCT |
| 1601 | GGTGTAGCCT | ACACGGTGCA | GGTGCGAGCA | GACACAGCGT | GGCTGAGGGG |
| 1651 | TGTCTGGAGC | CAGCCCCAGC | GCTTCAGCAT | CGAAGTGCAG | GTTTCTGATT |
| 1701 | GGCTCATCTT | CTTCGCCTCC | CTGGGGAGCT | TCCTGAGCAT | CCTTCTCGTG |
| 1751 | GGCGTCCTTG | CTACCTTGG | CCTGAACAGG | GCCGCACGGC | ACCTGTGCCC |
| 1801 | GCCGCTGCCC | ACACCCTGTG | CCAGCTCCGC | CATTGAGTTC | CCTGGAGGGA |
| 1851 | AGGAGACTTG | GCAGTGGATC | AACCCAGTGG | ACTTCCAGGA | AGAGGCATCC |
| 1901 | CTGCAGGAGG | CCCTGGTGGT | AGAGATGTCC | TGGGACAAAG | GCGAGAGGAC |
| 1951 | TGAGCCTCTC | GAGAAGACAG | AGCTACCTGA | GGGTGCCCCT | GAGCTGGCCC |
| 2001 | TGGATACAGA | GTTGTCCTTG | GAGGATGGAG | ACAGGTGCAA | GGCCAAGATG |
| 2051 | <u>TGA</u>TCGTTGA | GGCTCAGAGA | GGGTGAGTGA | CTCGCCCGAG | GCTACGTAGC |

FIG. 1B

```
  1  MEPLVTWVVP LLFLFLLSRQ GAACRTSECC FQDPPYPDAD SGSASGPRDL
 51  RCYRISSDRY ECSWQYEGPT AGVSHFLRCC LSSGRCCYFA AGSATRLQFS
101  DQAGVSVLYT VTLWVESWAR NQTEKSPEVT LQLYNSVKYE PPLGDIKVSK
151  LAGQLRMEWE TPDNQVGAEV QFRHRTPSSP WKLGDCGPQD DDTESCLCPL
201  EMNVAQEFQL RRRQLGSQGS SWSKWSSPVC VPPENPPQPQ VRFSVEQLGQ
251  DGRRRLTLKE QPTQLELPEG CQGLAPGTEV TYRLQLHMLS CPCKAKATRT
301  LHLGKMPYLS GAAYNVAVIS SNQFGPGLNQ TWHIPADTHT EPVALNISVG
351  TNGTTMYWPA RAQSMTYCIE WQPVGQDGGL ATCSLTAPQD PDPAGMATYS
401  WSRESGAMGQ EKCYYITIFA SAHPEKLTLW STVLSTYHFG GNASAAGTPH
451  HVSVKNHSLD SVSVDWAPSL LSTCPGVLKE YVVRCRDEDS KQVSEHPVQP
501  TETQVTLSGL RAGVAYTVQV RADTAWLRGV WSQPQRFSIE VQVSDWLIFF
551  ASLGSFLSIL LVGVLGYLGL NRAARHLCPP LPTPCASSAI EFPGGKETWQ
601  WINPVDFQEE ASLQEALVVE MSWDKGERTE PLEKTELPEG APELALDTEL
651  SLEDGDRCKA KM
```

FIG. 2

```
IL-12R    GSASGPRDLR  CY.RISSDRY  ECSWQYEGPT  AGVSHF.LRC  CLSSGRCCYF
GP130     LPPEKPKNLS  CIVN.EGKKM  RCEWDGGRET  HLETNFTLKS  ..EWA.....
G-CSF-R   YPPAIPHNLS  CLMNLTTSSL  ICQWEPGPET  HLPTSFTLKS  FKSRGNCQTQ
LIF-R     YPPDTPQQLN  CETH.DLKEI  ICSWNPGRVT  ALVGPRA.TS  YTLVESFSGK
CONS      -pP---P--L- C---------  -C-W--g--T  -l---f-l-s  ----------

AAG.SATRLQ  FSDQAGVSVL  YTVTLW..VE  SW...ARNQT  EK..SPEVTL
          THKFADCKAK  RDTPTSCTVD  YSTVYFVNIE  VW.VEAENAL  GKVTSDHINF
          GDSILDCVPK  DGQSHCCIPR  KHLLLYQNMG  IW.VQAENAL  GTSMSPQLCL
          YVRLK..RAE  APTNESYQLL  FQMLPNQEIY  NFTLNAHNPL  GRSQSTIL.V
          ----------  ------c---  y-------i-  -w---A-N-l  g---S----l

QLYNSVKYEP  PL.....GDI  KVSK.LAGQL  RMEWETPDN.  ..QVGAEVQF
          DPVYKVKPNP  P..HNL..SV  INSEELSSIL  KLTWTNPSIK  SV.IILKYNI
          DPMDVVKLEP  PMLRTMDPSP  EAAPPQAGCL  QLCW.EPWQP  GLHINQKCEL
          NITEKVYPHT  P......TSF  KVKDINSTAV  KLSWHLP.GN  FAKINFLCEI
          -----VK--P  P-------s-  ----------l -l-W--P---  ---i---c--

RHRTPSSPWK  LGDCGPQDDD  TESCLCPL.E  MNVAQEFQLR  RRQLGSQGSS
          QYRT.KDAST  WSQIPPEDTA  STRSSFTVQD  LKPFTEYVFR  IRCMKEDGKG
          RHKPQRGEAS  WALVGPLPLE  ALQ..YELCG  LLPATAYTLQ  IRCIRWPLPG
          EIKKSNSVQE  QRNVTIKGVE  NSSYLVALDK  LNPYTLYTFR  IRCSTETFWK
          ----------  ---v-p---e  -------l--  l-p-t-y--r  iRc-------

.WSKWSSPVC  .VPPENPP..  QPQVRFSVEQ  LGQDGRRRLT  LKEQPTQLEL
          YWSDWSEEAS  GITYEDRPSK  APSFWYKIDP  SHTQGYRTVQ  LVWKTLPPFE
          HWSDWSPSLE  LRTTERAPTV  RLDTWWR..Q  RQLDP.RTVQ  LFWKPVPLEE
          .WSKWSNKKQ  HLTTEASPSK  GPDTWR...E  WSSDG.KNLI  IYWKPLPINE
          -WS-WS----  --t-E--P--  -p--w-----  ---dg-r---  L-wkp-p--e PEGCQGLAPG  TEVTYRLQLH  MLSCPCKAKA  TRTLHLGKMP  YLSGAAYNVA
          ANGKILDYEV  TLTRWKSHLQ  NYTV.NATKL  ..TVNLTNDR  YLATLTVRNL
          DSGRIQGYVV  SWRPSGQAGA  ILPLCNTTEL  SCTFHLPSEA  QEVALVAYNS
          ANGKILSYNV  S.CSSDEETQ  SLSEIPDPQH  KAEIRLDKND  YIISVVAKNS
          --G-i--y-v  ----------  -l--------  --t--L----  y-------n-

VISSNQFGPG  LNQTWHIPAD  THTEPVALNI  SVGTNGTTMY  WPARAQSM.T
          VGKSDAAVLT  IPACDFQATH  PVMDLKAF..  PKD.NMLWVE  WTTPRESVKK
          AGTSRPTPVV  FSESRGPA..  .LTRLHAM..  ARDPHSLWVG  WEPPNPWPQG
          VGSSPPSKIA  SMEIPNDDL.  KIEQVVGM..  GKG...ILLT  WHYDPNMTCD
          vg-s------  ----------  ------am--  ----------  W---------
```

*FIG. 3A*

```
YCIEWQPVGQ  DGGLATCSLT  APQDPDPAGM  ATYSWSRESG  AMGQEKCYYI
YILEW...CV  LSDKAP.CIT  DWQQEDGTVH  RTY....LRG  NLAESKCYLI
YVIEW...GL  GPPSASNSNK  TWRMEQNGRA  TGFL...LKE  NIRPFQLYEI
YVIKW...CN  SSRSEP.CLM  DWRKVPSNST  ETVI...ESD  EFRPGIRYNF
YVIEW-----  ----a-----  -w--------  -ty-------  -------Y-f

TIFASAHPEK  LTLWSTVLST  YHFGGNASAA  GTPHHVSVKN  HSLDS..VSV
TVTPVYADGP  GSPESIKAYL  KQAPPSKGPT  VRTKKVGKNE  AVLEWDQLPV
IVTPLYQDTM  GPSQHVYAYS  QEMAPSHAPE  LHLKHIGKTW  AQLEWVPEPP
FLYGCRNQGY  QLLRSMIGYI  EELAPIVAPN  FTVEDTSADS  ILVKWEDIPV
-v--------  ----s---y-  ----p---p-  -----v----  --lew---pV DWAPSLLSTC  .....PGVLK  EYVVRCRDED  SKQVSEHPV.  QPTETQVTLS
DVQNGFIRNY  TIFYRTIIGN  ETAVNV....  ..........  DSSHTEYTLS
ELGKSPLTHY  TIFWTNAQNQ  SFSAIL....  ..........  NASSRGFVLH
EELRGFLRGY  LFYFGKGERD  TSKMRVLESG  RSDIKVKNIT  DISQKTLRIA
-----fl--y  --f-------  ----------  ----------  --s-----1-

GLRAGVAYTV  QVRADTAWLR  GVWSQPQRFS  IEVQVSDWLI  FFA..SLGSF
SLTSDTLYMV  RMAAYTDEGG  KDGPEFTFTT  PKFAQGEIEA  IVVPVCLAFL
GLEPASLYHI  HLMAASQAGA  TNSTVLTLMT  LTPEGSELHI  ILGLFGLLLL
DLQGKTSYHL  VLRAYTDGGV  GPEKSMYVVT  KENSVGLIIA  ILIPVAVAVI
-L-----Y-v  -l-A-t--g-  ---------t  ------e---  il----l--l

LSILLVGVLG  YLGLNRAARH  LCPPLPTPCA  SSAIEFPGGK  ETWQWINPVD
LTTLLGVLFC  FNKRDLIKKH  IWPNVPDPSK  SHIAQWSPHT  PPRHNFNSKD
LTCLCGTAW.  LCCSPNRKNP  LWPSVPDPAH  SSLGSWVPTI  MEEDAFQLPG
VGVVTSI.LC  YRKREWIKET  FYPDIPNPEN  CKALQF.QKS  VCEGSSALKT
l--l----l-  y------k--  lwP-vP-P--  s---------  ----------

FQEEASLQEA  LVVEMSWDKG  ERTEPLEKTE  LPEGAPELAL  DTELSLEDGD
QMYSDGNFTD  VSVVEIEAND  KKPFP.EDLK  SLDLFKKEKI  NTEGHSSGIG
..LGTPPITK  LTV..LEEDE  KKPVPWESHN  SSETCGLP..  ..........
LEMNPCTPNN  VEVLETRSAF  PKIEDTEIIS  PVAERPEDRS  DAEPENHVVV
----------  --V-------  -k--p-E---  --e-------  --e-------

RCKAKM....  .
GSSCMSSSRP  S
..........  .
SYC.......  .
----------  -
```

*FIG. 3B*

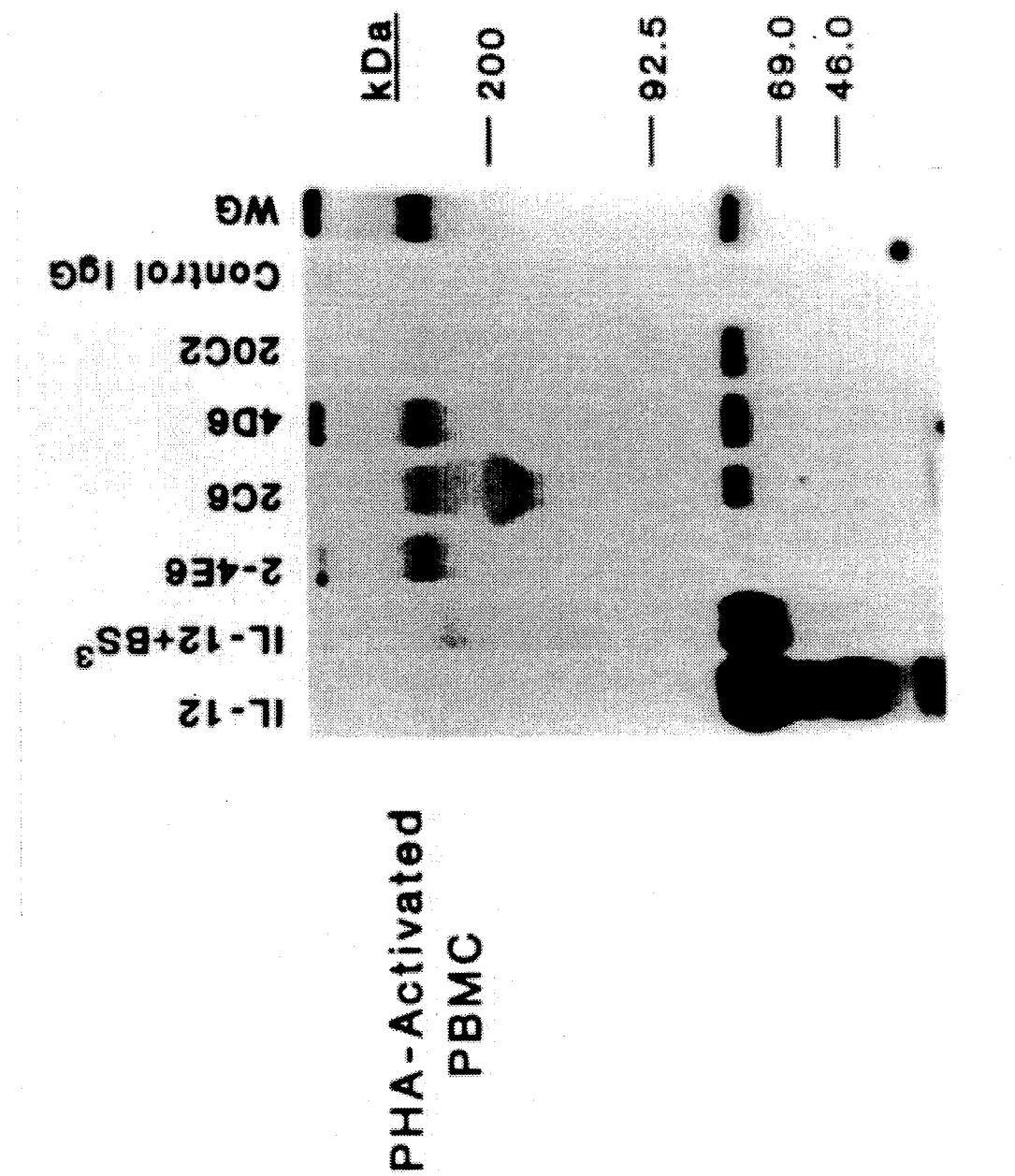

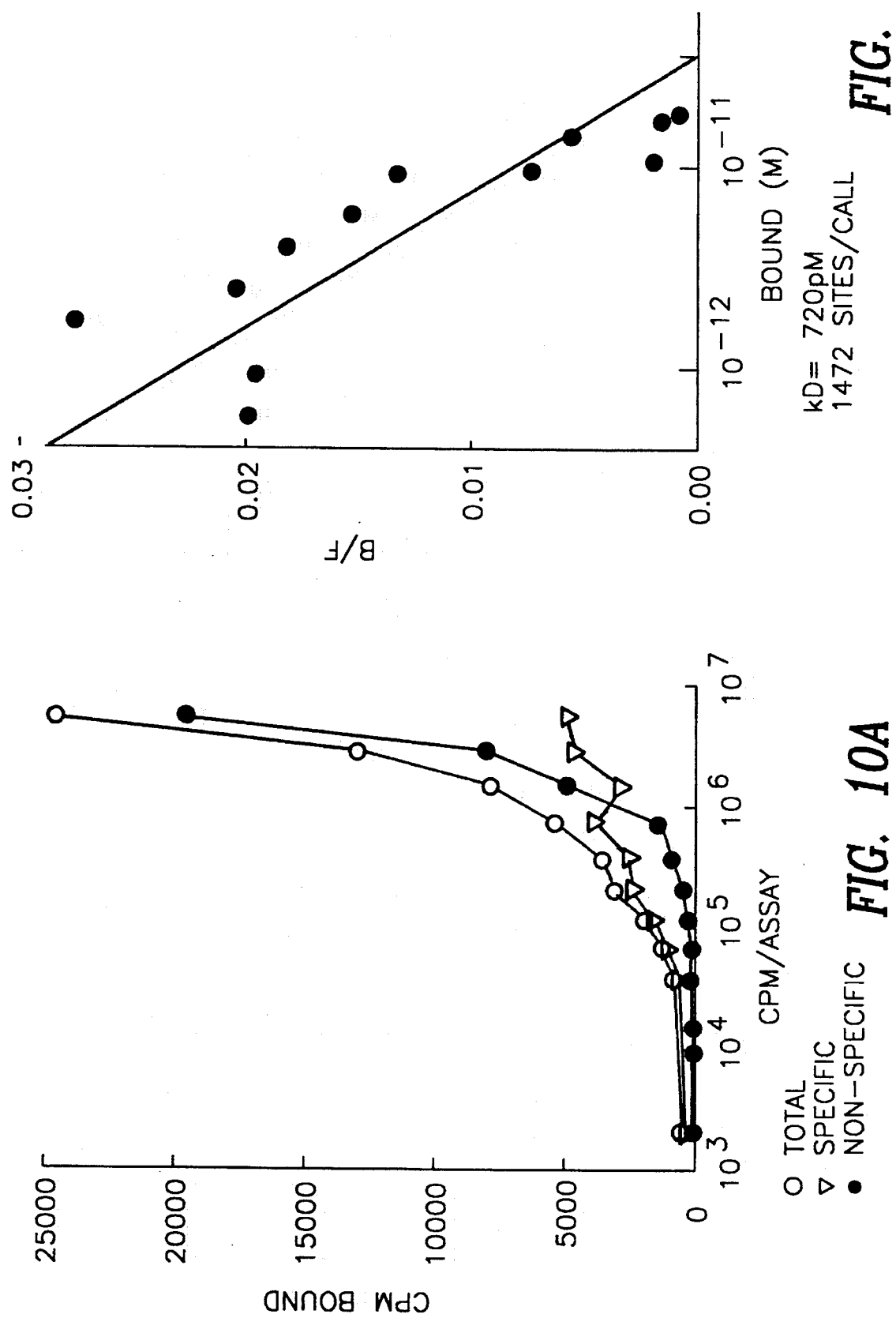

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2104 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Homo sapiens
        ( G ) CELL TYPE: human T-cells ( v i i ) IMMEDIATE SOURCE:
        ( A ) LIBRARY: library 3 day PHA/pEF- BOS
        ( B ) CLONE: human interleukin-12 receptor clone #5

( i x ) FEATURE:
        ( A ) NAME/KEY: CDS
        ( B ) LOCATION: 65..2050

( x i ) SEQUENCE DESCRIPTION: SEQ ID NO:1:

```
GGTGGCTGAA  CCTCGCAGGT  GGCAGAGAGG  CTCCCCTGGG  GCTGTGGGGC  TCTACGTGGA             60

TCCG ATG GAG CCG CTG GTG ACC TGG GTG GTC CCC CTC CTC TTC CTC TTC                 109
     Met Glu Pro Leu Val Thr Trp Val Val Pro Leu Leu Phe Leu Phe
     1             5                  10                  15

CTG CTG TCC AGG CAG GGC GCT GCC TGC AGA ACC AGT GAG TGC TGT TTT                  157
Leu Leu Ser Arg Gln Gly Ala Ala Cys Arg Thr Ser Glu Cys Cys Phe
                20              25                  30

CAG GAC CCG CCA TAT CCG GAT GCA GAC TCA GGC TCG GCC TCG GGC CCT                  205
Gln Asp Pro Pro Tyr Pro Asp Ala Asp Ser Gly Ser Ala Ser Gly Pro
             35                  40                  45

AGG GAC CTG AGA TGC TAT CGG ATA TCC AGT GAT CGT TAC GAG TGC TCC                  253
Arg Asp Leu Arg Cys Tyr Arg Ile Ser Ser Asp Arg Tyr Glu Cys Ser
         50                  55                  60

TGG CAG TAT GAG GGT CCC ACA GCT GGG GTC AGC CAC TTC CTG CGG TGT                  301
Trp Gln Tyr Glu Gly Pro Thr Ala Gly Val Ser His Phe Leu Arg Cys
     65                  70                  75

TGC CTT AGC TCC GGG CGC TGC TGC TAC TTC GCC GCC GGC TCA GCC ACC                  349
Cys Leu Ser Ser Gly Arg Cys Cys Tyr Phe Ala Ala Gly Ser Ala Thr
 80                  85                  90                  95

AGG CTG CAG TTC TCC GAC CAG GCT GGG GTG TCT GTG CTG TAC ACT GTC                  397
Arg Leu Gln Phe Ser Asp Gln Ala Gly Val Ser Val Leu Tyr Thr Val
                 100                 105                 110

ACA CTC TGG GTG GAA TCC TGG GCC AGG AAC CAG ACA GAG AAG TCT CCT                  445
Thr Leu Trp Val Glu Ser Trp Ala Arg Asn Gln Thr Glu Lys Ser Pro
             115                 120                 125

GAG GTG ACC CTG CAG CTC TAC AAC TCA GTT AAA TAT GAG CCT CCT CTG                  493
Glu Val Thr Leu Gln Leu Tyr Asn Ser Val Lys Tyr Glu Pro Pro Leu
         130                 135                 140

GGA GAC ATC AAG GTG TCC AAG TTG GCC GGG CAG CTG CGT ATG GAG TGG                  541
Gly Asp Ile Lys Val Ser Lys Leu Ala Gly Gln Leu Arg Met Glu Trp
     145                 150                 155
```

| | | | | | | | | | | | | | | | | |
|---|---|---|---|---|---|---|---|---|---|---|---|---|---|---|---|---|
|GAG|ACC|CCG|GAT|AAC|CAG|GTT|GGT|GCT|GAG|GTG|CAG|TTC|CGG|CAC|CGG|589|
|Glu|Thr|Pro|Asp|Asn|Gln|Val|Gly|Ala|Glu|Val|Gln|Phe|Arg|His|Arg| |
|160| | | | |165| | | |170| | | | |175| | |

|ACA|CCC|AGC|AGC|CCA|TGG|AAG|TTG|GGC|GAC|TGC|GGA|CCT|CAG|GAT|GAT|637|
|---|---|---|---|---|---|---|---|---|---|---|---|---|---|---|---|---|
|Thr|Pro|Ser|Ser|Pro|Trp|Lys|Leu|Gly|Asp|Cys|Gly|Pro|Gln|Asp|Asp| |
| | | | |180| | | |185| | | | |190| | | |

|GAT|ACT|GAG|TCC|TGC|CTC|TGC|CCC|CTG|GAG|ATG|AAT|GTG|GCC|CAG|GAA|685|
|---|---|---|---|---|---|---|---|---|---|---|---|---|---|---|---|---|
|Asp|Thr|Glu|Ser|Cys|Leu|Cys|Pro|Leu|Glu|Met|Asn|Val|Ala|Gln|Glu| |
| | | |195| | | | |200| | | |205| | | | |

|TTC|CAG|CTC|CGA|CGA|CGG|CAG|CTG|GGG|AGC|CAA|GGA|AGT|TCC|TGG|AGC|733|
|---|---|---|---|---|---|---|---|---|---|---|---|---|---|---|---|---|
|Phe|Gln|Leu|Arg|Arg|Arg|Gln|Leu|Gly|Ser|Gln|Gly|Ser|Ser|Trp|Ser| |
| | | |210| | | |215| | | |220| | | | | |

|AAG|TGG|AGC|AGC|CCC|GTG|TGC|GTT|CCC|CCT|GAA|AAC|CCC|CCA|CAG|CCT|781|
|---|---|---|---|---|---|---|---|---|---|---|---|---|---|---|---|---|
|Lys|Trp|Ser|Ser|Pro|Val|Cys|Val|Pro|Pro|Glu|Asn|Pro|Pro|Gln|Pro| |
| |225| | | |230| | | |235| | | | | | | |

|CAG|GTG|AGA|TTC|TCG|GTG|GAG|CAG|CTG|GGC|CAG|GAT|GGG|AGG|AGG|CGG|829|
|---|---|---|---|---|---|---|---|---|---|---|---|---|---|---|---|---|
|Gln|Val|Arg|Phe|Ser|Val|Glu|Gln|Leu|Gly|Gln|Asp|Gly|Arg|Arg|Arg| |
|240| | | |245| | | |250| | | | |255| | | |

|CTG|ACC|CTG|AAA|GAG|CAG|CCA|ACC|CAG|CTG|GAG|CTT|CCA|GAA|GGC|TGT|877|
|---|---|---|---|---|---|---|---|---|---|---|---|---|---|---|---|---|
|Leu|Thr|Leu|Lys|Glu|Gln|Pro|Thr|Gln|Leu|Glu|Leu|Pro|Glu|Gly|Cys| |
| | | | |260| | | |265| | | |270| | | | |

|CAA|GGG|CTG|GCG|CCT|GGC|ACG|GAG|GTC|ACT|TAC|CGA|CTA|CAG|CTC|CAC|925|
|---|---|---|---|---|---|---|---|---|---|---|---|---|---|---|---|---|
|Gln|Gly|Leu|Ala|Pro|Gly|Thr|Glu|Val|Thr|Tyr|Arg|Leu|Gln|Leu|His| |
| | | |275| | | |280| | | |285| | | | | |

|ATG|CTG|TCC|TGC|CCG|TGT|AAG|GCC|AAG|GCC|ACC|AGG|ACC|CTG|CAC|CTG|973|
|---|---|---|---|---|---|---|---|---|---|---|---|---|---|---|---|---|
|Met|Leu|Ser|Cys|Pro|Cys|Lys|Ala|Lys|Ala|Thr|Arg|Thr|Leu|His|Leu| |
| |290| | | |295| | | |300| | | | | | | |

|GGG|AAG|ATG|CCC|TAT|CTC|TCG|GGT|GCT|GCC|TAC|AAC|GTG|GCT|GTC|ATC|1021|
|---|---|---|---|---|---|---|---|---|---|---|---|---|---|---|---|---|
|Gly|Lys|Met|Pro|Tyr|Leu|Ser|Gly|Ala|Ala|Tyr|Asn|Val|Ala|Val|Ile| |
|305| | | |310| | | |315| | | | | | | | |

|TCC|TCG|AAC|CAA|TTT|GGT|CCT|GGC|CTG|AAC|CAG|ACG|TGG|CAC|ATT|CCT|1069|
|---|---|---|---|---|---|---|---|---|---|---|---|---|---|---|---|---|
|Ser|Ser|Asn|Gln|Phe|Gly|Pro|Gly|Leu|Asn|Gln|Thr|Trp|His|Ile|Pro| |
|320| | | |325| | | |330| | | | |335| | | |

|GCC|GAC|ACC|CAC|ACA|GAA|CCA|GTG|GCT|CTG|AAT|ATC|AGC|GTC|GGA|ACC|1117|
|---|---|---|---|---|---|---|---|---|---|---|---|---|---|---|---|---|
|Ala|Asp|Thr|His|Thr|Glu|Pro|Val|Ala|Leu|Asn|Ile|Ser|Val|Gly|Thr| |
| | | |340| | | |345| | | |350| | | | | |

|AAC|GGG|ACC|ACC|ATG|TAT|TGG|CCA|GCC|CGG|GCT|CAG|AGC|ATG|ACG|TAT|1165|
|---|---|---|---|---|---|---|---|---|---|---|---|---|---|---|---|---|
|Asn|Gly|Thr|Thr|Met|Tyr|Trp|Pro|Ala|Arg|Ala|Gln|Ser|Met|Thr|Tyr| |
| | |355| | | |360| | | |365| | | | | | |

|TGC|ATT|GAA|TGG|CAG|CCT|GTG|GGC|CAG|GAC|GGG|GGC|CTT|GCC|ACC|TGC|1213|
|---|---|---|---|---|---|---|---|---|---|---|---|---|---|---|---|---|
|Cys|Ile|Glu|Trp|Gln|Pro|Val|Gly|Gln|Asp|Gly|Gly|Leu|Ala|Thr|Cys| |
| |370| | | |375| | | |380| | | | | | | |

|AGC|CTG|ACT|GCG|CCG|CAA|GAC|CCG|GAT|CCG|GCT|GGA|ATG|GCA|ACC|TAC|1261|
|---|---|---|---|---|---|---|---|---|---|---|---|---|---|---|---|---|
|Ser|Leu|Thr|Ala|Pro|Gln|Asp|Pro|Asp|Pro|Ala|Gly|Met|Ala|Thr|Tyr| |
| |385| | | |390| | | |395| | | | | | | |

|AGC|TGG|AGT|CGA|GAG|TCT|GGG|GCA|ATG|GGG|CAG|GAA|AAG|TGT|TAC|TAC|1309|
|---|---|---|---|---|---|---|---|---|---|---|---|---|---|---|---|---|
|Ser|Trp|Ser|Arg|Glu|Ser|Gly|Ala|Met|Gly|Gln|Glu|Lys|Cys|Tyr|Tyr| |
|400| | | |405| | | |410| | | | |415| | | |

|ATT|ACC|ATC|TTT|GCC|TCT|GCG|CAC|CCC|GAG|AAG|CTC|ACC|TTG|TGG|TCT|1357|
|---|---|---|---|---|---|---|---|---|---|---|---|---|---|---|---|---|
|Ile|Thr|Ile|Phe|Ala|Ser|Ala|His|Pro|Glu|Lys|Leu|Thr|Leu|Trp|Ser| |
| | | |420| | | |425| | | |430| | | | | |

|ACG|GTC|CTG|TCC|ACC|TAC|CAC|TTT|GGG|GGC|AAT|GCC|TCA|GCA|GCT|GGG|1405|
|---|---|---|---|---|---|---|---|---|---|---|---|---|---|---|---|---|
|Thr|Val|Leu|Ser|Thr|Tyr|His|Phe|Gly|Gly|Asn|Ala|Ser|Ala|Ala|Gly| |
| | |435| | | |440| | | |445| | | | | | |

|ACA|CCG|CAC|CAC|GTC|TCG|GTG|AAG|AAT|CAT|AGC|TTG|GAC|TCT|GTG|TCT|1453|
|---|---|---|---|---|---|---|---|---|---|---|---|---|---|---|---|---|
|Thr|Pro|His|His|Val|Ser|Val|Lys|Asn|His|Ser|Leu|Asp|Ser|Val|Ser| |
| | |450| | | |455| | | |460| | | | | | |

|GTG|GAC|TGG|GCA|CCA|TCC|CTG|CTG|AGC|ACC|TGT|CCC|GGC|GTC|CTA|AAG|1501|
|---|---|---|---|---|---|---|---|---|---|---|---|---|---|---|---|---|
|Val|Asp|Trp|Ala|Pro|Ser|Leu|Leu|Ser|Thr|Cys|Pro|Gly|Val|Leu|Lys| |
|465| | | |470| | | |475| | | | | | | | |

| | | | | | | | | | | | | | | | | |
|---|---|---|---|---|---|---|---|---|---|---|---|---|---|---|---|---|
| GAG | TAT | GTT | GTC | CGC | TGC | CGA | GAT | GAA | GAC | AGC | AAA | CAG | GTG | TCA | GAG | 1549 |
| Glu | Tyr | Val | Val | Arg | Cys | Arg | Asp | Glu | Asp | Ser | Lys | Gln | Val | Ser | Glu | |
| 480 | | | | 485 | | | | | 490 | | | | | | 495 | |
| CAT | CCC | GTG | CAG | CCC | ACA | GAG | ACC | CAA | GTT | ACC | CTC | AGT | GGC | CTG | CGG | 1597 |
| His | Pro | Val | Gln | Pro | Thr | Glu | Thr | Gln | Val | Thr | Leu | Ser | Gly | Leu | Arg | |
| | | | 500 | | | | | 505 | | | | | 510 | | | |
| GCT | GGT | GTA | GCC | TAC | ACG | GTG | CAG | GTG | CGA | GCA | GAC | ACA | GCG | TGG | CTG | 1645 |
| Ala | Gly | Val | Ala | Tyr | Thr | Val | Gln | Val | Arg | Ala | Asp | Thr | Ala | Trp | Leu | |
| | | | 515 | | | | 520 | | | | | 525 | | | | |
| AGG | GGT | GTC | TGG | AGC | CAG | CCC | CAG | CGC | TTC | AGC | ATC | GAA | GTG | CAG | GTT | 1693 |
| Arg | Gly | Val | Trp | Ser | Gln | Pro | Gln | Arg | Phe | Ser | Ile | Glu | Val | Gln | Val | |
| | | 530 | | | | | 535 | | | | | 540 | | | | |
| TCT | GAT | TGG | CTC | ATC | TTC | TTC | GCC | TCC | CTG | GGG | AGC | TTC | CTG | AGC | ATC | 1741 |
| Ser | Asp | Trp | Leu | Ile | Phe | Phe | Ala | Ser | Leu | Gly | Ser | Phe | Leu | Ser | Ile | |
| | 545 | | | | | 550 | | | | | 555 | | | | | |
| CTT | CTC | GTG | GGC | GTC | CTT | GGC | TAC | CTT | GGC | CTG | AAC | AGG | GCC | GCA | CGG | 1789 |
| Leu | Leu | Val | Gly | Val | Leu | Gly | Tyr | Leu | Gly | Leu | Asn | Arg | Ala | Ala | Arg | |
| 560 | | | | | 565 | | | | | 570 | | | | | 575 | |
| CAC | CTG | TGC | CCG | CCG | CTG | CCC | ACA | CCC | TGT | GCC | AGC | TCC | GCC | ATT | GAG | 1837 |
| His | Leu | Cys | Pro | Pro | Leu | Pro | Thr | Pro | Cys | Ala | Ser | Ser | Ala | Ile | Glu | |
| | | | | 580 | | | | | 585 | | | | | 590 | | |
| TTC | CCT | GGA | GGG | AAG | GAG | ACT | TGG | CAG | TGG | ATC | AAC | CCA | GTG | GAC | TTC | 1885 |
| Phe | Pro | Gly | Gly | Lys | Glu | Thr | Trp | Gln | Trp | Ile | Asn | Pro | Val | Asp | Phe | |
| | | | 595 | | | | | 600 | | | | | 605 | | | |
| CAG | GAA | GAG | GCA | TCC | CTG | CAG | GAG | GCC | CTG | GTG | GTA | GAG | ATG | TCC | TGG | 1933 |
| Gln | Glu | Glu | Ala | Ser | Leu | Gln | Glu | Ala | Leu | Val | Val | Glu | Met | Ser | Trp | |
| | | 610 | | | | | 615 | | | | | 620 | | | | |
| GAC | AAA | GGC | GAG | AGG | ACT | GAG | CCT | CTC | GAG | AAG | ACA | GAG | CTA | CCT | GAG | 1981 |
| Asp | Lys | Gly | Glu | Arg | Thr | Glu | Pro | Leu | Glu | Lys | Thr | Glu | Leu | Pro | Glu | |
| | 625 | | | | | 630 | | | | | 635 | | | | | |
| GGT | GCC | CCT | GAG | CTG | GCC | CTG | GAT | ACA | GAG | TTG | TCC | TTG | GAG | GAT | GGA | 2029 |
| Gly | Ala | Pro | Glu | Leu | Ala | Leu | Asp | Thr | Glu | Leu | Ser | Leu | Glu | Asp | Gly | |
| 640 | | | | | 645 | | | | | 650 | | | | | 655 | |
| GAC | AGG | TGC | AAG | GCC | AAG | ATG | TGATCGTTGA | GGCTCAGAGA | GGGTGAGTGA | | | | | | | 2080 |
| Asp | Arg | Cys | Lys | Ala | Lys | Met | | | | | | | | | | |
| | | | | 660 | | | | | | | | | | | | |

CTCGCCCGAG GCTACGTAGC CTTT       2104

( 2 ) INFORMATION FOR SEQ ID NO:2:

( i ) SEQUENCE CHARACTERISTICS:
        ( A ) LENGTH: 662 amino acids
        ( B ) TYPE: amino acid
        ( D ) TOPOLOGY: linear ( i i ) MOLECULE TYPE: protein ( i x ) FEATURE:
        ( A ) NAME/KEY: Region
        ( B ) LOCATION: 1..23
        ( D ) OTHER INFORMATION: /note="N-terminal signal peptide
            ( 1 . . 2 0 or 2 3 or 2 4 )"

( i x ) FEATURE:
        ( A ) NAME/KEY: Region
        ( B ) LOCATION: 541..570
        ( D ) OTHER INFORMATION: /note="transmembrane region"

( i x ) FEATURE:
        ( A ) NAME/KEY: Region
        ( B ) LOCATION: 571..662
        ( D ) OTHER INFORMATION: /note="cytoplasmic tail region"

( i x ) FEATURE:
        ( A ) NAME/KEY: Region
        ( B ) LOCATION: 577..584
        ( D ) OTHER INFORMATION: /note="conserved area of cytoplasmic ( i x ) FEATURE:
 ( A ) NAME/KEY: Region
 ( B ) LOCATION: 618..629
 ( D ) OTHER INFORMATION: /note="conserved area of cytoplasmic tail region"

( i x ) FEATURE:
 ( A ) NAME/KEY: Region
 ( B ) LOCATION: 52..64
 ( D ) OTHER INFORMATION: /note="sequence motif of cytokine receptor superfamily Cys52..Cys62SW"

( i x ) FEATURE:
 ( A ) NAME/KEY: Region
 ( B ) LOCATION: 222..226
 ( D ) OTHER INFORMATION: /note="cytokine receptor superfamily motif (W222SKWS)"

( i x ) FEATURE:
 ( A ) NAME/KEY: Region
 ( B ) LOCATION: 121..123
 ( D ) OTHER INFORMATION: /note="N-linked glycosylation site"

( i x ) FEATURE:
 ( A ) NAME/KEY: Region
 ( B ) LOCATION: 329..331
 ( D ) OTHER INFORMATION: /note="N-linked glycosylation site"

( i x ) FEATURE:
 ( A ) NAME/KEY: Region
 ( B ) LOCATION: 346..348
 ( D ) OTHER INFORMATION: /note="N-linked glycosylation site"

( i x ) FEATURE:
 ( A ) NAME/KEY: Region
 ( B ) LOCATION: 352..354
 ( D ) OTHER INFORMATION: /note="N-linked glycosylation site"

( i x ) FEATURE:
 ( A ) NAME/KEY: Region
 ( B ) LOCATION: 442..444
 ( D ) OTHER INFORMATION: /note="N-linked glycosylation site"

( i x ) FEATURE:
 ( A ) NAME/KEY: Region
 ( B ) LOCATION: 456..458
 ( D ) OTHER INFORMATION: /note="N-linked glycosylation site"

( i x ) FEATURE:
 ( A ) NAME/KEY: Region
 ( B ) LOCATION: 24..540
 ( D ) OTHER INFORMATION: /note="Extracellular region"

( x i ) SEQUENCE DESCRIPTION: SEQ ID NO:2:

```
Met Glu Pro Leu Val Thr Trp Val Val Pro Leu Leu Phe Leu Phe Leu
 1               5                  10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
            85                  90                  95
```

| | | | | | | | | | | | | | | |
|---|---|---|---|---|---|---|---|---|---|---|---|---|---|---|
| Leu | Gln | Phe | Ser | Asp | Gln | Ala | Gly | Val | Ser | Val | Leu | Tyr | Thr | Val | Thr |
| | | | 100 | | | | | 105 | | | | 110 | | |
| Leu | Trp | Val | Glu | Ser | Trp | Ala | Arg | Asn | Gln | Thr | Glu | Lys | Ser | Pro | Glu |
| | | 115 | | | | | 120 | | | | | 125 | | | |
| Val | Thr | Leu | Gln | Leu | Tyr | Asn | Ser | Val | Lys | Tyr | Glu | Pro | Pro | Leu | Gly |
| | 130 | | | | | 135 | | | | | 140 | | | | |
| Asp | Ile | Lys | Val | Ser | Lys | Leu | Ala | Gly | Gln | Leu | Arg | Met | Glu | Trp | Glu |
| 145 | | | | | 150 | | | | | 155 | | | | | 160 |
| Thr | Pro | Asp | Asn | Gln | Val | Gly | Ala | Glu | Val | Gln | Phe | Arg | His | Arg | Thr |
| | | | | 165 | | | | | 170 | | | | | 175 | |
| Pro | Ser | Ser | Pro | Trp | Lys | Leu | Gly | Asp | Cys | Gly | Pro | Gln | Asp | Asp | Asp |
| | | | 180 | | | | | 185 | | | | | 190 | | |
| Thr | Glu | Ser | Cys | Leu | Cys | Pro | Leu | Glu | Met | Asn | Val | Ala | Gln | Glu | Phe |
| | | 195 | | | | | 200 | | | | | 205 | | | |
| Gln | Leu | Arg | Arg | Arg | Gln | Leu | Gly | Ser | Gln | Gly | Ser | Ser | Trp | Ser | Lys |
| | 210 | | | | | 215 | | | | | 220 | | | | |
| Trp | Ser | Ser | Pro | Val | Cys | Val | Pro | Pro | Glu | Asn | Pro | Pro | Gln | Pro | Gln |
| 225 | | | | | 230 | | | | | 235 | | | | | 240 |
| Val | Arg | Phe | Ser | Val | Glu | Gln | Leu | Gly | Gln | Asp | Gly | Arg | Arg | Arg | Leu |
| | | | | 245 | | | | | 250 | | | | | 255 | |
| Thr | Leu | Lys | Glu | Gln | Pro | Thr | Gln | Leu | Glu | Leu | Pro | Glu | Gly | Cys | Gln |
| | | | | 260 | | | | | 265 | | | | 270 | | |
| Gly | Leu | Ala | Pro | Gly | Thr | Glu | Val | Thr | Tyr | Arg | Leu | Gln | Leu | His | Met |
| | | | 275 | | | | | 280 | | | | | 285 | | |
| Leu | Ser | Cys | Pro | Cys | Lys | Ala | Lys | Ala | Thr | Arg | Thr | Leu | His | Leu | Gly |
| | | 290 | | | | | 295 | | | | | 300 | | | |
| Lys | Met | Pro | Tyr | Leu | Ser | Gly | Ala | Ala | Tyr | Asn | Val | Ala | Val | Ile | Ser |
| 305 | | | | | 310 | | | | | 315 | | | | | 320 |
| Ser | Asn | Gln | Phe | Gly | Pro | Gly | Leu | Asn | Gln | Thr | Trp | His | Ile | Pro | Ala |
| | | | | 325 | | | | | 330 | | | | | 335 | |
| Asp | Thr | His | Thr | Glu | Pro | Val | Ala | Leu | Asn | Ile | Ser | Val | Gly | Thr | Asn |
| | | | 340 | | | | | 345 | | | | | 350 | | |
| Gly | Thr | Thr | Met | Tyr | Trp | Pro | Ala | Arg | Ala | Gln | Ser | Met | Thr | Tyr | Cys |
| | | 355 | | | | | 360 | | | | | 365 | | | |
| Ile | Glu | Trp | Gln | Pro | Val | Gly | Gln | Asp | Gly | Gly | Leu | Ala | Thr | Cys | Ser |
| | 370 | | | | | 375 | | | | | 380 | | | | |
| Leu | Thr | Ala | Pro | Gln | Asp | Pro | Asp | Pro | Ala | Gly | Met | Ala | Thr | Tyr | Ser |
| 385 | | | | | 390 | | | | | 395 | | | | | 400 |
| Trp | Ser | Arg | Glu | Ser | Gly | Ala | Met | Gly | Gln | Glu | Lys | Cys | Tyr | Tyr | Ile |
| | | | | 405 | | | | | 410 | | | | | 415 | |
| Thr | Ile | Phe | Ala | Ser | Ala | His | Pro | Glu | Lys | Leu | Thr | Leu | Trp | Ser | Thr |
| | | | 420 | | | | | 425 | | | | | 430 | | |
| Val | Leu | Ser | Thr | Tyr | His | Phe | Gly | Gly | Asn | Ala | Ser | Ala | Ala | Gly | Thr |
| | | 435 | | | | | 440 | | | | | 445 | | | |
| Pro | His | His | Val | Ser | Val | Lys | Asn | His | Ser | Leu | Asp | Ser | Val | Ser | Val |
| | 450 | | | | | 455 | | | | | 460 | | | | |
| Asp | Trp | Ala | Pro | Ser | Leu | Leu | Ser | Thr | Cys | Pro | Gly | Val | Leu | Lys | Glu |
| 465 | | | | | 470 | | | | | 475 | | | | | 480 |
| Tyr | Val | Val | Arg | Cys | Arg | Asp | Glu | Asp | Ser | Lys | Gln | Val | Ser | Glu | His |
| | | | | 485 | | | | | 490 | | | | | 495 | |
| Pro | Val | Gln | Pro | Thr | Glu | Thr | Gln | Val | Thr | Leu | Ser | Gly | Leu | Arg | Ala |
| | | | 500 | | | | | 505 | | | | | 510 | | |
| Gly | Val | Ala | Tyr | Thr | Val | Gln | Val | Arg | Ala | Asp | Thr | Ala | Trp | Leu | Arg |

|       |       |       |       | 515   |       |       |       |       | 520   |       |       |       |       | 525   |       |       |       |
|-------|-------|-------|-------|-------|-------|-------|-------|-------|-------|-------|-------|-------|-------|-------|-------|-------|-------|
| Gly   | Val   | Trp   | Ser   | Gln   | Pro   | Gln   | Arg   | Phe   | Ser   | Ile   | Glu   | Val   | Gln   | Val   | Ser   |       |       |
|       | 530   |       |       |       |       | 535   |       |       |       |       | 540   |       |       |       |       |       |       |
| Asp   | Trp   | Leu   | Ile   | Phe   | Phe   | Ala   | Ser   | Leu   | Gly   | Ser   | Phe   | Leu   | Ser   | Ile   | Leu   |       |       |
| 545   |       |       |       |       | 550   |       |       |       |       | 555   |       |       |       |       | 560   |       |       |
| Leu   | Val   | Gly   | Val   | Leu   | Gly   | Tyr   | Leu   | Gly   | Leu   | Asn   | Arg   | Ala   | Ala   | Arg   | His   |       |       |
|       |       |       |       | 565   |       |       |       |       | 570   |       |       |       |       | 575   |       |       |       |
| Leu   | Cys   | Pro   | Pro   | Leu   | Pro   | Thr   | Pro   | Cys   | Ala   | Ser   | Ser   | Ala   | Ile   | Glu   | Phe   |       |       |
|       |       |       | 580   |       |       |       |       | 585   |       |       |       |       | 590   |       |       |       |       |
| Pro   | Gly   | Gly   | Lys   | Glu   | Thr   | Trp   | Gln   | Trp   | Ile   | Asn   | Pro   | Val   | Asp   | Phe   | Gln   |       |       |
|       |       | 595   |       |       |       |       | 600   |       |       |       |       | 605   |       |       |       |       |       |
| Glu   | Glu   | Ala   | Ser   | Leu   | Gln   | Glu   | Ala   | Leu   | Val   | Val   | Glu   | Met   | Ser   | Trp   | Asp   |       |       |
|       | 610   |       |       |       |       | 615   |       |       |       |       | 620   |       |       |       |       |       |       |
| Lys   | Gly   | Glu   | Arg   | Thr   | Glu   | Pro   | Leu   | Glu   | Lys   | Thr   | Glu   | Leu   | Pro   | Glu   | Gly   |       |       |
| 625   |       |       |       |       | 630   |       |       |       |       | 635   |       |       |       |       | 640   |       |       |
| Ala   | Pro   | Glu   | Leu   | Ala   | Leu   | Asp   | Thr   | Glu   | Leu   | Ser   | Leu   | Glu   | Asp   | Gly   | Asp   |       |       |
|       |       |       |       | 645   |       |       |       |       | 650   |       |       |       |       | 655   |       |       |       |
| Arg   | Cys   | Lys   | Ala   | Lys   | Met   |       |       |       |       |       |       |       |       |       |       |       |       |
|       |       |       | 660   |       |       |       |       |       |       |       |       |       |       |       |       |       |       |

( 2 ) INFORMATION FOR SEQ ID NO:3:

( i ) SEQUENCE CHARACTERISTICS:
        ( A ) LENGTH: 660 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

|       |       |       |       |       |       |       |       |       |       |       |       |       |       |       |       |
|-------|-------|-------|-------|-------|-------|-------|-------|-------|-------|-------|-------|-------|-------|-------|-------|
| Met   | Glu   | Pro   | Leu   | Val   | Thr   | Trp   | Val   | Val   | Pro   | Leu   | Leu   | Phe   | Leu   | Phe   | Leu   |
| 1     |       |       |       | 5     |       |       |       |       | 10    |       |       |       |       | 15    |       |
| Leu   | Ser   | Arg   | Gln   | Gly   | Ala   | Ala   | Cys   | Arg   | Thr   | Ser   | Glu   | Cys   | Cys   | Phe   | Gln   |
|       |       |       | 20    |       |       |       |       | 25    |       |       |       |       | 30    |       |       |
| Asp   | Pro   | Pro   | Tyr   | Pro   | Asp   | Ala   | Asp   | Ser   | Gly   | Ser   | Ala   | Ser   | Gly   | Pro   | Arg   |
|       |       | 35    |       |       |       |       | 40    |       |       |       |       | 45    |       |       |       |
| Asp   | Leu   | Arg   | Cys   | Tyr   | Arg   | Ile   | Ser   | Ser   | Asp   | Arg   | Tyr   | Glu   | Cys   | Ser   | Trp   |
|       | 50    |       |       |       |       | 55    |       |       |       |       | 60    |       |       |       |       |
| Gln   | Tyr   | Glu   | Gly   | Pro   | Thr   | Ala   | Gly   | Val   | Ser   | His   | Phe   | Leu   | Arg   | Cys   | Cys   |
| 65    |       |       |       |       | 70    |       |       |       |       | 75    |       |       |       |       | 80    |
| Leu   | Ser   | Ser   | Gly   | Arg   | Cys   | Cys   | Tyr   | Phe   | Ala   | Ala   | Gly   | Ser   | Ala   | Thr   | Arg   |
|       |       |       |       | 85    |       |       |       |       | 90    |       |       |       |       | 95    |       |
| Leu   | Gln   | Phe   | Ser   | Asp   | Gln   | Ala   | Gly   | Val   | Ser   | Val   | Leu   | Tyr   | Thr   | Val   | Thr   |
|       |       |       | 100   |       |       |       |       | 105   |       |       |       |       | 110   |       |       |
| Leu   | Trp   | Val   | Glu   | Ser   | Trp   | Ala   | Arg   | Asn   | Gln   | Thr   | Glu   | Lys   | Ser   | Pro   | Glu   |
|       |       | 115   |       |       |       |       | 120   |       |       |       |       | 125   |       |       |       |
| Val   | Thr   | Leu   | Gln   | Leu   | Tyr   | Asn   | Ser   | Val   | Lys   | Tyr   | Glu   | Pro   | Pro   | Leu   | Gly   |
|       | 130   |       |       |       |       | 135   |       |       |       |       | 140   |       |       |       |       |
| Asp   | Ile   | Lys   | Val   | Ser   | Lys   | Leu   | Ala   | Gly   | Gln   | Leu   | Arg   | Met   | Glu   | Trp   | Glu   |
| 145   |       |       |       |       | 150   |       |       |       |       | 155   |       |       |       |       | 160   |
| Thr   | Pro   | Asp   | Asn   | Gln   | Val   | Gly   | Ala   | Glu   | Val   | Gln   | Phe   | Arg   | His   | Arg   | Thr   |
|       |       |       |       | 165   |       |       |       |       | 170   |       |       |       |       | 175   |       |
| Pro   | Ser   | Ser   | Pro   | Trp   | Lys   | Leu   | Gly   | Asp   | Cys   | Gly   | Pro   | Gln   | Asp   | Asp   | Asp   |
|       |       |       | 180   |       |       |       |       | 185   |       |       |       |       | 190   |       |       |
| Thr   | Glu   | Ser   | Cys   | Leu   | Cys   | Pro   | Leu   | Glu   | Met   | Asn   | Val   | Ala   | Gln   | Glu   | Phe   |
|       |       | 195   |       |       |       |       | 200   |       |       |       |       | 205   |       |       |       |

-continued

```
Gln Leu Arg Arg Arg Gln Leu Gly Ser Gln Gly Ser Ser Trp Ser Lys
    210                 215                 220

Trp Ser Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
        275                 280                 285

Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
                325                 330                 335

Asp Thr His Thr Glu Pro Val Ala Leu Asn Ile Ser Val Gly Thr Asn
            340                 345                 350

Gly Thr Thr Met Tyr Trp Pro Ala Arg Ala Gln Ser Met Thr Tyr Cys
        355                 360                 365

Ile Glu Trp Gln Pro Val Gly Gln Asp Gly Gly Leu Ala Thr Cys Ser
    370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
            420                 425                 430

Val Leu Ser Thr Tyr His Phe Gly Gly Asn Ala Ser Ala Ala Gly Thr
        435                 440                 445

Pro His His Val Ser Val Lys Asn His Ser Leu Asp Ser Val Ser Val
    450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
        515                 520                 525

Gly Val Trp Ser Gln Pro Gln Arg Phe Ser Ile Glu Val Gln Val Ser
    530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
        595                 600                 605

Glu Glu Ala Ser Leu Gln Glu Ala Leu Val Val Glu Met Ser Trp Asp
    610                 615                 620

Lys Gly Glu Arg Thr Glu Pro Leu Glu Lys Thr Glu Leu Pro Glu Gly
625                 630                 635                 640
```

```
Ala  Pro  Glu  Leu  Ala  Leu  Asp  Thr  Glu  Leu  Ser  Leu  Glu  Asp  Gly  Asp
               645                      650                      655
Arg  Cys  Asp  Arg
          660
```

RECOMBINANT DNA ENCODING HUMAN RECEPTOR FOR INTERLEUKIN-12

CROSS-REFERENCE TO RELATED APPLICATION

This application is a continuation-in-part application of Ser. No. 094,713, filed Jul. 19, 1993, now abandoned.

FIELD OF INVENTION

This invention relates generally to cytokine receptors and more specifically relates to Interleukin-12 receptors.

BACKGROUND OF THE INVENTION

Interleukin-12 (IL-12), formerly known as cytotoxic lymphocyte maturation factor or natural killer cell stimulatory factor, is a 75-KDa heterodimeric cytokine composed of disulfide-bonded 40-KDa (p40) and -KDa (p35) subunits that has pleiotropic activities including stimulation of the proliferation of activated T and NK cells (Gately, M. K., et al., 1991, J. Immunol., 147:874) (Kobayashi, M., et al., 1989, J. Exp. Med., 170:827), enhancement of the lytic activity of NK/LAK cells (Kobayashi, M., et al., supra) (Stern, A. S., et al., 1990, Proc. Natl. Acad. Sci. USA, 87:6808), enhancement of cytolytic T-cell responses (M. Gately et al., 1992, Cell. Immunology, 143:127), induction of interferon gamma by resting and activated T- and NK-cells (M. Kobayashi et al., supra; S. H. Chan et al., 1991, J. Exp. Med., 173:869), and promotion of $T_h1$-type helper cell responses (R. Manetti et al., 1993, J. Exp. Med., 177:1199; C. S. Hsieh et al., 1993, Science 260:547).

The biological activity of IL-12 is mediated by the binding of the IL-12 molecules to cell surface, or plasma membrane, receptors on activated T- and NK cells; however, the contributions of the individual subunits, p35 and p40, to receptor binding and signal transduction remain unknown. Studies with labeled IL-12 have shown that this binding occurs in a specific and saturable manner. IL-12 delivers a signal to target cells through a receptor that was initially characterized on PHA-activated CD4+ and CD8+ T-cells and on IL-2 activated CD56+ NK-cells (R. Chizzonite et al., 1992, J. Immunol., 148:3117; B. Desai, et al., 1992, J. Immunol., 148:3125). A survey of over 20 human cell lines belonging to the T-, B-, NK- and myelomonocytic lineages only identified a single CD4+, IL-2 dependent human T-cell line (Kit 225) that constitutively expresses the IL-12 receptor and responds to IL-12 (B. Desai, et al., 1992, J. Immunol., 148:3125; B. Desai, et al., 1993, J. Immunol. 150:207A). Freshly prepared PHA-activated PBMC and the Kit 225 cell line thus represent two convenient cell sources to study the biochemistry of the functional IL-12 receptor; there may be others. Equilibrium binding experiments with $^{125}$I-labeled IL-12 showed that i) PHA-activated PBMC express several thousand IL-12 receptors which show 3 classes of affinities: high =5–20 pM, intermediate =50–200 pM and low =2–6 nM; ii) IL-12 receptor expression on PBMC is upregulated by mitogen or IL-2 stimulation; and iii) the IL-12 receptor upregulation correlates with the ability of the cells to proliferate in response to IL-12 (R. Chizzonite, et al., 1992, J. Immunol., 148:3117; B. Desai, et al., 1992, J. lmmunol., 148:3125). It was not clear at this point whether the biologically functional IL-12 receptor consists of one or more subunits. Affinity crosslinking of labeled IL-12 to activated PBMC demonstrated I 0 the size of the cell surface IL-12 binding protein(s) under nonreducing conditions to be in the range of about 150 KDa to about 200 KDa. Additional affinity crosslinking and immunoprecipitation experiments with unlabeled IL-12 bound to $^{125}$I-surface labeled activated PBMC identified an IL-12 binding protein that under reducing conditions had a size of about 110 KDa (R. Chizzonite, et al., 1992, J. Immunol., 148:3117).

Using a non-neutralizing monoclonal antibody to the IL-12 receptor, we have now succeeded in isolating a human eDNA that encodes a low affinity (5–10 nM) IL-12 receptor. This protein belongs to the cytokine receptor superfamily and within that family shows strongest homology to gp130.

In order for a molecule such as IL-12 to exert its effect on cells, it is now accepted by those skilled in the art that the molecule must interact with molecules, located on cell membranes, referred to as receptors. Patents which exemplify disclosures of interleukin receptors include Honjo et al., U.S. Pat. No. 4,816,565; Urdal et al., U.S. Pat. No. 4,578,335; Dower et al., U.S. Pat. No. 5,180,812; and Taniguchi et al., U.S. Pat. No. 5,198,359, the disclosures of which are incorporated by reference.

Fanslow, W. C. et al., Science 248:739–41 (May 11, 1990) presented data showing that the effect of IL-1 in vivo could be regulated via the administration of a soluble form of its receptor. The results that Fanslow report demonstrate the ability of a soluble cytokine receptor (soluble IL-1R) to modulate biological activity upon exogenous administration in vivo, presumably by acting as a neutralizing agent for the endogeneously produced, corresponding ligand (IL-1), and provides evidence of the therapeutic potential of soluble cytokine receptors in a variety of clinical disorders. Systemic administration of a soluble, extracellular portion of the receptor for IL-1 (soluble IL-1R) had profound inhibitory effects on the development of in vivo alloreactivity. Survival of heterotopic heart allografts was prolonged from 12 days in controls to 17 days in mice treated with soluble IL-1R. Lymph node hyperplasia in response to localized injection of allogeneic cells was completely blocked by soluble IL-1R treatment. What types of therapeutic efficacy that administration of soluble IL-12 receptor is expected to have can also be contemplated therefor by those skilled in the art.

The availability of the purified receptor, in soluble form, presents therapeutic possibilities as well, as shown by Fanslow above. Addition of soluble IL-12 receptor interferes with the effect of the interleukin on the cells, since the molecule cannot bind to the cell membrane as freely. Hence, an aspect of the invention is the treatment of pathological conditions caused by excess activity of cells possessing IL-12 receptors by adding an amount of soluble IL-12 receptors sufficient to inhibit binding of IL-12 to the aforementioned cells. This methodology can also be modified, and the soluble receptor can also be used as a screening agent for pharmaceuticals. Briefly, a pharmaceutical which works as an IL-12 antagonist can do so by blocking the binding of IL-12 to the IL-12 receptor. Prior to determining whether a material would be effective in vivo, one may use the purified IL-12 receptor in connection with a potential pharmaceutical to determine if there is binding. If not, then the pharmaceutical may no longer be a desirable candidate. If there is in fact binding, further testing may be indicated.

SUMMARY OF THE INVENTION

The present invention is directed towards an isolated cDNA coding for a human low affinity IL-12 receptor protein or subunit thereof. When expressed in mammalian cells, the cDNA gives rise to substantially homogeneous IL-12 receptor protein that binds IL-12 in a specific and saturable manner with an apparent affinity of about 2 to about 10 nM.

BRIEF DESCRIPTION OF THE DRAWINGS

FIG. 1: DNA sequence of human IL-12 receptor cDNA clone No. 5. (translated portion=nucleotides 65 to 2050) (SEQ ID NO:1).

FIG. 2: Amino acid sequence of human IL-12 receptor protein as deduced from eDNA sequence of FIG. 1. (underlined amino acid residues of N-terminal sequence=signal peptide sequence; amino acid residues nos. 541 to 571= transmembrane area marked by ---;6 potential N-linked glycosylation sites in the extracellular portion marked by - - - ; conserved areas 1 and 2 of the cytoplasmic domain are marked by --- [amino acid residues nos. 577 to 584 and 618 to 629] (SEQ ID NO:2).

FIG. 3: Alignment of the IL-12 receptor protein subunit sequence with human gp130, human granulocyte colony-stimulating factor-receptor (G-CSF-R) and leukemia inhibitory factor-receptor (LIF-R), and resulting consensus sequence. Consensus residues indicated by lowercase letters refer to identities between IL-12 receptor and gp130 only. The following sequence ranges were used: IL-12 receptor protein (SEQ ID NO:2): residues 42–662; gp130: residues 124–742 (M. Hibi et al., 1990, Cell, 63: 1149); G-CSF-R: residues 98–731 (R. Fukunaga, et al., 1990, Proc. Natl. Acad. Sci (USA), 87:8702); LIF-R: residues 331–950 (D. P. Gearing, et al., 1991, EMBO J., 10:2839).

FIG. 9: Immunoprecipitation of the Solubilized $^{125}$I-IL-12/IL-12R Crosslinked Complex by Anti-IL-12R Antibodies FIG. 10: Equilibrium binding of $^{125}$I-2-4E6 to PHA-activated PBMC at Room Temperature

DETAILED DESCRIPTION OF THE INVENTION

Figure 4B:
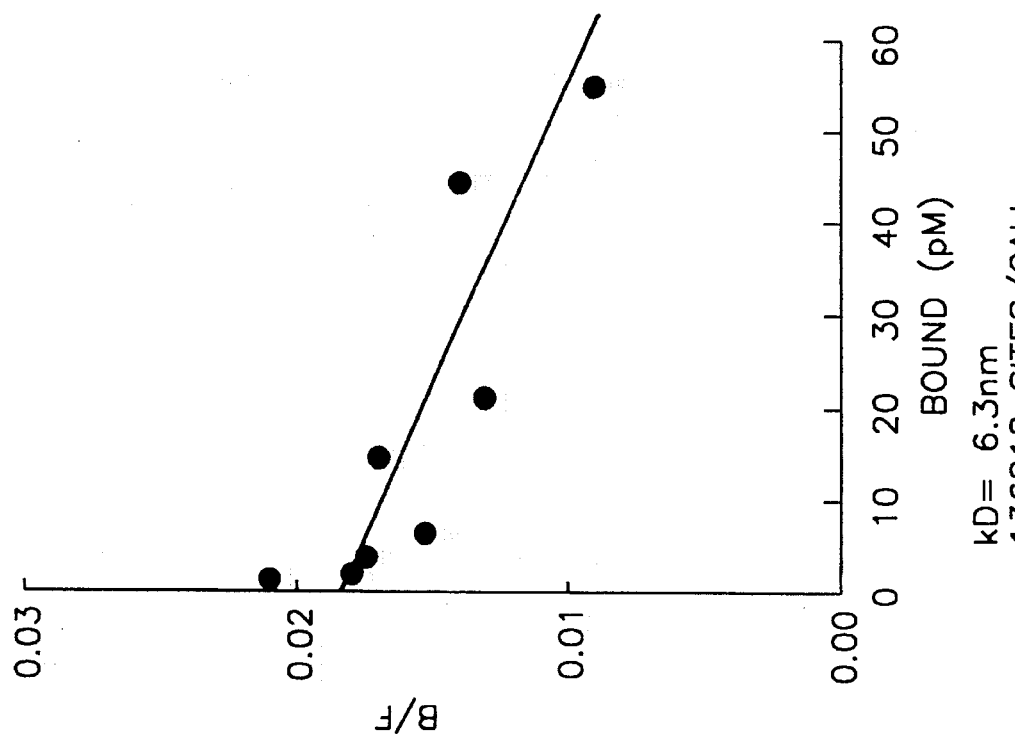
FIG. 4B: Scatchard analysis of 2-4E6 antibody binding to recombinant human IL-12 receptor expressed in COS cells.

The present invention is directed towards an isolated cDNA (SEQ ID NO:1) that encodes a human low-affinity IL-12 receptor protein (SEQ ID NO:2) (clone no. 5) or subunit thereof. The amino acid sequence of the substantially homogeneous IL-12 receptor protein as deduced from the cDNA sequence is shown in FIG. 2 (SEQ ID NO:2). Clone number 17 (SEQ ID NO:3) is also of a substantially homogeneous IL-12 receptor.

The IL-12 receptor cDNA is useful for the following purposes:

Expression of recombinant IL-12 receptor protein in high levels and its use as an antigen allows production of additional neutralizing monoclonal and polyclonal antibodies. Such neutralizing antibodies can be used in in vivo model settings to elucidate the role that IL-12 and its receptor play in normal as well as pathologic immune responses (i.e. disease states that are aggravated by activated T- and NK-cells like autoimmune diseases, graft versus host disease and rheumatoid arthritis).

IL-12 receptor proteins can be administered, for example, for the purpose of suppressing immune responses in a human. A variety of diseases or conditions are caused by an immune response to alloantigen, including allograft rejection and graft-versus-host reaction. In alloantigen-induced immune responses, IL-12 receptor may suppress lymphoproliferation and inflammation which result upon activation of T cells. IL-12 receptor may therefore be used to effectively suppress alloantigen-induced immune responses in the clinical treatment of, for example, rejection of allografts (such as skin, kidney, and heart transplants), and graftversus-host reactions in patients who have received bone marrow transplants.

IL-12 receptor may also be used in clinical treatment of autoimmune dysfunctions, such a rheumatoid arthritis, diabetes and multiple sclerosis, which are dependent upon the activation of T cells against antigens not recognized as being indigenous to the host. IL-12 receptor may also be useful in treatment of septic shock in which interferon gamma produced in response to IL-12 plays a central role in causing morbidity and mortality (G. M. Doherty et al., 1992, J. Immunol. 149:1666).

Purified IL-12 receptor compositions will be useful in diagnostic assays for IL-12 or IL-12 receptor, and also in raising antibodies to IL- 12 receptor for use in diagnosis or therapy. In addition, purified IL-12 receptor compositions may be used directly in therapy to bind or scavenge IL-12, thereby providing a means for regulating the immune or inflammatory activities of IL-12. In its use to prevent or reverse pathologic immune responses, soluble IL-12 receptor can be combined with other cytokine antagonists such as antibodies to the IL-2 receptor, soluble TNF (tumor necrosis factor) receptor, the IL-1 receptor antagonist, and the like.

The dose ranges for the administration of the IL-12 receptor proteins and fragments thereof may be determined by those of ordinary skill in the art without undue experimentation. In general, appropriate dosages are those which are large enough to produce the desired effect, for example, blocking the binding of endogenous IL-12 to its natural receptor. The dosage should not be so large as to cause adverse side effects, such as unwanted cross-reactions, anaphylactic reactions, and the like. Generally, the dosage will vary with the age, condition, sex and extent of disease in the patient, counter indications, if any, immune tolerance and other such variables, to be adjusted by the individual physician. The IL-12 receptor proteins and fragments thereof can be administered parenterally by injection or by gradual perfusion over time. They can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol., vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See, generally, *Remington's Pharmaceutical Science*, 16th Ed., Mack Eds., 1980.

As used herein, "DNA sequence"0 refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal non-translated sequences, or introns, which are typically present in eukaryotic genes. However, it will be evident that genomic DNA containing the relevant sequences could also be used. Sequences of non-translated DNA may be present 5' or 3' from the open reading frame, where the same do not interfere with manipulation or expression of the coding regions.

As used herein, "recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in various eukaryotic expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

MATERIALS AND METHODS

Proteins and Plasmids

Recombinant human IL-12 (U. Gubler et al., 1991, Proc. Natl. Acad. Sci.(USA), 88:4143) and murine IL-12 (D. Schoenhaut et al., 1992, J. Immunology, 148:3433) were obtained as described therein.

The murine anti human IL-12 receptor monoclonal antibody 2- 4E6 used herein was generated as described herein below in Examples 1 to 16 and was purified from ascites fluids by affinity chromatography on protein G-agarose according to the manufacturer's instructions (Genex). The proteins were labeled with 1–125 by a modification of the Iodogen method as described (Pierce Chemical Co., Rockford, IL). Radiospecific activities of 5000–7000 cpm/fmole for IL-12 and 1500–2500 cpm/fmole for the 2-4E6 antibody were typically obtained.

The plasmid pEF-BOS was obtained from Dr. Nagata at the Osaka Bioscience Institute in Japan. The plasmid is based on a pUC 119 backbone and contains the elongation factor 1 alpha promoter to drive expression of genes inserted at the BstXI site (S. Mizushima and S. Nagata, Nucl. Acids Res., 1990, 18:5322).

The murine anti. human IL-12 receptor monoclonal antibody 2- 4E6 was prepared, characterized, and generated as set forth in U.S. patent application Ser. No. 08/094,649, filed Jul. 19, 1993, now abandoned, which has been refiled as a continuation-in-part application Ser. No. 08/248,531, filed, May 31, 1994, the contents of both applications being expressly incorporated by reference herein and is as follows:

EXAMPLE 1

Preparation, Characterization & Purification of Hybridoma Antibodies

Balb/c mice (Charles River Laboratories) were immunized by the intraperitoneal route with PHA (phytohemagglutanin-activated) human PBMC (peripheral blood mononuclear cells) (PHA-activated PBMC) at $6 \times 10^7$ cells/mouse. Mice received 5 subsequent booster injections of between $2-5 \times 10^7$ cells over a six month period. For preparation of activated spleen cells, 2 mice were injected intraperitoneally and intravenously with $1 \times 10^7$ and $2.5 \times 10^6$ cells, respectively, on two successive days, starting four days prior to the cell fusion. Spleen cells were isolated from these mice and fused with SP2/0 cells at a ratio of 1:1 with 35% v/v polyethylene glycol 4000 (E. Merck) according to the method of Fazekas et al., J. Immunol. Methods 35, 1 (1980). The fused cells were plated at a density of 6×10⁵ cells/ml/well in 48-well cluster dishes in IMDM supplemented with 10% FBS, glutamine (2 mM), b-mercaptoethanol (0.1 mM), gentamicin (50 g/ml), 5% ORIGEN hybridoma cloning factor (IGEN, Inc.), 5% P388D1 supernatant (Nordan, R. P., et al., J. Immunol., 139:813 (1987)) and 100 Units/ml rHuIL-6. Hybridoma supernatants were assayed for specific anti-IL-12 receptor antibodies by: 1) immunoprecipitation of the soluble complex of $^{125}$I-HuIL-12 crosslinked to IL-12 receptor ($^{125}$I-IL-12/IL-12R); 2) inhibition of $^{125}$I-HuIL-12 binding to PHA-activated PBMCs; and 3) differential binding to IL-12 receptor positive cells versus receptor negative cells. Hybridoma cell lines secreting specific anti-receptor antibodies were cloned by limiting dilution. Antibodies were purified from ascites fluids by affinity chromatography on Protein G bound to cross-linked agarose according to the manufacturer's protocol (Genex).

EXAMPLE 2

Preparation of Human PHA Lymphoblasts and IL-12 Receptor Binding Assays

Human peripheral blood mononuclear cells were isolated (see Gately et al., J. Natl. Cancer Inst. 69, 1245 (1982)) and cultured at 37° C. at a density of 5×10⁵ cells/ml in tissue culture medium (TCM) containing 0.1% PHA-P (Difco). After 3 days, the cultures were split 1:1 with fresh TCM, and human rIL-2 was added to each culture to give a final concentration of 50 units/ml. The cultures were then incubated for an additional 1–2 days prior to use in assays.

PHA-activated human PBMC were washed once in binding buffer (RPMI-1640, 5% FBS, 25 mM HEPES pH 7.4) and resuspended in binding buffer to a cell density of 7×10⁶ cells/mi. Lymphoblasts (7×10⁵ cells) were incubated with various concentrations of $^{125}$I-IL-12 (5–10000 pM) at room temperature for the designated times. Cell bound radioactivity was separated from free $^{125}$I-IL-12 by centrifugation of the assay mixture through 0.1 ml of an oil mixture (1:2 mixture of Thomas Silicone Fluid 6428-R15 {A. H. Thomas} and Silicone Oil AR 200 {Gallard-Schlessinger}) at 4° C. for 90 sec at 10,000×g. The tip containing the cell pellet was excised, and cell bound radioactivity was determined in a gamma counter. Non-specific binding was determined by inclusion of 100 nM unlabeled IL-12 in the assay. Incubations were carried out in duplicate or triplicate. Receptor binding data were analyzed by using the non-linear regression programs EBDA and LIGAND as adapted for the IBM personal computer (McPherson, J. Pharmacol Methods 14, 213 (1985)) from Elsevier-BIOSOFT.

EXAMPLE 3

Affinity Cross-Linking of $^{125}$I-IL-12 to IL-12 Receptor Bearing Cell Lines

IL-12 receptor bearing cells were incubated with $^{125}$I-IL-12 (100–500 pM) in the presence or absence of excess unlabeled IL-12 for 2 hr at room temperature. The cells were then washed with ice-cold PBS pH 8.3 (25 mM Sodium Phosphate pH 8.3, 0.15 M NaCl and 1 mM MgCl₂) and resuspended at a concentration of 0.5–1.0×10⁷ cells/ml in PBS pH 8.3. BS3 (Pierce) in dimethyl sulfoxide was added to a final concentration of 0.4 mM. Incubation was continued for 30 min. at 4° C. with constant agitation. The cells were washed with ice-cold 25 mM Tris-HCl (pH 7.5), 0.15 M NaCl and 5 mM EDTA and then solublized at 0.5–1.0× 10⁸ cells/ml in solubilization buffer (50 mM Tris-HCl (pH 8.0) containing 8 mM CHAPS, 0.25 M NaCl, 5 mM EDTA, 40 μg/ml PMSF, 0.05% NAN₃, and 1% BSA) for 1 hr at 4° C. The extracts were centrifuged at 12,000×g for 45 min. at 4° C. to remove nuclei and other debris.

EXAMPLE 4

Immunoprecipitation Assay of the Soluble Complex of $^{125}$I-IL-12 Crosslinked to Human IL-12R.

For the immunoprecipitation assay, hybridoma culture supernatant (0.5 ml), diluted antisera, or purified IgG was added to a microfuge tube containing 0.1 ml of a 50% suspension of either goat-anti-mouse IgG coupled to agarose (Sigma Chem. Co.) or Protein G coupled to Sepharose 4B (Pharmacia). The assay volume was brought up to 1.0 ml with IP buffer (8 mM CHAPS in PBS (0.25 M NaCl), 1% BSA, & 5 mM EDTA) and the mixture was incubated on a rotating mixer for 2 hr at room temperature. The beads were pelleted by centrifugation, resuspended in 1 ml IP buffer containing $^{125}$I-IL-12/IL-12R ( 10–20,000 cpm) and the mixture was incubated on a rotating mixer for 16 hr at 4° C. After this incubation, the beads were pelleted by centrifugation and washed twice in IP buffer without BSA. The $^{125}$I-labeled receptor complex bound to the solid phase antibodies was released by adding 100 μl of 2×Laemmli sample buffer (Nature 227, 680 (1970)) with and without 10% b-mercaptoethanol and heating for 5 min. at 95° C. The immunoprecipitated proteins were analyzed by SDS-PAGE on 8% or 4–15% gradient polyacrylamide gels and visualized by autoradiography.

EXAMPLE 5

Assays for IL-12R Solubilized from Cells Expressing IL-12 Receptor

To confirm that the antibodies identified by the immunoprecipitation assay were specific for IL-12R, an immunoprecipitation/soluble IL-12R binding assay was developed. As described in Example 1 above, antibodies (as hybridoma supernatant, purified IgG (50 μg) or antisera) were immobilized by binding to goat anti-mouse IgG coupled to agarose (100 μl; Sigma Chemical Co.) or protein G coupled to Sepharose 4B (100 μl; Pharmacia). For some experiments, antibodies were covalently crosslinked to protein G-Sepharose 4B, before being used in the assay. See Stern and Podlaski, Techniques in Protein Chemistry (1993). The immobilized antibodies were resuspended in IP buffer (0.3 ml) and 0.2 ml of a detergent solubilized extract of PHA-activated PBMCs or K6 cells that contained IL-12R was added. To prepare the detergent solubilized IL-12R preparation, the cells were washed with ice-cold 25 mM Tris-HCl (pH 7.5), 0.15 M NaCl and 5 mM EDTA and then solublized at 1.5×10⁸ cells/ml in solubilization buffer (50 mM Tris-HCl, pH 8.0, containing 8 mM CHAPS, 0.25 M NaCl, 5 mM EDTA, 40 μg/ml PMSF, 0.05% NAN₃, and 1% BSA) for 1 hr at 4° C. The extracts were centrifuged at 120,000×g for 60 min. at 4° C. to remove nuclei and other debris. The mixture was incubated on a rotating mixer for 16 hr at 4° C. After this incubation, the beads were pelleted by centrifugation and resuspended in IP buffer (0.15 ml) containing $^{125}$I-HuIL-12 at concentrations ranging from 0.05 to 7.5 nM.

The IL-12R immobilized on the antibody coated beads was incubated with $^{125}$I-HuIL-12 for 2 hrs. at room temperature on a shaker. Following this incubation, the beads were pelleted, washed twice with IP buffer and the bound radioactivity determined in a gamma counter. Nonspecific binding was determined by inclusion of 70 nM unlabeled human IL-12 in the assay. Solubilized IL-12R binding data were analyzed according to the method of Scatchard using the nonlinear regression programs EBDA and LIGAND from Elsevier-BIOSOFT.

EXAMPLE 6

Competitive Inhibition of $^{125}$I-IL-12 Receptor Binding by Antibodies

The ability of hybridoma supernatant solutions, purified IgG, or antisera to inhibit the binding of $^{125}$I-IL-12 to PHA-activated lymphoblasts was measured as follows: serial dilutions of culture supernatants, purified IgG or antisera were mixed with activated lymphoblasts (1–1.5×10$^6$ cells) in binding buffer (RPMI-1640, 5% FBS+25 mM HEPES pH 7.4) and incubated on an orbital shaker for 1 hour at room temperature. $^{125}$I-HuIL-12 (1×10$^5$ cpm) was added to each tube and incubated for 1–2 hours at room temperature. Non-specific binding was determined by inclusion of 10 nM unlabeled IL-12 in the assay. Incubations were carried out in duplicate or triplicate. Cell bound radioactivity was separated from free $^{125}$I-IL-12 by centrifugation of the assay through 0.1 ml of an oil mixture as described above. The tip containing the cell pellet was excised, and cell bound radioactivity was determined in a gamma counter.

EXAMPLE 7

Labeling of Human IL-12 and mAb 2-4E6 with $^{125}$I

Human IL-12 and purified 2-4E6 IgG were labeled with $^{125}$I by a modification of the Iodogen method (Pierce Chemical Co., Rockford, Ill.). Iodogen was dissolved in chloroform and 0.05 mg dried in a 12×15 mm borosilicate glass tube. For radiolabeling, 1.0 mCi Na[$^{125}$I] (Amersham, Chicago, Ill.) was added to an Iodogen-coated tube containing 0.05 ml of Tris-iodination buffer (25 mM Tris-HCL pH 7.5, 0.4 M NaCl and 1 mM EDTA) and incubated for 4 min at room temperature. The activated $^{125}$I solution was transferred to a tube containing 0.05 to 0.1 ml IL-12 (7 µg) or IgG (100 µg) in Tris-iodination buffer and the reaction was incubated for 9 min at room temperature. At the end of the incubation, 0.05 ml of Iodogen stop buffer (10 mg/ml tyrosine 10% glycerol in Dulbecco's PBS, pH 7.40) was added and reacted for 3 min. The mixture was then diluted with 1.0 ml Tris-iodination buffer, and applied to a Bio-Gel P10DG desalting column (BioRad Laboratories (BRL)) for chromatography. The column was eluted with Tris-iodination buffer, and fractions (1 ml) containing the peak amounts of labeled protein were combined and diluted to 1×10$^8$ cpm/ml with 1% BSA in Tris-iodination buffer. The TCA preciptable radioactivity (10% TCA final concentration) was typically in excess of 95% of the total radioactivity. The radiospecific activity was typically~1500 to 2500 cmp/fmol for 2-4E6 IgG and 5000 to 7000 cpm/fmole for IL-12.

EXAMPLE 8

Binding Assays of $^{125}$I-2-4E6 to Intact Cells

PHA-activated human PBMC were washed once in binding buffer (RPMI 1640, 5% FBS and 25 mM HEPES, pH 7.4) and resuspended in binding buffer to a cell density of 1.5×10$^7$ cells/mi. Lymphoblasts (1.5×10$^6$ cells) were incubated with various concentrations of $^{125}$I-2- 4E6-IgG (0.005 to 2 nM) at room temperature for 1.5 hrs. Cell bound radioactivity was separated from free $^{125}$I-2-4E6 IgG by centrifugation of the assay mixture through 0.1 ml silicone oil at 4° C. for 90 seconds at 10,000×g. The tip containing the cell pellet was excised, and cell bound radioactivity was determined in a gamma counter. Non-specific binding was determined by inclusion of 67 nM unlabeled 2-4E6 IgG in the assay. Incubations were carried out in duplicate or triplicate. Receptor binding data were analyzed by using the nonlinear regression programs EBDA, LIGAND and Kinetics as adapted for the IBM personal computer from Elsevier BIOSOFT.

EXAMPLE 9

Expression of Recombinant IL-12R in COS Cells and Determination of $^{125}$I-2-4E6 Binding COS cells (4–5×10$^7$) were transfected by electroporation with 25 µg of plasmid DNA expressing recombinant human IL-12R, as described hereinbelow, in a BioRad Gene Pulser (250 µF, 250 volts) according to the manufacturer's protocol. The cells were plated in a 600 cm$^2$ culture plate, harvested after 72 hours by scraping, washed and resuspended in binding buffer. Transfected cells (8×10$^4$) were incubated with increasing concentrations of $^{125}$I-labeled 2-4E6 or IL-12 at room temperature for 2 hrs. Cell bound radioactivity was separated from free $^{125}$I-labeled 2-4E6 or IL-12 as described above.

EXAMPLE 10

Western Blot Analysis of Soluble IL-12R with mAb 2-4E6

PHA-activated PBMC were washed 3 times with ice-cold PBS and solubilized at 0.5–1×10$^8$ cells/ml in solubilization buffer (50 mM TrisHCl pH 8.0 containing 8 mM CHAPS, 0.25 M NaCl, 5 mM EDTA, 40 µg/ml PMSF, 0.05% NaN$_3$ and 1 mg/ml BSA)for 1 hr at 4° C. The extracts were centrifuged at 12,000×g for 45 min. at 4° C. to remove nuclei and other debris. The extracts were incubated with 2-4E6 IgG or control IgG bound to goat-anti-mouse IgG immobilized on cross-linked agarose (Sigma Chemical Co.). The precipitated proteins were released by treatment with 0.1 M glycine pH 2.3, neutralized with 3M Tris, mixed with ⅕ volume of 5×Laemmli sample buffer, and separated by SDS/PAGE on 8% pre-cast acrylamide gels (NOVEX). The separated proteins were transferred to nitrocellulose membrane (0.2 mM) for 16 hours at 100 volts in 10 mM TRIS-HCL (pH 8.3), 76.8 mM glycine, 20% methanol and 0.01% SDS. The nitrocellulose membrane was blocked with BLOTTO (5.0% w/v nonfat dry milk in PBS +0.05% Tween 20) and duplicate blots were probed with $^{125}$I-2-4E6 IgG (1×10$^6$ cpm/ml in 8 mM CHAPS in PBS, 0.25 M NaCl, 10% BSA and 5 mM EDTA)+unlabeled 2-4E6 IgG (67 nM).

EXAMPLE 11

Analysis of IL-12 Receptor Expression on Human Cells by Fluorescence Activated Cell Sorting with mAb 2-4E6

To stain cells expressing IL-12 receptor, 1×10⁶ cells in 100 μl staining buffer (PBS containing 2% FBS and 0.1% NAN$_3$) were incubated with 10 μl of 2-4E6 ascites fluid for 25 min. at 4° C. Cells were then washed twice with staining buffer followed by incubation with a 1:100 dilution of goat F(ab)2 anti mouse Ig-PE (Tago, Burlingame Calif.) for 25 min. at 4° C. The stained cells were washed twice with staining buffer and then analyzed on a FACScan flow cytometer (Becton Dickinson).

EXAMPLE 12

Figure 7:
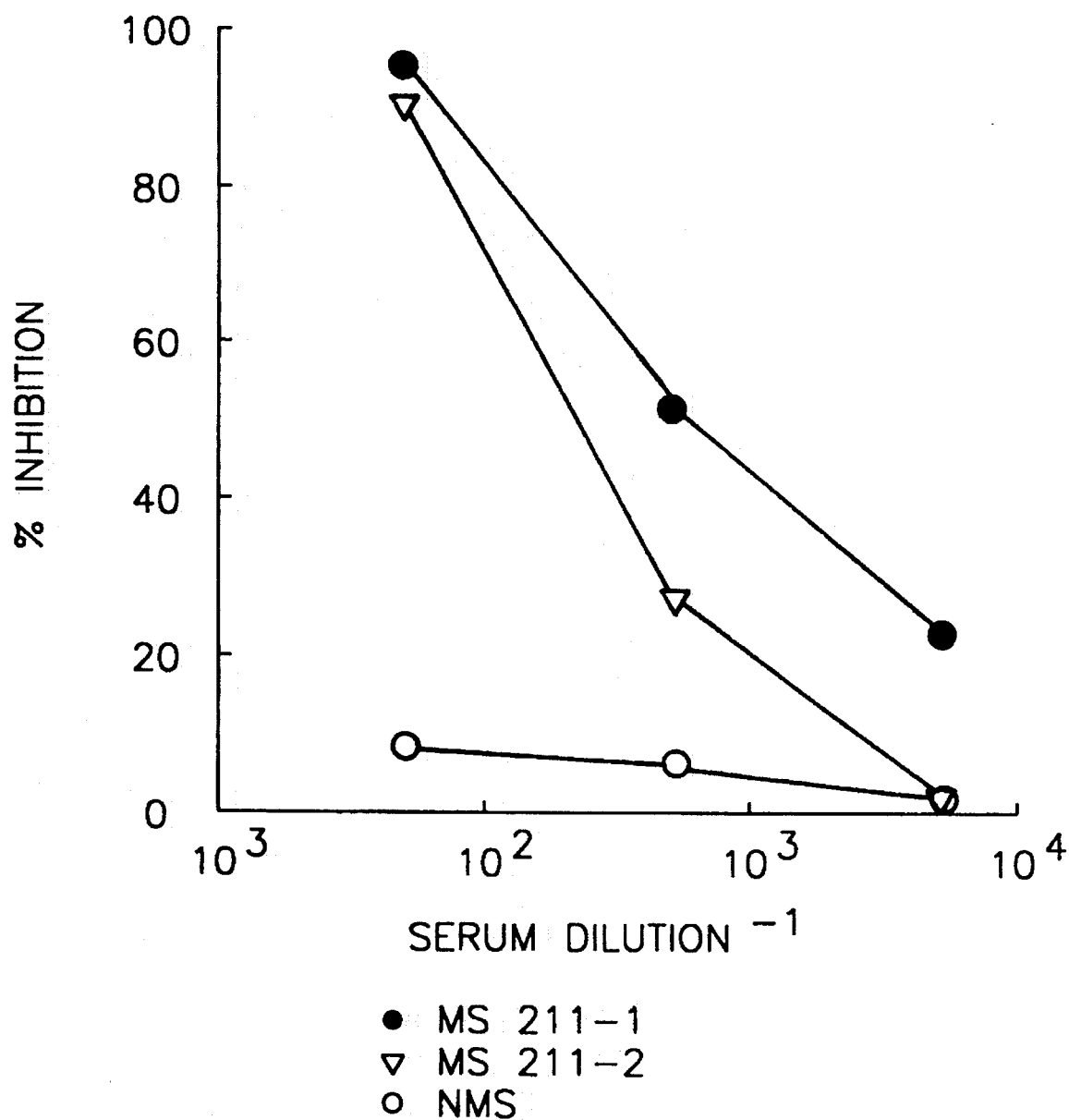
FIG. 7: Inhibition of $^{125}$I-IL-12 Binding to IL-12 (IL-12R) Receptor by Mouse Anti-IL-12R Antiserum

Inhibition of IL-12 Binding to Human PHA-Lymphoblasts by Mouse Anti-IL-12R Antiserum Mice immunized with PHA-activated PB MCs developed an immune response against the human IL-12R as determined by inhibition of $^{125}$I-IL-12 binding to PHA-activated PBMCs (FIG. 7) and immunoprecipitation of the complex of $^{125}$I-IL-12 crosslinked to IL- 12R (data not shown). The dilutions for half-maximal inhibition of $^{125}$I-IL-12 binding to PHA-activated PBMCs were 1/500 and 1/250 for animals 211–1 and 211–2, respectively (FIG. 7). These antisera also neutralized IL-12 biologic activity as measured in a PHA-lymphoblast proliferation assay (data not shown). Spleen cells isolated from these mice were fused with SP2/0 myeloma cells and the resulting hybridomas were initially screened for IL-12R specific antibodies by immunoprecipitation of the $^{125}$I-IL-12/IL-12R complex and by inhibition of $^{125}$I-IL-12 binding to IL-12R.

For FIG. 7, ten fold serial dilutions of mouse anti-IL-12R immune serum (#211-1 and #211-2) and normal mouse serum (NMS) were preincubated with PHA-activated PBMC for 60 min at RT (room temperature) before addition of $^{125}$I-IL-12 (100 pM). After addition of $^{125}$I-IL-12, the reaction was incubated for 1–2 hrs at RT and the cell bound radioactivity was determined. The data are expressed as the % Inhibition of $^{125}$I-IL-12 binding in the presence of the immune serum when compared to the specific binding in the absence of serum.

EXAMPLE 13

Identification and Characterization of Monoclonal Anti-IL-12R Antibodies

Figure 8:
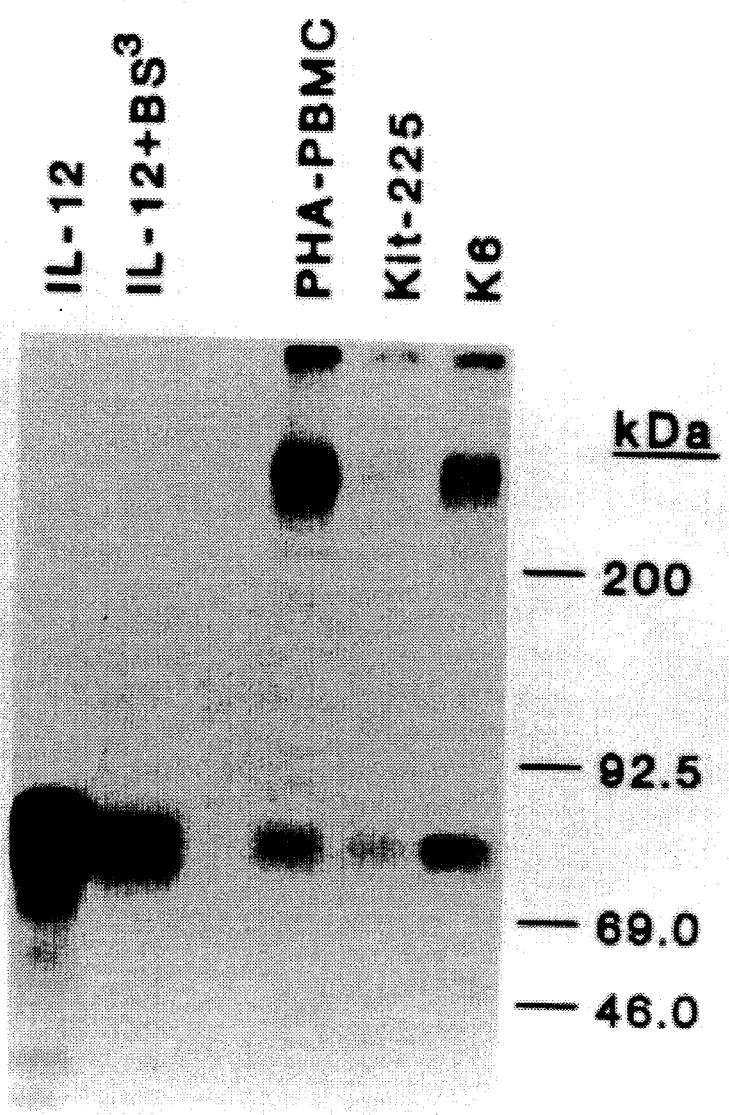
FIG. 8: Characterization of the IL-12 Binding Proteins on IL-12R Positive Human cells by Affinity-Crosslinking

The immunoprecipitation assay identified 13 hybridomas secreting putative non-neutralizing anti-IL-12R antibodies, whereas the IL-12R binding assay identified 3 putative neutralizing IL-12R antibodies (Table 1). The immunoprecipitation assay measured the ability of the putative anti-IL-12R antibodies that are immobilized on a solid phase to capture the solubilized complex of $^{125}$I-IL-12/IL-12R. To verify that the radioactivity immunoprecipitated by the immobilized antibody was present in the complex of $^{125}$I-IL-12/IL-12R, the immunoprecipitated proteins were solubilized, separated by SDS-PAGE and visualized by autoradiography. The preparations of the $^{125}$I-IL- 12/IL-12R complexes solubilized from PHA-activated PBMC, Kit-225 and K6 cells were resolved into two major radioactive bands, 210–250 KDa and 75 KDa (FIG. 8). The 210–250 KDa and 75 KDa complexes were identified as the $^{125}$I-IL-12/IL-12R complex and $^{125}$I-IL-12 not complexed with the receptor, respectively (FIG. 8). See also R. Chizzonite et al., J. Immunol. 148:3117 (1992). The radioactive 75 KDa band visualized from the cell extracts co-migrated with $^{125}$I-IL-12, indicating that it represented $^{125}$I-IL-12 that bound but was not covalently crosslinked to IL-12R. The 210–250 KDa band was not a covalent crosslinked oligomer of $^{125}$I-IL-12 because it is not produced when the crosslinking agent BS3 was added directly to $^{125}$I-IL-12 (FIG. 8).

Hybridoma cells secreting putative anti-IL-12R antibodies were then cloned by limiting dilution and screened by both the immunoprecipitation and inhibition of binding assays that identify nonneutralizing and neutralizing antibodies, respectively. During this cloning and screening process, hybridoma lines secreting putative neutralizing anti-IL-12R antibodies were not recovered, whereas non-neutralizing antibodies were recovered from both the original immunoprecipitation and inhibitory positive hybridomas. After this initial identification and cloning, a direct binding assay was used to determine if the non-neutralizing antibodies only bound to cells expressing IL-12R. This assay demonstrated that the non-neutralizing antibodies could be divided into 2 classes, those that bound only IL-12R positive human cells and those that bound to most human cells (data not shown). Representative antibodies from each class, 2-4E6 and 2C6, respectively, were produced in ascites fluid, purified by protein G affinity chromatography and extensively characterized.

For FIG. 8, PHA-activated PBMC (PHA-PBMC), Kit-225 (Kit-225) and K6 (K6) cells (1×10⁷ cells/ml) were incubated with $^{125}$I-IL-12 (100–500 pM) for 2 hrs at room temperature in the absence or presence of 25 nM unlabeled IL-12. Cells were then washed, affinity crosslinked with BS3 (0.4 mM final concentration) and a cell extract prepared as described. The cell extract was precipitated with wheat germ lectin bound to solid supports as described. The precipitated proteins were released by treatment with sample buffer and analyzed by SDS-PAGE and autoradiography on a 8.0% slab gel. The complex of $^{125}$I-IL-12 crosslinked to the IL-12 receptor migrates as a single major band of approximately 210–250 KDa. The band migrating at 75 KDa is $^{125}$I-IL- 12 that was bound but not crosslinked to the IL-12 receptor. $^{125}$I-IL- 12 (IL-12)and $^{125}$I-IL-12 that was treated with the BS3 crosslinker (IL-12/BS3) were electrophoresed in parallel lanes as markers for the migration of the 75 KDa IL-12 heterodimer and for any oligomers of IL- 12 that may form with the BS3 crosslinker. The molecular sizes indicated in the margins were estimated from standards run in parallel lanes. Exposure time was 7 days.

TABLE 1

INITIAL IDENTIFICATION OF HYBRIDOMAS SECRETING ANTI-IL-12 RECEPTOR ANTIBODIES: SPLENOCYTES FROM MICE #211-1 AND #211-2

| | HYBRIDOMA/ANTIBODY | I.P. ASSAY[1] | INHIBITION ASSAY[2] |
|---|---|---|---|
| | | (cpm bound) | |
| 211-1 | IL-12R 2C6[3] | 1900 | − |
| | IA5 | 722 | − |
| | 4E6 | 840 | − |
| | 5C1 | 312 | + |
| 211-2 | 3B1 | 1323 | − |
| | 4A3 | 2172 | − |
| | 4D6 | 804 | − |
| | 5D5 | 877 | − |

TABLE 1-continued

INITIAL IDENTIFICATION OF HYBRIDOMAS
SECRETING ANTI-IL-12 RECEPTOR ANTIBODIES:
SPLENOCYTES FROM MICE #211-1 AND #211-2

| HYBRIDOMA/ANTIBODY | I.P. ASSAY[1] | INHIBITION ASSAY[2] |
|---|---|---|
| | (cpm bound) | |
| 4A5 | 509 | + |
| 4C6 | 456 | + |
| 1D1 | 1395 | − |
| 5E6 | 2043 | − |
| 2-4E6 | 2836 | − |
| Control mAb | 402 | − |

[1]I.P. assay measures the amount of $^{125}$I-IL-12/IL-12R complex bound by the immobilized antibody.
[2]Inhibition assay measures whether the antibody can inhibit $^{125}$I-IL-12 binding to PHA-activated PBMC.
[3]IL-12R 2C6 is an antibody that both immunoprecipitates the $^{125}$I-IL-12/IL-12R complex and binds to many IL-12 positive and negative human cells. This antibody probably recognizes a component closely associated with the IL-12R.

EXAMPLE 14

Characteristics of Monoclonal Anti-IL-12R Antibody 2-4E6 Binding to Natural IL-12R mAb 2-4E6 immunoprecipitates the $^{125}$I-IL-12/IL-12R complex solubilized from PHA-activated human lymphoblasts, Kit-225 and K6 cells (FIG. 9, data shown for PHA-activated PBMC), but does not block $^{125}$I-IL-12 binding to IL-12R expressed on these cells. These data suggested that the 2-4E6 antibody was a non-inhibitory or nonneutralizing anti-IL-12R antibody. To confirm that 2-4E6 was a noninhibitory antibody specific for the IL-12R, 2-4E6 was labeled with $^{125}$I and direct binding assays were performed with IL-12R positive and negative cells. $^{125}$I-2-4E6 binds to IL-12R bearing cells with an affinity that ranges from 337 pM to 904 pM and identifies between 1500 and 5000 binding sites per cell (PHA-activated PBMC, FIG. 10; K6 cells, FIG. 11). IL-12 does not block $^{125}$I-2-4E6 from binding to PHA-activated PBMCs and confirms that 2-4E6 is a non-inhibitory/nonneutralizing antibody (FIG. 12). $^{125}$I-2-4E6 binds to other cells expressing IL-12R, such as Kit 225, and YT cells, but does not bind to IL-12R negative cells (non-activated human PBMC, MRC-5 fibroblasts and HL-60 cells (Table 2).

Figure 13B:
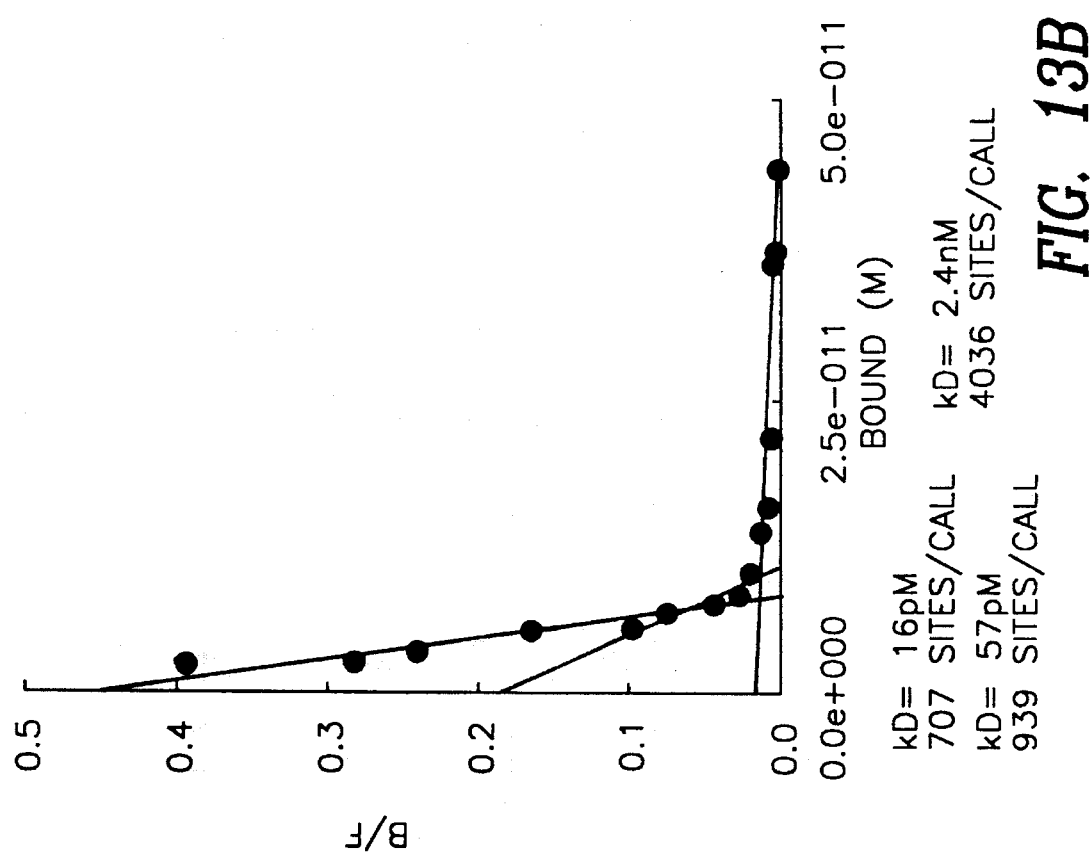
FIG. 13: Equilibrium Binding of $^{125}$I-IL-12 to Human K6 Cells at Room Temperature
Figure 13A:
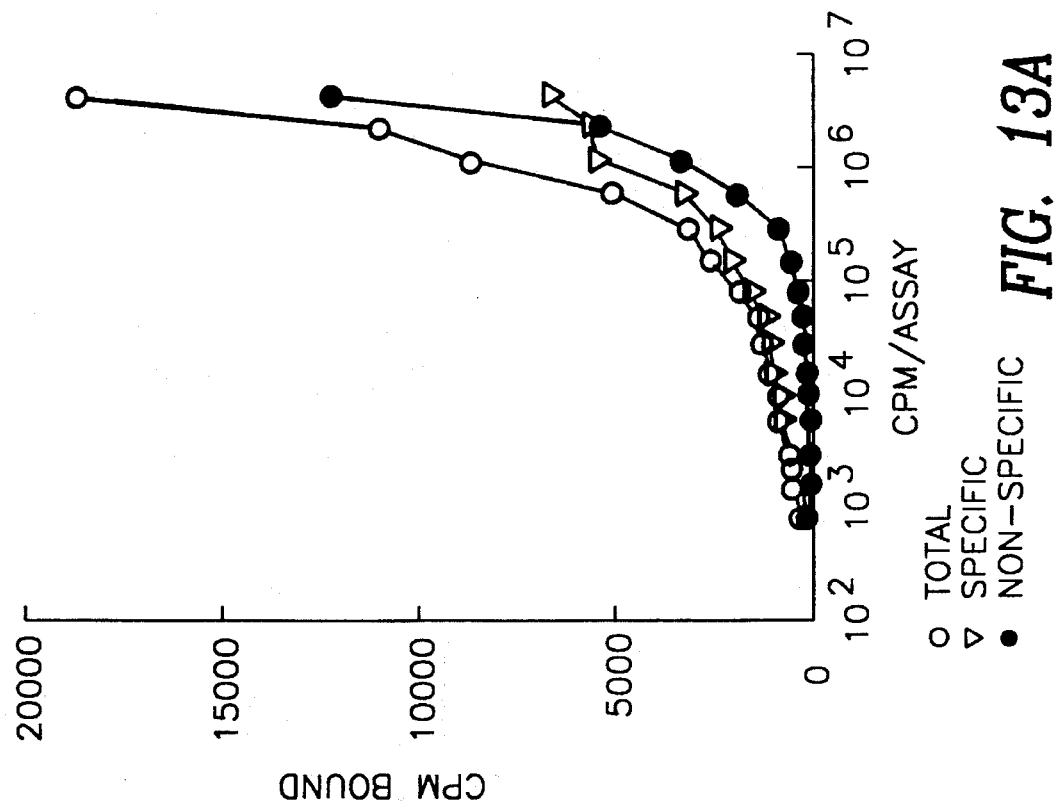

Equilibrium binding assays have demonstrated that $^{125}$I-IL-12 identifies 3 separate binding sites on the surface of PHA-activated PBMCs, Kit-225 and K6 cells (FIG. 13, data for K6 cells and Table 2). Analysis of this binding data by the method of Scatchard shows these affinities are approximately 5–20 pM, 50–200 pM and 2–6 nM, respectively. The total number of $^{125}$I-IL-12 binding sites per cell are approximately 1500 to 5000, which is in good agreement with the total number of binding sites identified by $^{125}$I-2-4E6 (Table 2). The data also suggests that 2-4E6 recognizes the low affinity (2–5 nM) binding component of the IL-12 receptor in much the same manner that the anti-TAC antibody recognizes the low affinity component (p55 subunit) of the IL-2 receptor.

Figure 14B:
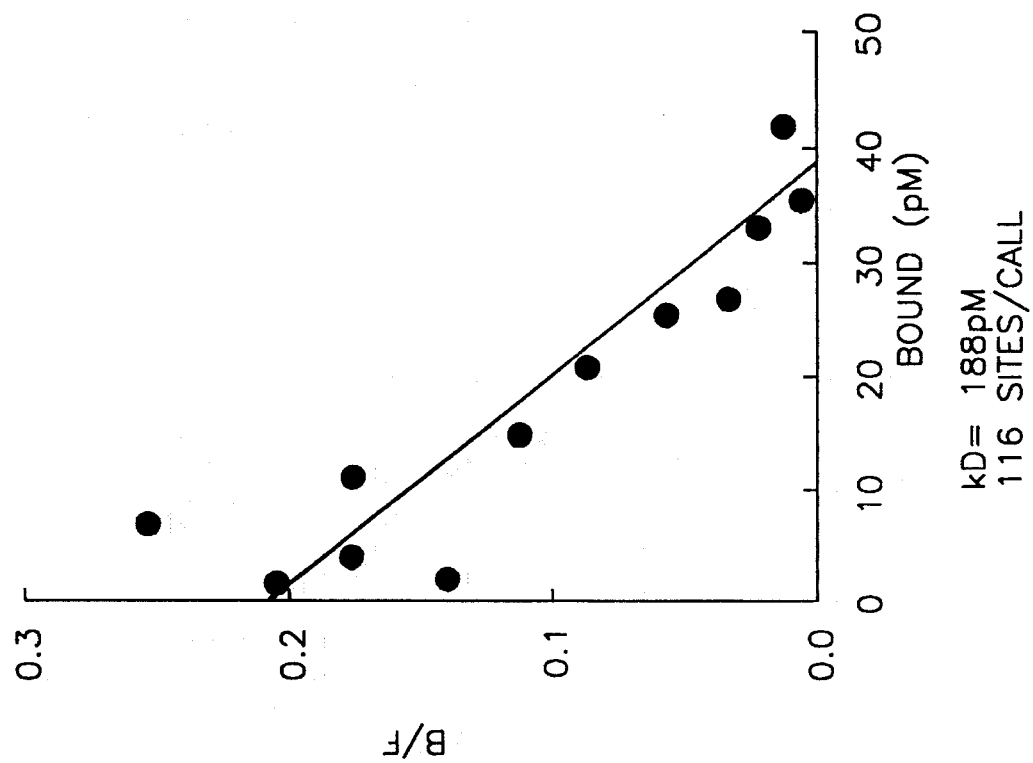
FIG. 14: Equilibrium Binding of $^{125}$I-IL-12 to Detergent Solubilized IL-12R from K6 Cells
Figure 14A:
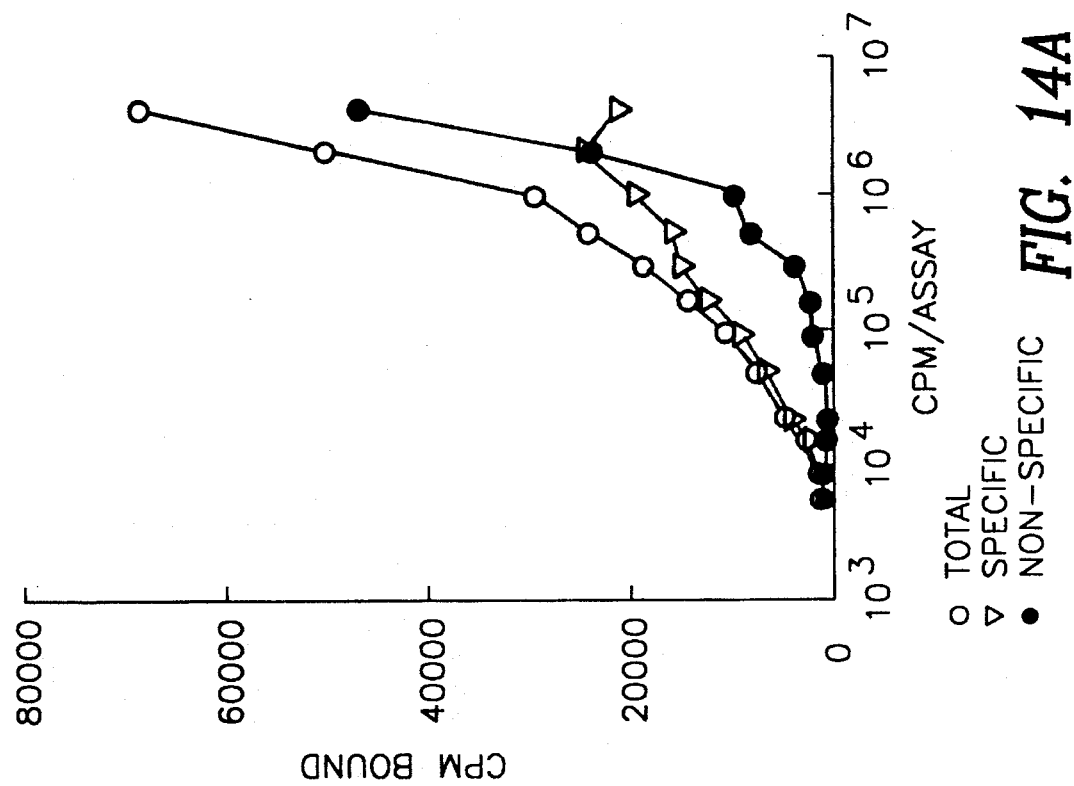
Figure 15:
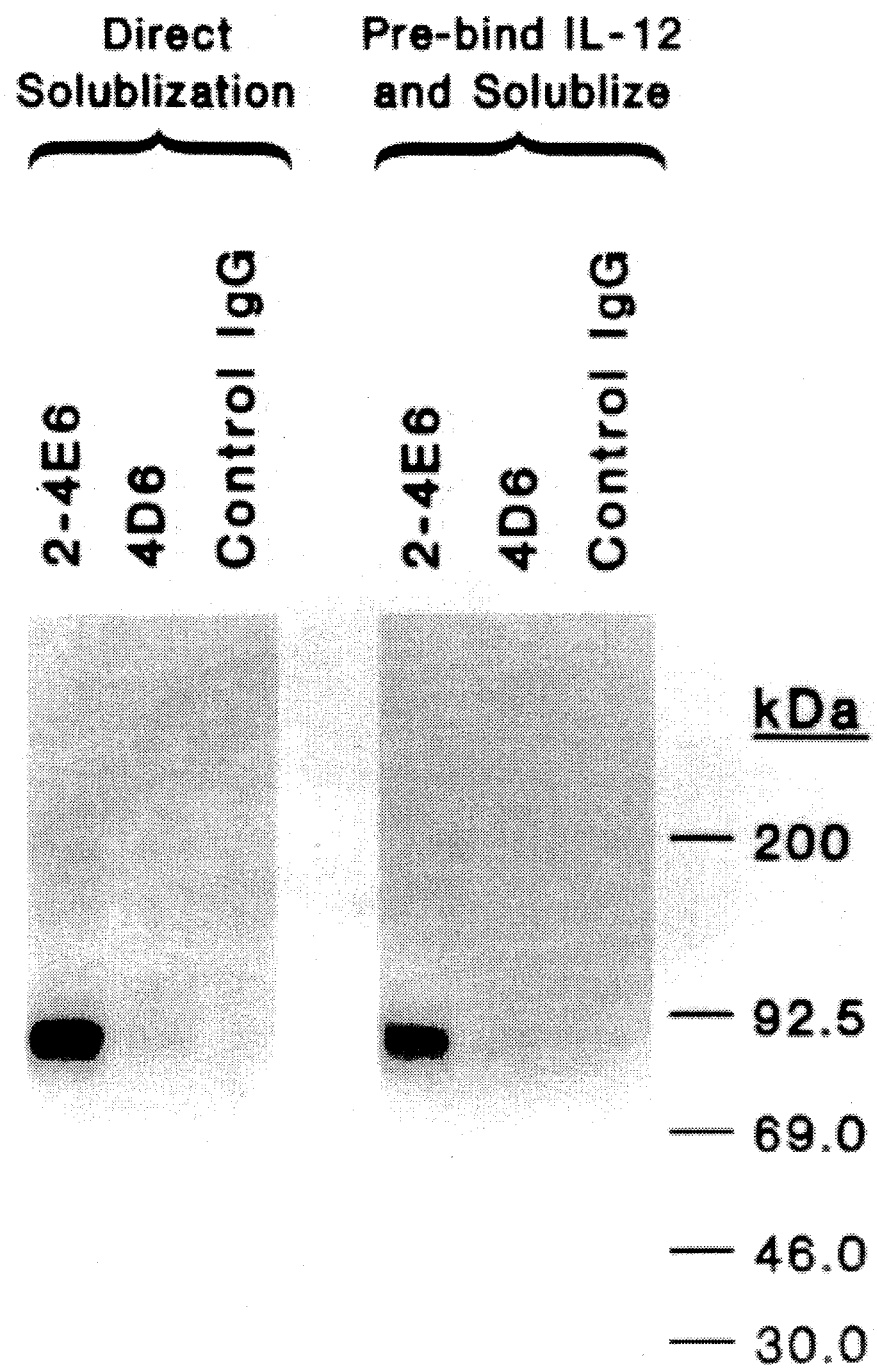
FIG. 15: Western Blot Analysis of Detergent Solubilized IL-12R with mAb 2-4E6

Since the data indicated that mAb 2-4E6 was a non-neutralizing antibody specific for the IL-12R, the molecular weight and $^{125}$I-IL-12 binding characteristics of the protein(s) immunoprecipitated by mAb 2-4E6 from the surface of IL-12R positive cells was investigated. The steady state binding of $^{125}$I-IL-12 to proteins immunoprecipitated by immobilized 2-4E6 from solubilized extracts of PHA-activated PBMCs, Kit-225 and K6 cells was saturable and specific (FIG. 14, data for extracts from K6 cells). Transformation of the binding data by the method of Scatchard revealed a single site with an apparent affinity of 188 pM. The proteins immunoprecipitated by 2-4E6 from the cell extracts were resolved by SDS-PAGE, transferred to nitrocellulose membrane and probed with $^{125}$I-2-4E6 in a western blot. On the western blot, $^{125}$I-2-4E6 binds to an approximately 90 KDa protein, that is only immunoprecipitated by 2-4E6 and not by an anti-IL-12 antibody or a control antibody (FIG. 15, data shown for PHA-activated PBMCs). In summary, all the data demonstrated that mAb 2-4E6 bound a protein on the surface of IL-12R positive cells that was approximately 90 KDa and bound $^{125}$I-IL-12 in a specific manner.

For FIG. 9, soluble complexes of $^{125}$I-IL-12/IL-12R were prepared from PHA-activated human PBMC as detailed herein (see also FIG. 8) and immunoprecipitated by immobilized antibodies, 2-4E6, 2C6, 4D6, 20C2 and control. The soluble complexes were also precipitated with wheat germ lectin immobilized on crosslinked agarose. The precipitated proteins were analyzed as described herein and in FIG. 8. Antibodies 4D6 and 20C2 are non-neutralizing and neutralizing anti-IL-12 antibodies, respectively. 4D6 immunoprecipitates $^{125}$I-IL-12/IL-12R complex and free $^{125}$I-IL-12, whereas 20C2 only immunoprecipitates free $^{125}$I-IL-12. Both 2-4E6 and 2C6 recognize the $^{125}$I-IL-12/IL-12R complex. $^{125}$I-IL-12 (IL-12) and $^{125}$I-IL-12 that was treated with the BS3 crosslinked (IL-12/BS3) were electrophoresed in parallel lanes as markers for the migration of the 75 KDa IL-12 heterodimer and for any oligomers of IL-12 that may form with the BS3 crosslinker. The molecular sizes indicated in the margins were estimated from standards run in parallel lanes. Exposure time was 7 days.

For FIG. 10, Lymphoblasts (1×10$^6$ cells) were incubated for 2 hrs at room temperature with increasing concentrations of $^{125}$I-2-4E6 in the absence (○) or presence (●) of 25 nM unlabeled 2-4E6. Total (○) and non-specific (●) cell bound radioactivity were determined as described. Specific binding of $^{125}$I-2-4E6 (▼) was calculated by subtracting non-specific binding from total binding. The right hand panel shows analysis of the binding data according to the method of Scatchard as determined by LIGAND with a single-site model.

Figures 11A, 11B:
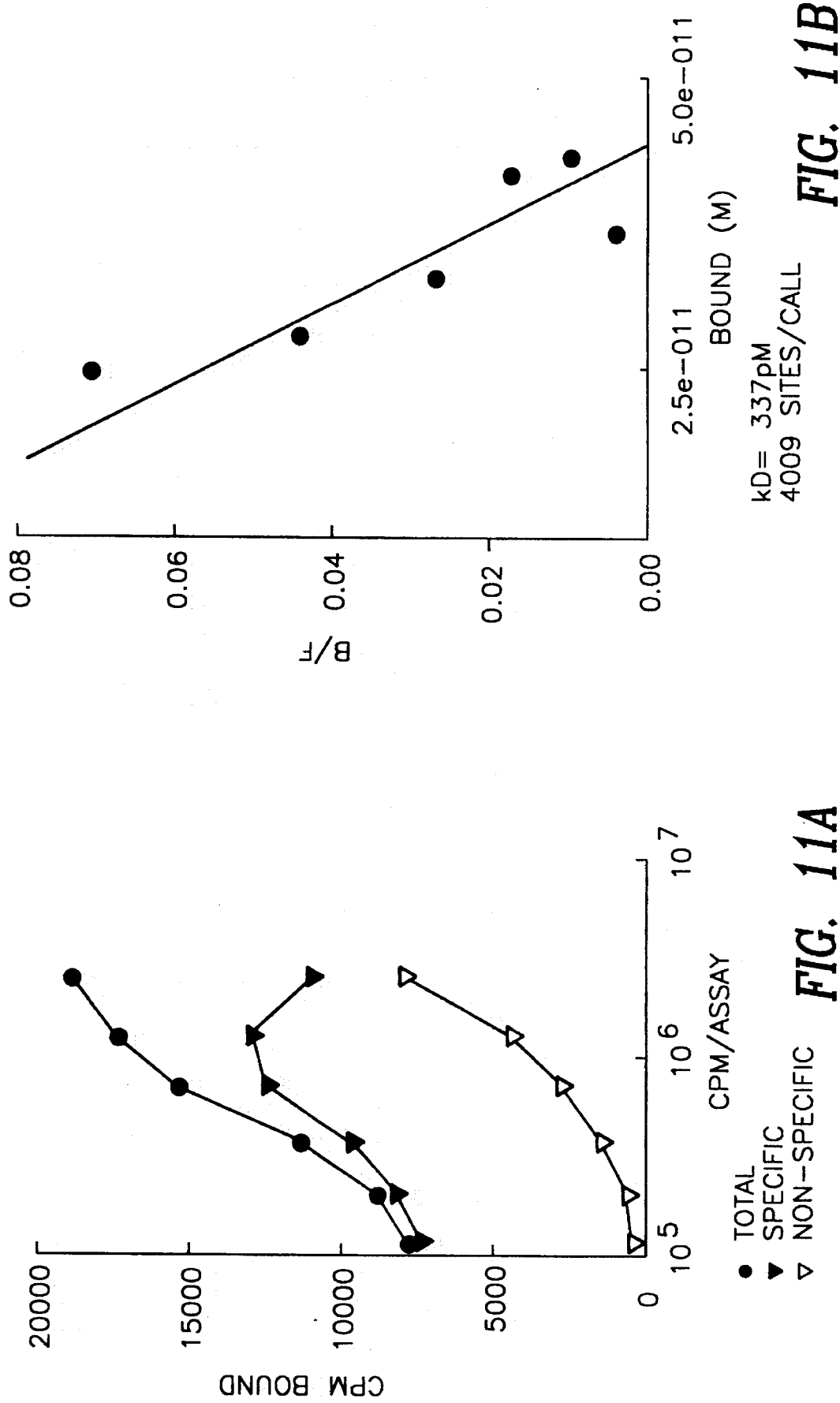
FIG. 11: Equilibrium Binding of $^{125}$I-2-4E6 to Human K6 Cells at Room Temperature
Figure 12:
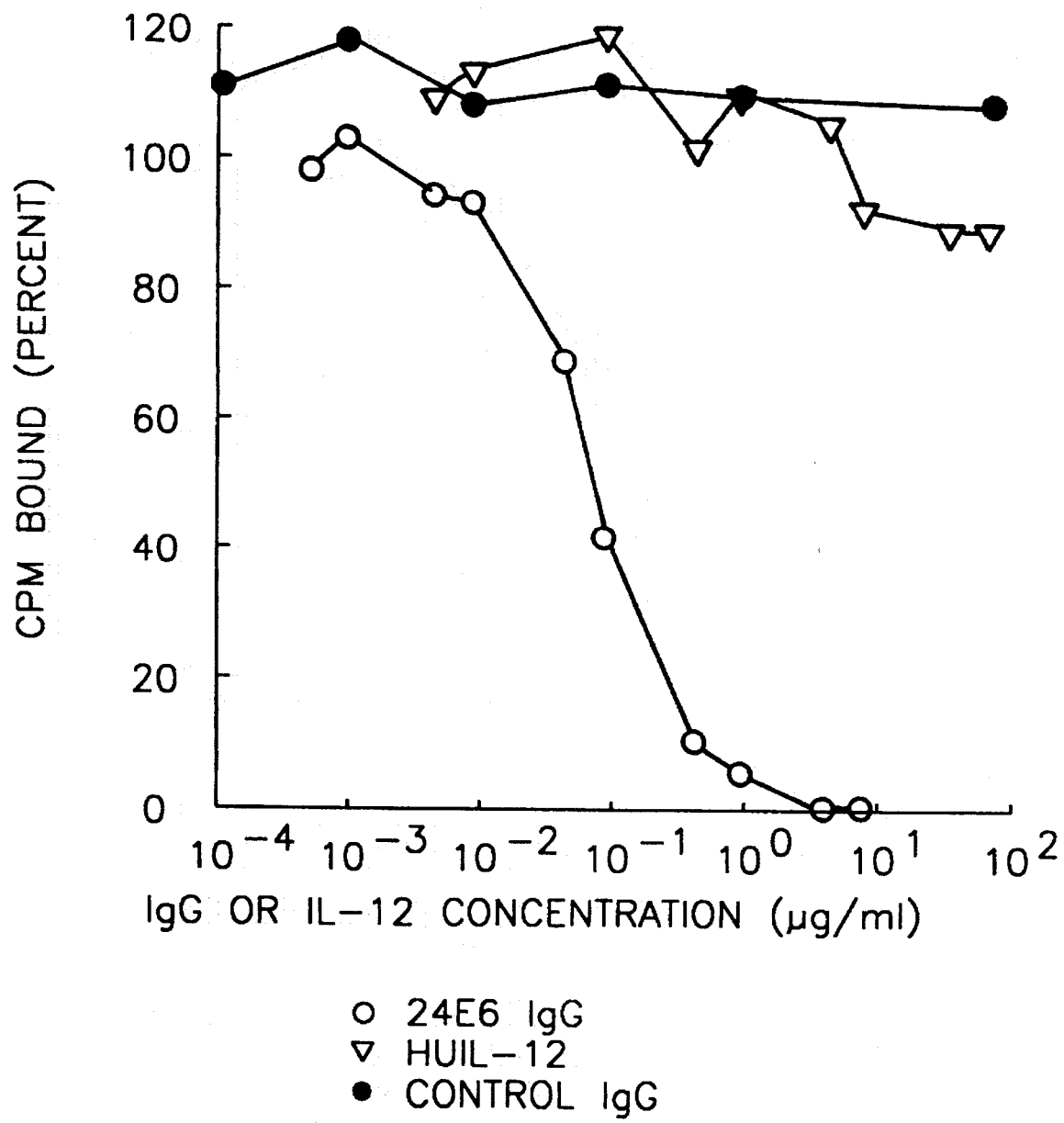
FIG. 12: Inhibition of $^{125}$I-2-4E Binding to K6 Cells by Purified 2-4E6 (24E6), Human IL-12 (HUIL-12) and Control Antibody (Control IgG)

For FIG. 11, K6 cells (1×10$^6$ cells) were incubated for 2 hrs at room temperature with increasing concentrations of $^{125}$I-2-4E6 in the absence (●) or presence (▽) of 25 nM unlabeled 2-4E6. Total (●) and non-specific (▽) cell bound radioactivity were determined as described. Specific binding of $^{125}$I-2-4E6 (▼) was calculated by subtracting non-specific binding from total binding. The right hand panel shows analysis of the binding data according to the method of Scatchard as determined by LIGAND with a single-site model.

For FIG. 12, The data are expressed as the amount of $^{125}$I-2E 6 bound [CPM BOUND (Percent)] to the cells in the presence of the indicated concentrations of unlabeled antibody or IL-12 when compared with the total specific binding in the absence of unlabeled competitor.

For FIG. 13, K6 cells (1×10$^6$ cells) were incubated for 2 hrs at room temperature with increasing concentrations of $^{125}$I-IL-12 in the absence (○) or presence (●) of 50 nM unlabeled IL-12. Total (○) and non-specific (●) cell bound radioactivity were determined as described. Specific binding of $^{125}$I-IL-12 (▽) was calculated by subtracting non-specific binding from total binding. The right hand panel shows analysis of the binding data according to the method of Scatchard as determined by LIGAND with a single-site model.

For FIG. 14, K6 cells (1.5×10⁸ cells/ml) were solubilized with 8 mM CHAPS extraction buffer and the cell extract (0.2 ml) was immunoprecipitated for 16 hrs at 4° C. with mAb 2-4E6 immobilized on goat anti-mouse IgG coupled to agarose as described. Following this incubation, the beads were pelleted, washed and resuspended in IP buffer containing $^{125}$I-IL-12 at concentrations ranging from 7 pM to 7.5 nM. The IL-12R immobilized on the 2-4E6 coated beads was incubated with $^{125}$I-IL-12 for 2 hrs at RT and IL-12R bound radioactivity was determined in the presence of 50 nM unlabeled IL-12. The right hand panels show analysis of the binding data according to the method of Scatchard as determined by LIGAND with a single-site model.

For FIG. 15, PHA-activated PBMC (1×10⁸ cells/ml) were solubilized with 8 mM CHAPS extraction buffer and the cell extract (1 ml) was immunoprecipitated as described in FIG. 14. Following this incubation, the beads were pelleted, washed and the bound proteins released by treatment with 0.1 M glycine pH 2.3. The released proteins were separated by non-reducing SDS/PAGE on 8% gels transferred to nitrocellulose membrane and probed with $^{125}$I-2-4E6 as described. The molecular sizes indicated in the margins were estimated from molecular weight standards (Amersham Prestained High Molecular Weight Standards) run in parallel lanes. Exposure time was 7 days.

TABLE 2

COMPARISON OF THE BINDING OF IL-12 AND 2-4C6 TO HUMAN CELLS EXPRESSING IL-12 RECEPTOR

| CELL TYPE | IL-12 BINDING[1] | | 2-4E6 BINDING[2] | |
|---|---|---|---|---|
| | KD (nM) | Sites/cell | KD (nM) | Sites/cell |
| Human Cells | | | | |
| non-activated human PBMC[3] | none detected | | none detected | |
| PHA-PBMC (5–7 days) (3 sites) | 0.018 0.084 1.800 | 312 501 1406 | 0.745 | 1472–2246 |
| K6 cells (3 sites) | 0.016 0.057 2.400 | 707 939 4036 | 0.489 | 3116–5259 |
| Kit-225 (3 sites) | 0.023 0.210 2.360 | 100 250 755 | 0.594 | 1950 |
| YT cells (2 sites) | 0.006 0.109 | 24 117 | 0.904 | 4522 |
| RAJI cells | none detectable | | 0.450 | 561 |
| MRC-5 | none detectable | | none detectable | |
| HL-60 | none detectable | | none detectable | |

[1]Steady state $^{125}$I-IL-12 binding assays. Apparent dissociation constant ($K_D$) and binding sites per cell have been calculated by transformation of the data by the method of Scatchard.
[2]Steady state $^{125}$I-2-4E6 binding assays. Data transformed by the method of Scatchard.
[3]Human peripheral blood mononuclear cells (PBMC) were activated with PHA as described in the methods (PHA-PBMC).

EXAMPLE 15 mAb 2-4E6 Binding To Human Recombinant IL-12R Expressed in COS Cells

Figure 4A:
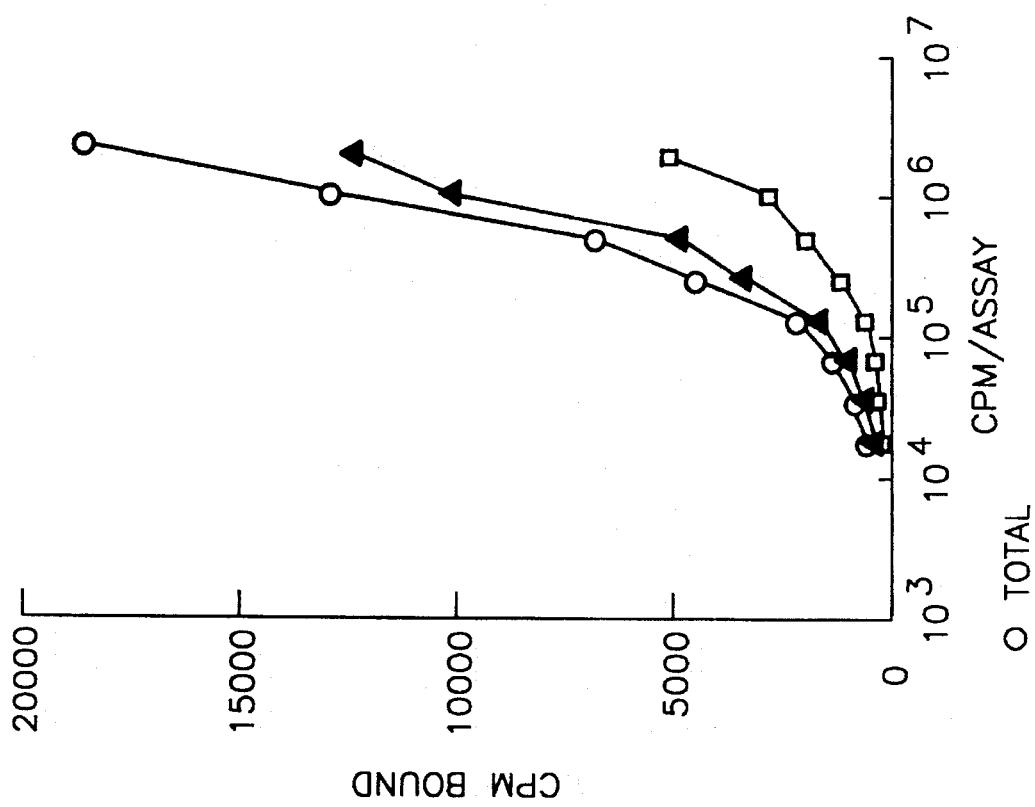
FIG. 4A: Scatchard analysis of IL-12 binding to recombinant human IL-12 receptor expressed in COS cells.
Figure 4D:
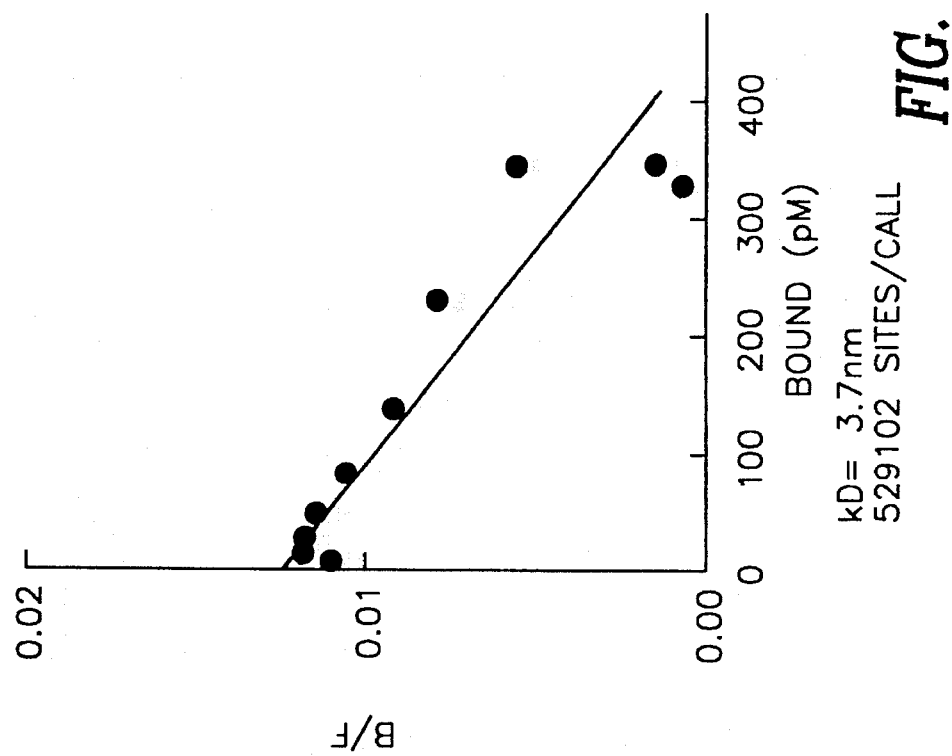
Figure 4C:
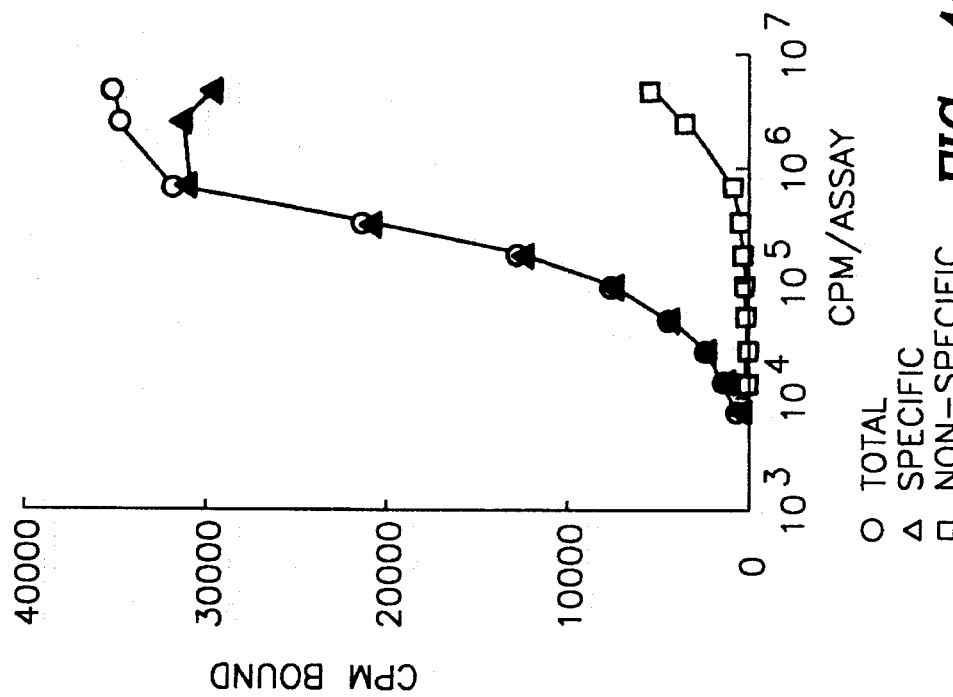

The characteristics of the protein bound by mAb 2-4E6 fulfilled standard criterion for an IL-12R and therefore 2-4E6 was used in an expression cloning strategy to isolate a eDNA coding for the human IL-12R. A eDNA coding for the human IL-12R was isolated by this method (U. Gubler and A. O. Chua, unpublished observations). The IL-12R eDNA was engineered in a mammalian cell expression vector, transfected into COS-7 cells and the specificity for binding of $^{125}$I-IL-12 and $^{125}$I-2-4E6 was determined. Steady state binding of $^{125}$I-IL-12 to the rIL-12R expressing COS cells identifies a single binding site with an apparent affinity of 2–6 nM and approximately 150,000 sites/cell (FIG. 4A). This low affinity IL-12 binding site corresponds to the low affinity site seen in the binding assays with human cells that naturally express IL-12R. The binding of $^{125}$I-2-4E6 to rIL-12R expressed in the COS cells is saturable and specific and identifies approximately 500,000 sites/cell (FIG. 4B). COS cells transfected with an unrelated plasmid do not bind either $^{125}$I-IL-12 or $^{125}$I-2-4E6 (data not shown). These data demonstrated unequivocally that mAb 2-4E6 was specific for the low affinity component of the IL-12R.

For FIG. 4A, COS cells were transfected with a plasmid expressing human rIL-12R as described. Three days later, transfected cells (1×10⁴ cells) were incubated for 2 hrs at room temperature with increasing concentration of $^{125}$I-IL-12 in the absence (O) or presence (□) of 50 nM unlabeled IL-12. Total (O) and non-specific (□) cell bound radioactivity were determined as described. Specific binding of $^{125}$I-IL-12 (▲) was calculated by subtracting non-specific binding from total binding. The right hand panel shows analysis of the binding data according to the method of Scatchard as determined by LIGAND with a single-site model.

For FIG. 4B, COS cells were transfected with a plasmid expressing human rIL-12R as described in Methods. Three days later, transfected cells (1×10⁴ cells) were incubated for 2 hrs at room temperature with increasing concentrations of $^{125}$I-2-4E6 in the absence (O) or presence (□) of 50 nM unlabeled 2-4E6. Total (O) and non-specific (□) cell bound radioactivity were determined as described. Specific binding of $^{125}$I-2-4E6 (▲) was calculated by subtracting non-specific binding from total binding. The right hand panel shows analysis of the binding data according to the method of Scatchard as determined by LIGAND with a single-site model.

EXAMPLE 16

Analysis of mAb 2-4E6 Binding to IL-12R Positive Human Cells by Fluorescence Activated Cell Sorting (FACS)

Figure 16A:
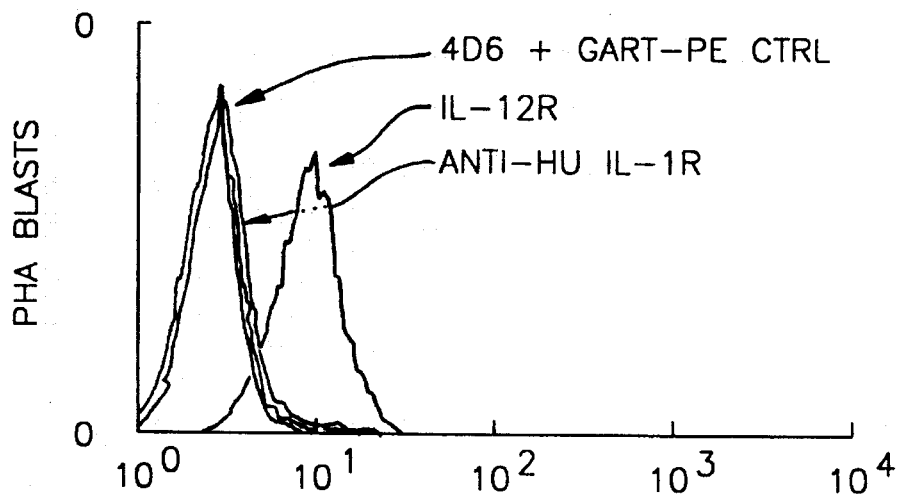
FIG. 16: Detection of IL-12 Receptor on Human Cells by Flow Cytometry
Figure 16B:
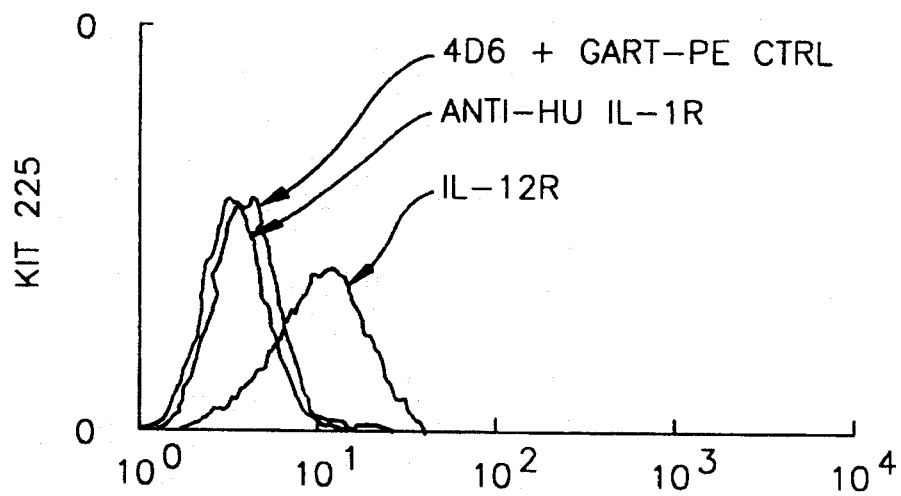
Figure 16C:
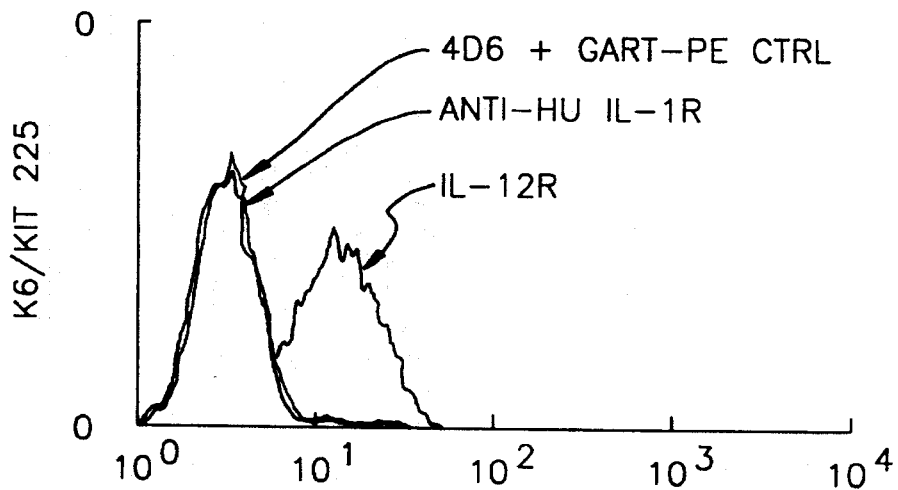

The expression level of IL-12R on human cells could be regulated depending on the activation state of the cells, the cell cycle or the type of environment from which the cells are isolated. Previous data had demonstrated that PHA activation of PBMC leads to a gradual rise in IL- 12R expression, reaching a maximum at 3–4 days after activation and declining thereafter. Desai et al., J. Immunol., 148:3125 (1992). To investigate the heterogeneity of IL-12R expression on PHA-activated PBMCs, Kit-225 and K̃6 cells, FACS analysis of IL-12R on these cells was determined with mAb 2-4E6 (FIG. 16). The fluorescence intensity of binding of 2-4E6 was specific and indicated that these three cell types expressed approximately equal numbers of IL-12R. Interestingly, the FACS analysis indicated that the cell population was fairly homogenous and did not have one population expressing no or low numbers of IL- 12R and a second population that expressed very high numbers of IL- 12R.

For FIG. 16, Day 4 PHA-activated lymphoblasts, Kit-225 and K6 cells were analyzed for IL-12R expressing cells by the indirect fluorescent antibody-labeling technique described. The figure depicts specific staining for IL-12R obtained in the presence of mAb 2-4E6 (IL-12R) and non-specific staining obtained in the presence of a control antibody specific for IL-1 receptor (anti-Hu IL-1R), a control antibody specific for human IL-12 (4D6 +GART-PE CTRL) and the goat anti-mouse antibody conjugated with PE (GART-PE CTRL).

Cell Culture

Peripheral blood mononuclear cells (PBMC) were isolated from blood collected from healthy donors. The blood was collected into heparinized syringes, diluted with an equal volume of Hank's balanced salt solution (HBSS) and layered over Ficoll-Hypaque. The tubes were spun at 2000 rpm for 20 minutes at room temperature. PBMC at the interface were collected and pelleted at 1500 rpm for 10 minutes through a 15 ml cushion of 20% sucrose in PBS. Pelleted PBMC were resuspended in tissue culture medium and washed twice in the same medium (RPMI 1640 plus 5% serum). Finally, the cells were cultured at $0.5-1\times10^6$ cells/ml in tissue culture medium plus 1 μg/ml PHA-P (Difco) for 3 days at 37 degrees C. in a 5% $CO_2$ atmosphere. Cells were split 1:1 in culture medium plus 50 U/ml rhuIL-2 (Hoffmann-La Roche Inc.) to yield >95% T-cells. The next day, these cells were used for assessing their responsiveness to IL-12, for radioligand (IL-12) binding assays and in flow cytometry assays for the detection of IL-12 receptors.

Flow cytometric detection of IL-12 receptors on such 4 day activated PHA blasts was performed as follows: the cells were washed twice in PBS and resuspended at $2\times10^6$ cells/ml in PBS plus 2% fetal calf serum and 0.1% sodium azide. All the subsequent steps were carried out at 4 degrees C. $1\times10^6$ cells were incubated in 1 nM human IL-12 for 40 minutes. The cells were washed in FACS buffer and incubated with about 1 μg of biotinylated rat anti human p40 IL-12 subunit antibody 4D6 for 20 minutes. Cells were washed again and resuspended in 100 μl of a 5 μg/ml streptavidin-phycoerythritin conjugate (Fisher Biotech) for 15 minutes. The cells were then washed again before analysis on a FACScan flow cytometer (Becton Dickinson).

Extraction and characterization of RNA

PHA activated cells as described above were harvested at day 2–3 and total RNA was extracted using GuanidinIsothiocyanate/Phenol as described (P. Chomczynski and N. Sacchi, Anal. Biochem., 162:156, 1987). Poly A+RNA was isolated from the total RNA by one batch adsorption to oligo dT latex beads as described (K. Kuribayashi et al., Nucl. Acids Res. Symposium Series 19:61, 1988). The mass yield of this purification was about 4%.

RNA blots were performed as follows. RNA was fractionated in 1.2 agarose gels under denaturing conditions in the presence of 2.2.M formaldehyde and subsequently transferred to nitrocellulose as described (Molecular Cloning, a Laboratory Manual, second edition, J. Sambrook, E. F. Fritsch, T. Maniatis, Cold Spring Harbor Laboratory Press 1989 (hereinafter "Molecular Cloning Manual")). The RNA blots were hybridized ($7\times10^5$ cpm/ml, 30 ml) with labeled probe in 5×SSC (1×SSC =0.15 M NaCl–0.015 M NaCitrate)–50% formamide–5×Denhardts solution (1×Denhardts=0.02% polyvinylpyrrolidone, 0.02% Ficoll 400, 0.02% bovine serum albumin fraction V) –0.3% SDS–250 μg/ml denatured salmon sperm carrier DNA at 37° C. overnight. The probe was generated by random-primer labeling gel-isolated insert from IL-12 receptor cDNA clone No.5 by the method as described in Molecular Cloning Manual. The blots were first quickly rinsed at room temperature in 2×SSC, then washed in 0.1×SSC at 50° C. for 30 minutes, dried and exposed to Kodak XAR film at −70° C. for 3 days.

cDNA library

From the above polyA+ RNA, a cDNA library was established in the mammalian expression vector pEF-BOS as follows: 3 μg of polyA+RNA were reverse transcribed into single stranded cDNA using RNaseH minus reverse transcriptase (GIBCO BRL Life Technologies Inc., P.O. Box 9418, Gaithersburg, Md. 20898). The resulting mRNA-cDNA hybrids were converted into blunt ended doublestranded cDNAs by established procedures (U. Gubler and A. Chua, in: Essential Molecular Biology Volume II, T. A. Brown, editor, pp. 39–56, IRL Press 1991). BstXI linkers (A. Aruffo and B. Seed, Proc. Natl. Acad. Sci (USA) 84, 8573, 1987) were ligated to the resulting cDNAs and cDNA molecules >800 base pairs (bp) were selected over a Sephacryl SF 500 column. A Sephacryl SF 500 column (0.8×29 cm) was packed by gravity in 10 mM Tris-HCl pH 7.8–1 mM EDTA–100 mM NaAcetate. BstXI linked cDNA was applied to the column and 0.5 ml fractions were collected. A small aliquot of each fraction was run on a 1% agarose gel, the gel was dried down and the size distribution of the radioactive cDNA visualized by exposure of the gel to X-ray film. cDNA molecules larger than 800 bp were selected in this fashion, pooled, concentrated by ethanol precipitation and subsequently ligated to the cloning vector. The cloning vector was the plasmid pEF-BOS that had been cut with BstXI and purified over two consecutive gels. 300 ng of plasmid DNA were ligated to 30 ng of size selected cDNA from above in 60 μl of ligation buffer (50 mM Tris-HCl pH 7.8–10 mM $MgCl_2$–10 mM DTT–1 mM rATP –25 μg/ml bovine serum albumin) at 15° C. overnight. The following day, the ligation reaction was extracted with phenol, 6 μg of mussel glycogen were added, and the nucleic acids were precipitated by ethanol. The precipitate was dissolved in water and the precipitation was repeated, followed by a wash with 80% ethanol. Finally, the pellet was dissolved in 6 μl of water and 1 ml aliquots were subsequently electroporated into E. coli strain DH-10B (BRL). By electroporating 5 parallel aliquots in this fashion, a library of about 10 million recombinants was generated for future use.

Screening for IL-12 receptor cDNAs by panning

The basic principle of the panning method has been described in A. Aruffo and B. Seed, Proc. Natl. Acad. Sci (USA) 84, 8573, 1987 as discussed below. Ten library aliquots each representing about 50,000 clones were plated on LB amp plates and were grown up overnight. The next day, the colonies from each pool were scraped off into a separate 50 ml aliquot of LB +amp and the cultures were grown for another two hours before plasmid DNA was extracted using QIAGEN plasmid kits. The ten separate DNA pools were then transfected into COS cells, using the DEAE dextran technique (2 million COS cells/9 cm diameter plate and 2.5 μg DNA)(Molecular Cloning Manual). 2 to 3 days later, the COS cells were detached from the plates using 0.5 mM EDTA/0.02% Na Azide in PBS and a single cell suspension was prepared for each pool. The monoclonal anti IL-12 receptor antibody 2-4E6 as discussed above was subsequently bound to the cells in suspension (10 μg/ml in PBS-0.5 mM EDTA-0.02% Na Azide-5% FCS, 1 hour, on ice). The cell suspension was then spun through a layer of 2% Ficoll in the above buffer (tabletop centrifuge, 1000 rpm, 4 minutes) to eliminate the excess unbound antibody and the cells were gently resuspended in the same buffer. The cells from one pool were subsequently added to one bacterial petri dish (9 cm diameter) that had been coated with polyclonal goat anti mouse IgG (20 μg/ml in 50 mM Tris-HCl pH 9.5, RT/OVERNIGHT(ON)) and blocked with 1% BSA in PBS (37 degree C./1 hour). COS cells were panned in this way for 2 hours at RT. Nonadhering cells were then gently washed off with PBS and the remaining adherent cells in the dishes lysed by the addition of 0.8 ml of Hirt lysis solution (0.6% SDS-10 mM EDTA). After transferring to Eppendorf tubes, the lysates were made 1 M NaCl, incubated ON at +4 degrees C. and then spun at 15,000 rpm for 10 minutes in the cold. The supernatants were extracted with phenol once, 12 μg of mussel glycogen was added and the DNA precipitated twice by adding 0.5 volumes of 7.5 M $NH_4OAc$ and 2.5 volumes of ethanol. The resulting DNA pellet was washed once with 80% ethanol, dried and taken up in 1 μl of distilled $H_2O$. The entire prep was then electroporated into *E. coli* strain DH- 10B and the resulting colonies grown up ON. This represents one panning cycle. The ten library aliquots were panned each one separately for a total of three cycles.

From the last cycle of each pool, DNA was again extracted and this time transfected into COS cells plated on plastic one-chamber microscopic slides (2 slides per pool). 2–3 days after transfection, to one of the slides was bound labeled human IL-12 ($10^6$ cpm/ml=300 pM in RPMI 1640 plus 5% FCS for 2–3 hours at 4 degrees C.) and to the other slide labeled monoclonal Ab 2-4E6 ($2\times10^6$ cpm/ml=1 nM in RPMI 1640 plus 5% FCS for 1 hour at RT). The slides were washed in PBS, fixed for 40 seconds in a cold mixture of methanol:acetone (7:3) and air dried. The slides were subsequently dipped in Kodak photographic emulsion NTB2, air dried and exposed in a light-tight container for 2–4 days at 4 degrees C. They were developed in Kodak D10 developer according to the manufacturer's instructions and evaluated under a light microscope using a 10 to 40 fold bright field magnification. One of the ten pools, number 5, showed a large number of positive cells both for IL-12 and 2-4E6 binding. *E. coli* clones from this 3× panned pool were subsequently picked into a microtiterplate (3 clones per well for a total of 288 clones). Pools representing the 8 rows and 12 columns from this plate were grown up and their plasmid DNA extracted. These 20 preps were transfected separately into COS cells on 12 well plates ($10^5$ cells well, 4 wells per pool). 2–3 days after the transfection, labeled IL-12 was bound to the cells in two wells (total binding), whereas the other two wells per pool received labeled IL-12 and a 100 fold molar excess of cold IL-12 (=nonspecific binding). Wells were washed and the bound radioactivity eluted with 0.5 ml of 1% SDS and counted in a gamma counter. Two positive pools were identified in this manner, one representing column 1 and the other one representing row F from the microtiterplate. *E. coli* clones from well F1 must thus contain the IL-12 binding activity. Clones from that well were plated, and DNA from 10 single colonies was analyzed for plasmid insert size. 3 out of the 10 colonies showed an insert of about 2.1 kilobases in length, large enough to encode the IL-12 receptor. One of these clones was picked for further analysis.

Characterization of IL-12 receptor cDNAs

IL-12 receptor clone No. 5 was picked as described above and the plasmid DNA isolated. Gel isolated insert was sequenced on both strands using the ABI automated DNA sequencer in conjunction with a thermostable DNA polymerase and dye-labeled dideoxynucleotides as terminators.

Sequence alignments were run using the ALIGN program (M. 0. Dayhoff et al., Methods Enzymology 91,524,1983) with the mutation data matrix, a break penalty of 6 and 100 random runs.

Cloned IL-12 receptor cDNAs were expressed in COS cells using either the DEAE dextran transfection or electropotation techniques (Molecular Cloning Manual). Binding assays with labeled IL-12 or labeled 2-4E6 antibody were run as described hereinabove under anti human IL-12 receptor antibody. The binding data were analyzed and Kd values were calculated according to Scatchard, using the LIGAND program discussed hereinabove under anti human IL-12 receptor antibody. In vivo labeling (6 hours) of COS cells ($3\times10^5$ cells per 35 mm diameter tissue culture dish) with $^{35}S$ Cysteine was performed 3 days after transfection as described (Molecular Cloning Manual). Cells were washed in PBS and lysed in CHAPS lysis buffer (10 mM CHAPS– 300 mM NaCl–50 mM Tris-HCl pH 7.4–2 mg/ml Iodoacetamide–0.17 mg/ml PMSF), precleared by incubation with protein G Sepharose beads (50 μl packed beads per ml, Genex) and normal mouse serum (25% final concentration) at 4° C. overnight. The beads were spun out and labeled IL-12 receptor was specifically immunoprecipitated from the cleared lysates by adding 5 μg of 2-4E6 antibody per ml of sample. The antibody was diluted in PBS containing 1% bovine serum albumin and had been loaded onto 50 μl of packed beads for 2–3 hours at 4° C. Immunoprecipitation took place overnight at 4° C. The next day, the beads were washed 3–4 times in CHAPS lysis buffer before analysis on SDS-polyacrylamide gels as described (Molecular Cloning Manual).

Lymphocyte proliferation assay

Lymphocyte proliferation assays to assess the ability of rat antisera to block cytokine-induced proliferation were performed as previously described (M. K. Gately, et al., 1992, Current Protocols in Immunology, vol. 1., J. E. Coligan, et al., eds., John Wiley & Sons, New York, N.Y., p. 6.16.1) with the following modifications. Aliquots of human PHA-activated PBMC ($2\times10^4$ per well) and of diluted rat sera were mixed in the wells of a 96-well plate and incubated at 37° C. for 30 min. The cytokines (IL-12, IL-2 or IL-7) were then added to the wells, and the cultures were incubated for 48 h at 37° C. Following this, $^3H$-TdR was added to each well, and the cultures were harvested after an additional 7 h at 37° C. All values are the means of triplicates.

Flow cytometry

The titers of anti-COS cell antibodies in the various rat antisera were assessed by flow cytometry as follows. Untransfected COS cells ($10^6$ cells/0.1 ml of Dulbecco's PBS containing 2% heat-inactivated FCS and 01% sodium azide) were preincubated with 400 μg/ml normal rat IgG (Sigma, St. Louis, Mo.) for 15 min. on ice, and then with the indicated amount of rat serum for 30 min. on ice. The cells were washed and further incubated with 2 μg/ml FITC-conjugated $F(ab')_2$ mouse anti-rat IgG (Jackson ImmunoResearch Laboratories, Inc., West Grove, Pa.) for 30 min. on ice. The cells were again washed and then analyzed by flow cytometry using a FACScan (Becton-Dickinson, Mountain View, Calif.).

Figure 18A:
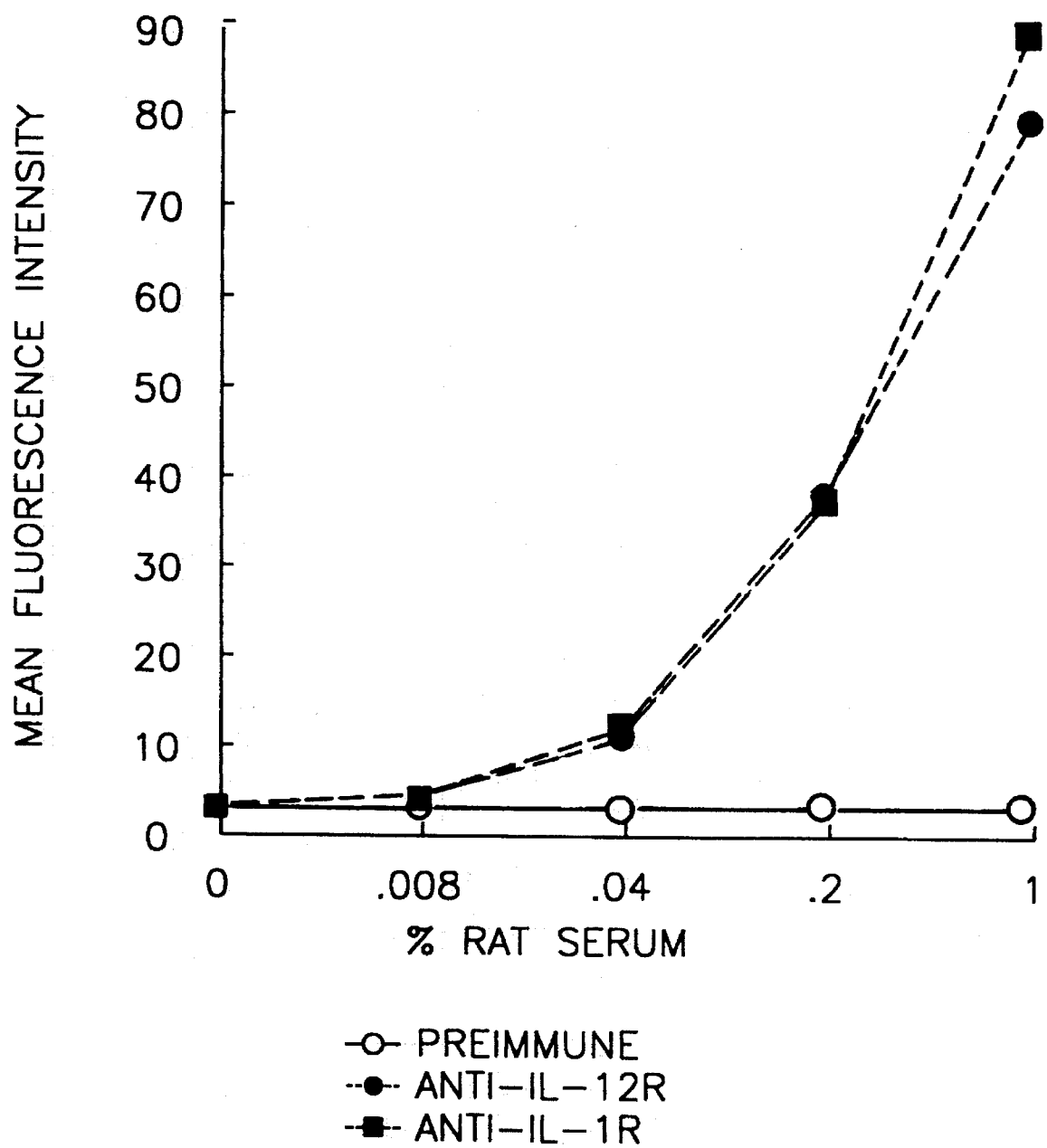
FIG. 18: Specific inhibition of IL-12-induced lymphoblast proliferation by a rat anti-IL-12R antiserum. (A) Titration by flow cytometry of anti-COS cell antibodies in an anti-IL-12R antiserum (--•---) made against 2-4E6-transfected COS cells, preimmune serum (--o--) from the rat used to prepare the anti-IL-12R antiserum, and a rat antiserum made against COS cells transfected with the human type II IL-1R (--■--). (B-D) Effects of rat sera on proliferation of PHA-activated PBMC induced by IL-12 (B), IL-2 (C), or IL-7 (D). All standard errors were <10% of the means.
Figure 18B:
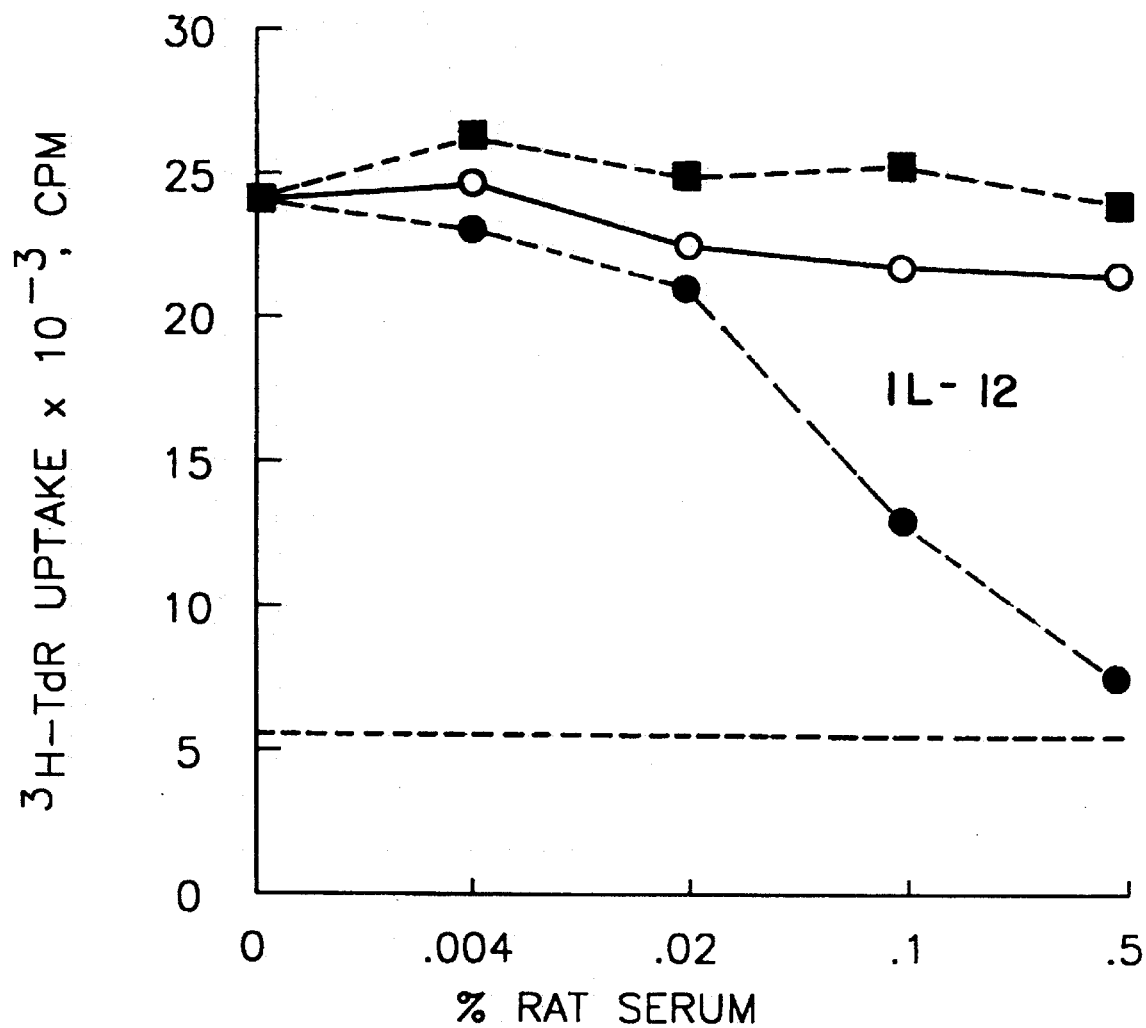
Figure 18C:
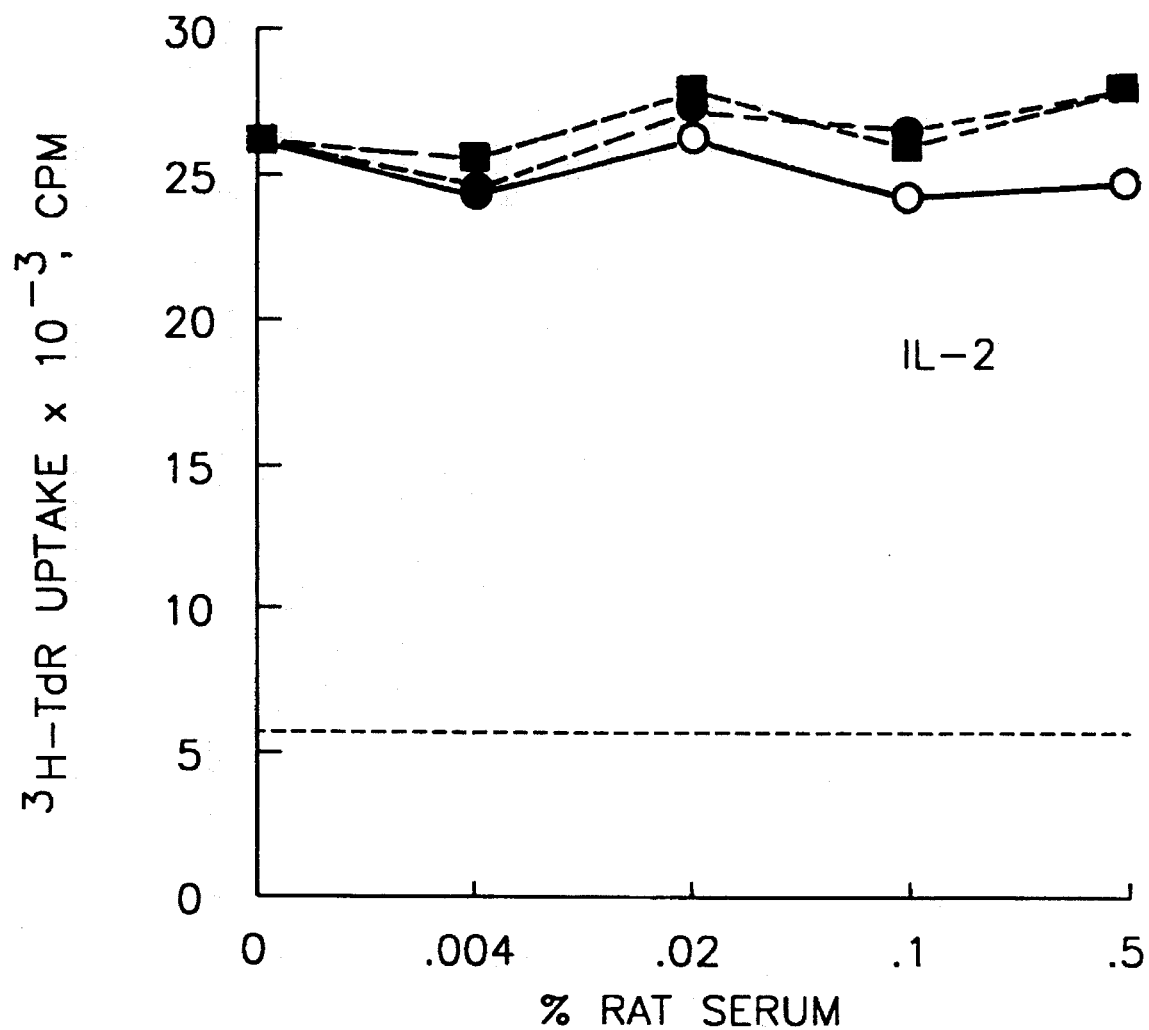
Figure 18D:
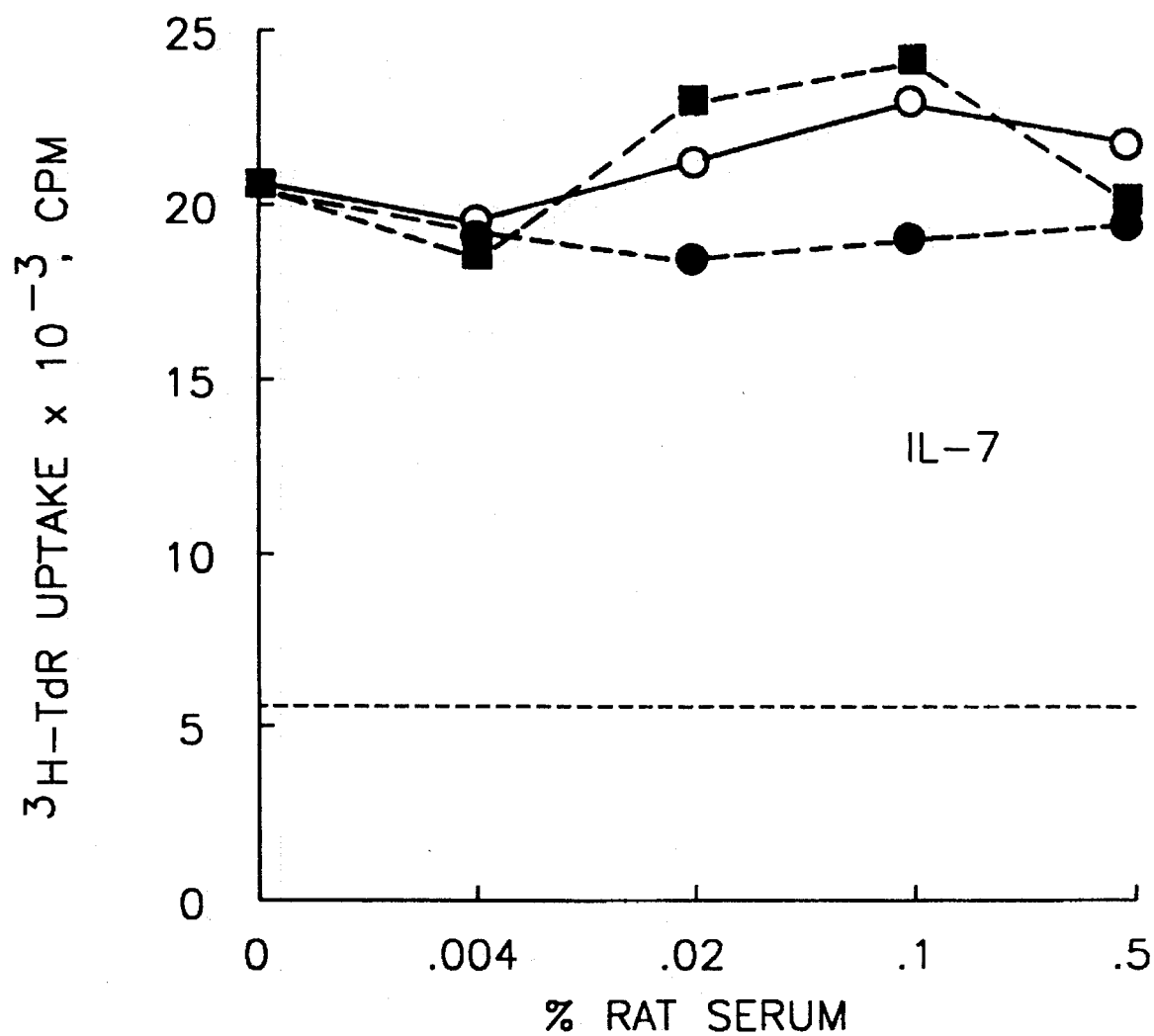

Inhibition of IL-12-induced lymphoblast proliferation by anti-IL-12R antiserum To determine whether the cloned IL-12R subunit plays an essential role in an IL-12-induced biologic response, we examined whether antiserum to the cloned IL-12R subunit could inhibit IL-12-induced proliferation of PHA-activated PBMC. This antiserum was produced by immunizing rats with 2-4E6-transfected COS cells and thus contained anti-COS cell antibodies as well as antibodies to the (putative) IL-12R subunit. For use as a control, we screened several other available rat antisera which had been prepared previously by immunization of rats with COS cells expressing proteins unrelated to the IL-12R. One such antiserum had been raised against COS cells transfected with human type II IL-1R and displayed a titer of anti-COS cell antibodies virtually identical to that of the anti-IL-12R antiserum (FIG. 18A). We then compared the effects of the anti-IL-12R antiserum, the anti-IL-1R antiserum, and preimmune serum (from the rat used to prepare the anti-IL-12R) on lymphoblast proliferation induced by IL-12, IL-2, or IL-7. The concentrations of IL-12, IL-2, and IL-7 were 0.25 ng/ml, 1.25 ng/ml, and 0.4 ng/ml, respectively. These concentrations were chosen because they resulted in similar levels of $^3$H-TdR incorporation and were on the steep portion of the dose-response curves. In this experiment, the maximum levels of $^3$H-TdR incorporation in the presence of saturating amounts of cytokine were 38,820, 111,303, and 89,541 cpm for IL-12, IL-2, and IL-7, respectively. The level of $^3$H-TdR incorporation in the absence of any added cytokine is indicated by the horizontal dotted line. Two experiments were performed with essentially identical results, and one of these is illustrated in FIGS. 18B–D. The anti-IL-12R antiserum caused dose-dependent inhibition of IL-12-induced lymphoblast proliferation but had no effect on proliferation induced by IL-2 or IL-7. In contrast, neither the preimmune serum nor the anti-IL-1R antiserum inhibited lymphoblast proliferation induced by any of the three cytokines tested. These results strongly suggest that the cloned IL-12R subunit plays an essential role in mediating IL-12-induced proliferation of PHA-activated PBMC.

Sequence Analysis of IL-12 receptor cDNA clones

The DNA sequence for the IL-12 receptor eDNA insert from clone No. 5 is shown in FIG. 1 (SEQ ID NO:1). The deduced amino acid sequence for the encoded receptor protein is shown in FIG. 2. The IL-12 receptor protein is thus composed of 662 amino acids and a calculated molecular weight of 73,112. The IL-12 receptor protein has the following features: N-terminal signal peptide, extracellular domain, transmembrane domain and cytoplasmic tail. The classical hydrophobic N-terminal signal peptide is predicted to be 20–24 amino acids in length. Signal peptide cleavage has been shown to occur mostly after the amino acids Ala, Set, Gly, Cys, Thr, Gln (G. von Heijne, Nucl. Acids Research, 1986, 14:4683). For the IL-12 receptor, the cleavage could thus take place after Gln20, Ala23 or Cys24 in the sequence shown in FIG. 2, leaving a mature protein of 638 amino acids (calculated molecular weight=70,426) based on cleavage at Cys24. The extracellular domain of the receptor is predicted to encompass the region from the C-terminus of the signal peptide to amino acid No. 540 in the sequence shown in FIG. 2. Hydrophobicity analysis shows the area from amino acid No. 541 to 571 to be hydrophobic, as would be expected for a transmembrane anchor region. Charged transfer stop residues can be found at the N- as well as the C-terminus of this predicted transmembrane area. The extracellular domain of the receptor is thus 516 amino acids long and contains all the 6 predicted N-linked glycosylation sites. The cytoplasmic portion is 91 amino acids long (amino acid residue nos. 572 to 662) and contains 3 potential phosphorylation sites (S/TXXD/E) for casein kinase II.

The cDNA library was rescreened using the insert from clone No. 5 as the probe, and a second independent cDNA was isolated (clone No. 17). This cDNA contained an additional 202 bp of 3' untranslated region. The amino acid sequence (SEQ ID NO:3) deduced from this clone for the IL-12 receptor protein was almost completely identical to the sequence shown in FIG. 2 (SEQ ID NO:2); however, a 13 bp deletion in the eDNA right before the stop codon changes the reading frame at the very C-terminus of the receptor and also gives rise to a protein that is 2 amino acids shorter (SEQ ID NO:3). Cycle sampling PCR was performed on uncloned eDNA using a pair of primers spanning the region that is expected to differ between the mRNAs representing clones 5 and 17. This analysis demonstrated that both transcripts coding for these two membrane-bound variants of the receptor subunit are present in the mRNA population isolated from PHA-activated PBMC at about equal levels (data not shown). The two transcripts are likely to arise from an alternate splicing event.

Further analysis of the amino acid sequence of the IL-12 receptor shows it to be a member of the cytokine receptor superfamily, by virtue of the sequence motifs [Cys52 - - - Cys62SW] and [W222SKWS]. Comparing the IL-12 receptor sequence to all the members of the superfamily by running the ALIGN program shows that the IL-12 receptor has the highest homology to human gp130.

Sequence analysis of the IL-12 receptor extracellular domain demonstrated the presence of the hemopoietin receptor hallmark features: two pairs of conserved cysteine-residues and the WSXWS motif. Further comparisons to the hemopoietin receptor superfamily showed the newly isolated IL-12 receptor component to be highly related to a subgroup of family members composed of gp130, G-CSF-receptor and LIF-receptor (FIG. 3); align scores were 12.37 (IL- 12R/gp130), 7.35 (IL-12R/G-CSF-R) and 6.31 (IL-12R/LIF-Rbeta). Similarities between the IL-12 receptor component and these three proteins extend beyond the hemopoietin receptor domain and include the area from the WSXWS motif to the transmembrane region (FIG. 3). The extracellular portion of gp 130 (M. Hibi et al., 1990, Cell, 63: 1149) was shown i) to contain the hemopoietin receptor superfamily domain and ii) to be also composed of 6 type III fibronectin repeats about 90 amino acids long (A. R. Kornblihtt, et al., 1985, EMBO J., 4:1755; L. Patthy, 1990, Cell, 61:13). Similarly, the extracellular domain of the IL-12 receptor can be subdivided into five such fibronectin type III repeats (residues 43–133, 143–236, 237–337, 338–444 and 445–540). The IL-12 receptor extracellular domain lacks the N-terminal Ig domain found in gp130 and therefore only accommodates 5 fibronectin type III repeats. Further sequence similarities between the IL-12 receptor, gp130, the G-CSF-receptor and the LIF-receptor can be found in the cytoplasmic regions (FIG. 3). A PXXPXP motif within a box of 8 amino acids conserved between a number of different superfamily members and a second, 12 amino acid long conserved box were found to be important for signal transduction mediated by gp130 (M. Murakami, et al., 1991, Proc. Natl. Acad. Sci. (USA), 88:11349). Both those motifs are also found in conserved areas of the cytoplasmic part of the IL-12 receptor sequence (amino acid residues 577–584 and amino acid residues 618–629).

Analysis of IL-12 Receptor mRNA Expression

Figure 6:
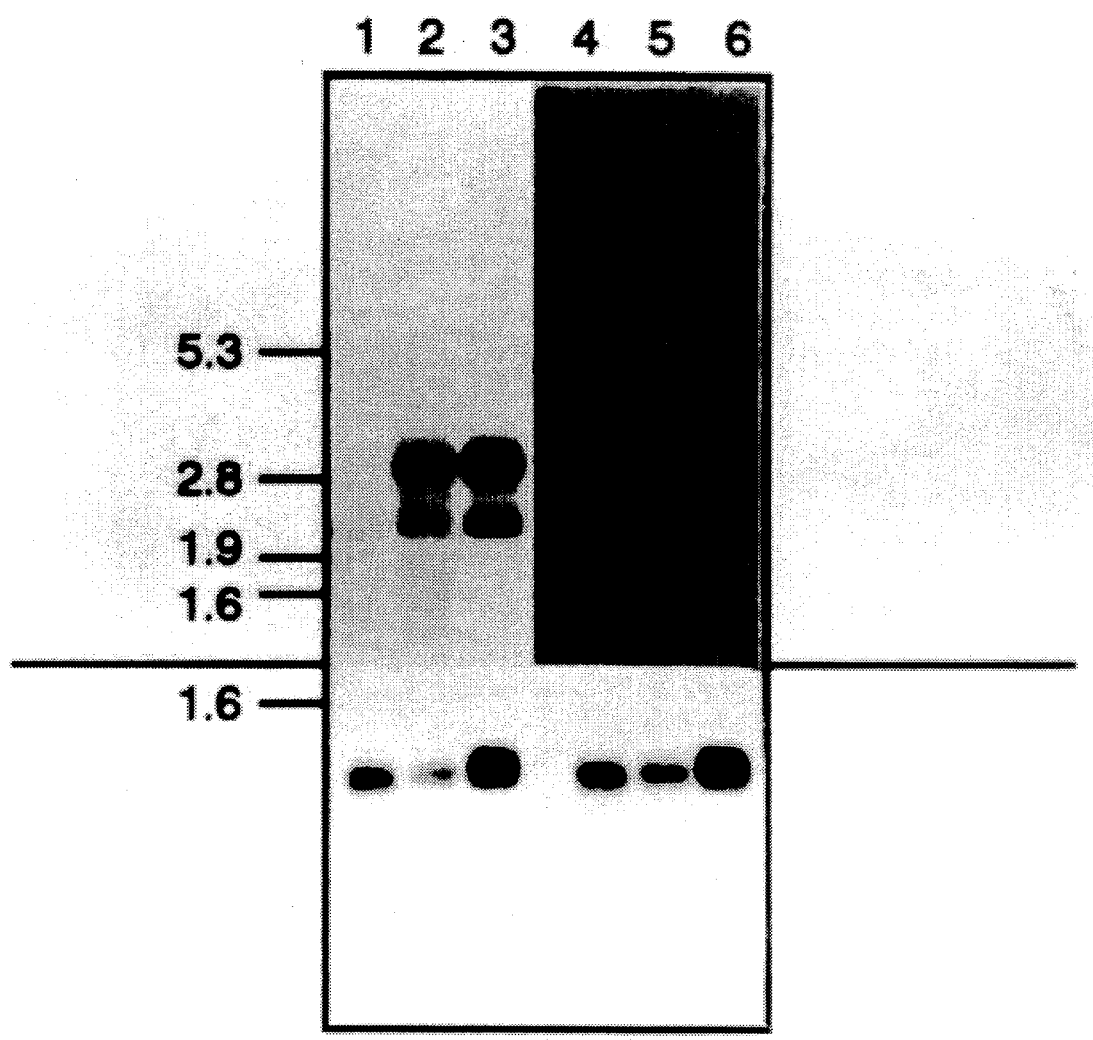
FIG. 6: RNA blot analysis. 2 μg of polyA+ RNA were run per lane. Upper panel: Lanes 1–3 were probed with a full-length receptor cDNA; lanes 4–6 were probed with the cytoplasmic portion only. Unstimulated PBMC: lanes 1,4. PHA-activated PBMC: lanes 2,5.

RNA blots were performed using poly A+ RNA from cells known to respond to IL-12: PHA-stimulated PBMC and the CD4+T-cell line Ki1225. Two RNA transcripts about 3 Kb and 2.3 Kb in size are apparent when blots are probed with the full-length cDNA (FIG. 6, lanes 1–3). Both RNAs are induced from undetectable or very low levels when PBMC are activated by PHA for 3 days (compare lanes 1 and 2); Kit225 cells express both transcripts constitutively (lane 3). Analysis by phosphoimager shows the level of the larger RNA to be about 3 to 5 fold higher than the level of the smaller RNA. Surprisingly, the smaller RNA does not hybridize to a probe derived from the cytoplasmic domain (lanes 4–6). This finding could indicate the presence of an RNA encoding i) a soluble IL-12 receptor protein, ii) a membrane bound IL-12 receptor devoid of a cytoplasmic region altogether or iii) an IL-12 receptor with a cytoplasmic sequence that is completely different from the ones present in clones 5 and 17. Elucidation of this question will have to await the isolation of a eDNA clone derived from the smaller RNA transcript.

Characterization of Recombinant IL-12 Receptor

Figure 19A:
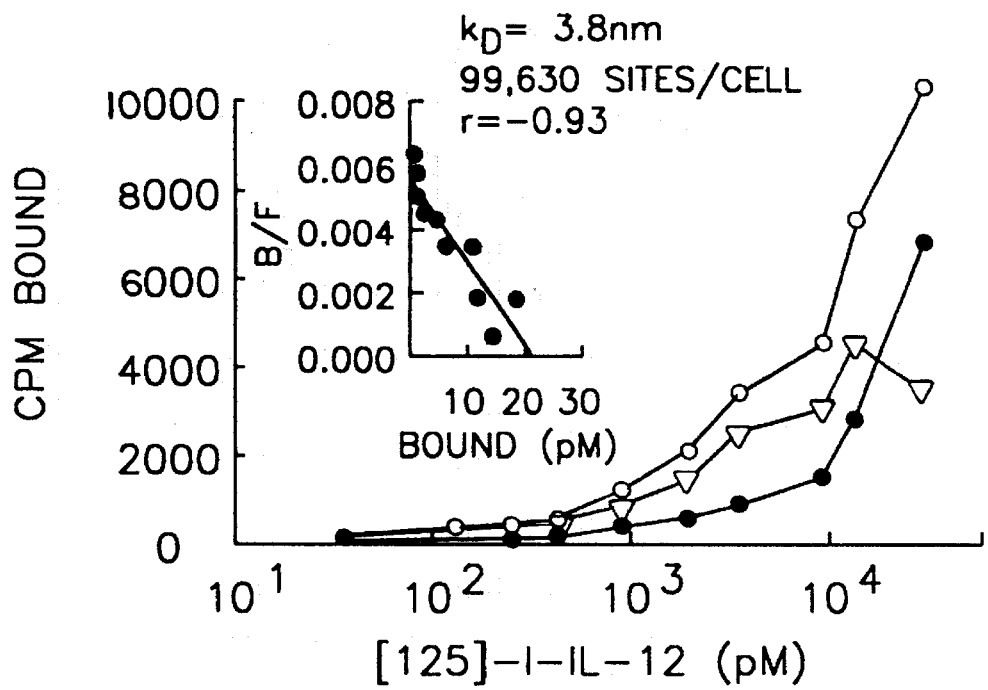
FIG. 19: Equilibrium binding of $^{125}$I-IL-12 to COS cells expressing the IL-12 receptor subunit. A) human IL-12 and B) murine IL-12. The insets show analysis of the binding data according to the method of Scatchard.
Figure 19B:
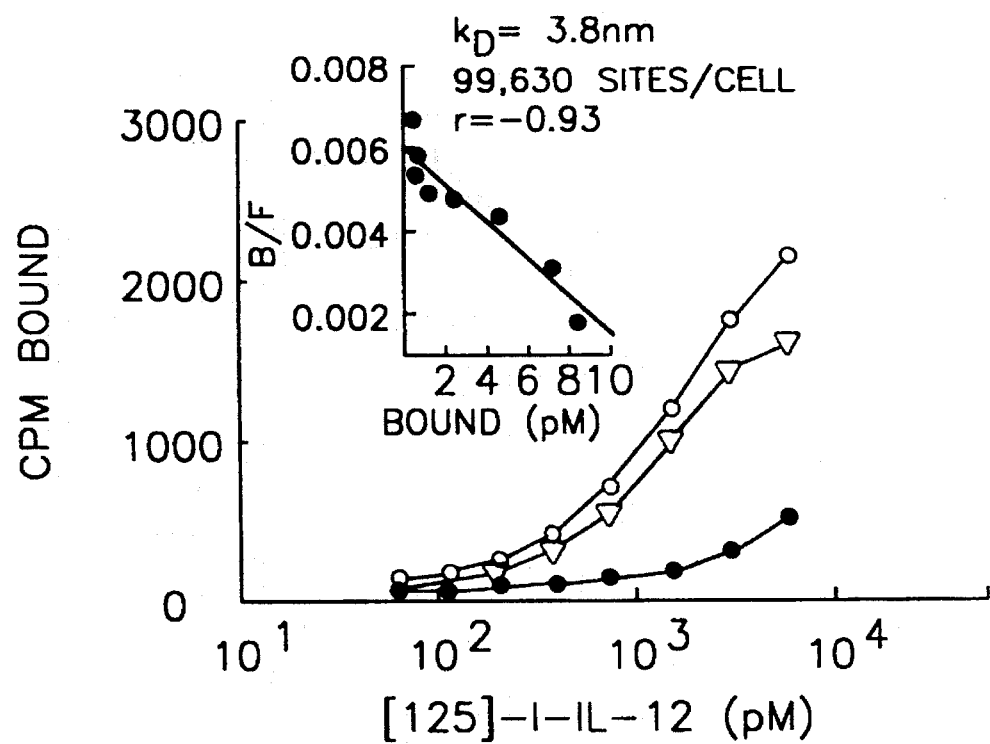

IL-12 receptor eDNA (clone number 5) (SEQ ID NO:1) was electroporated into COS cells and equilibrium binding of labeled human and murine IL-12 to the cells was performed and analyzed as described (R. Chizzonite, et al., 1992, J. Immunol., 148:3117). Results are shown in FIG. 19. Human and murine IL-12 bind to recombinant IL-12 receptor (SEQ ID NO:2) with a single affinity ($K_D$) of 3.4±1.3 nM (n=7) and 2.1±0.5 nM (n=4), respectively, which corresponds to the low affinity component of the functional IL-12 receptor on PHA-activated PB MC. After transformation by the method of Scatchard, the equilibrium binding data was best described by a single receptor site model as determined by the LIGAND program. The site numbers indicated in FIG. 19 are calculated assuming that all cells are expressing receptors. IL-12 receptor protein expressed by clone number 17 (SEQ ID NO:3) gave similar results in these binding assays. SEQ ID NO:3 would also have the same regions as SEQ ID NO:2.

Figure 5:
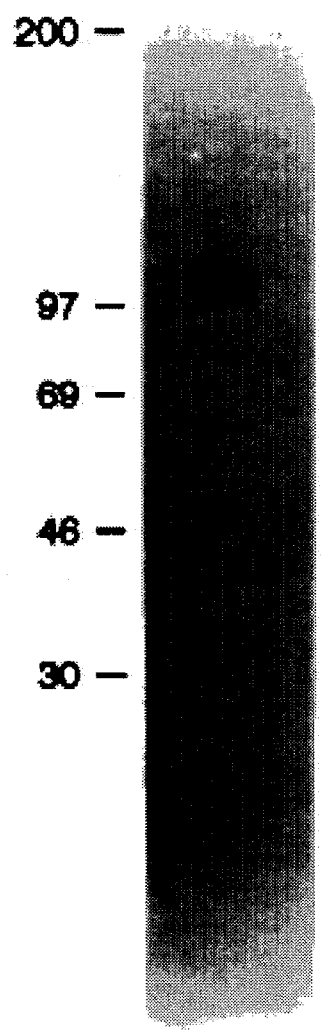
FIG. 5: Analysis of the size of human recombinant IL-12 receptor expressed in COS cells. COS cells transfected with human IL-12 receptor cDNA were labeled and lysed as described herein. Human IL-12 receptor protein was immunoprecipitated and the products were analyzed on a 4–20% gradient gel under reducing conditions. 5 μg of each listed antibody were used. They were Control $IgG_3$=isotype-matched negative control antibody; 2-4E6=anti-human IL-12 receptor antibody; 4D6=anti human IL-12 negative control antibody. Sizes of marker proteins are indicated in KDa on left.
Figure 17:
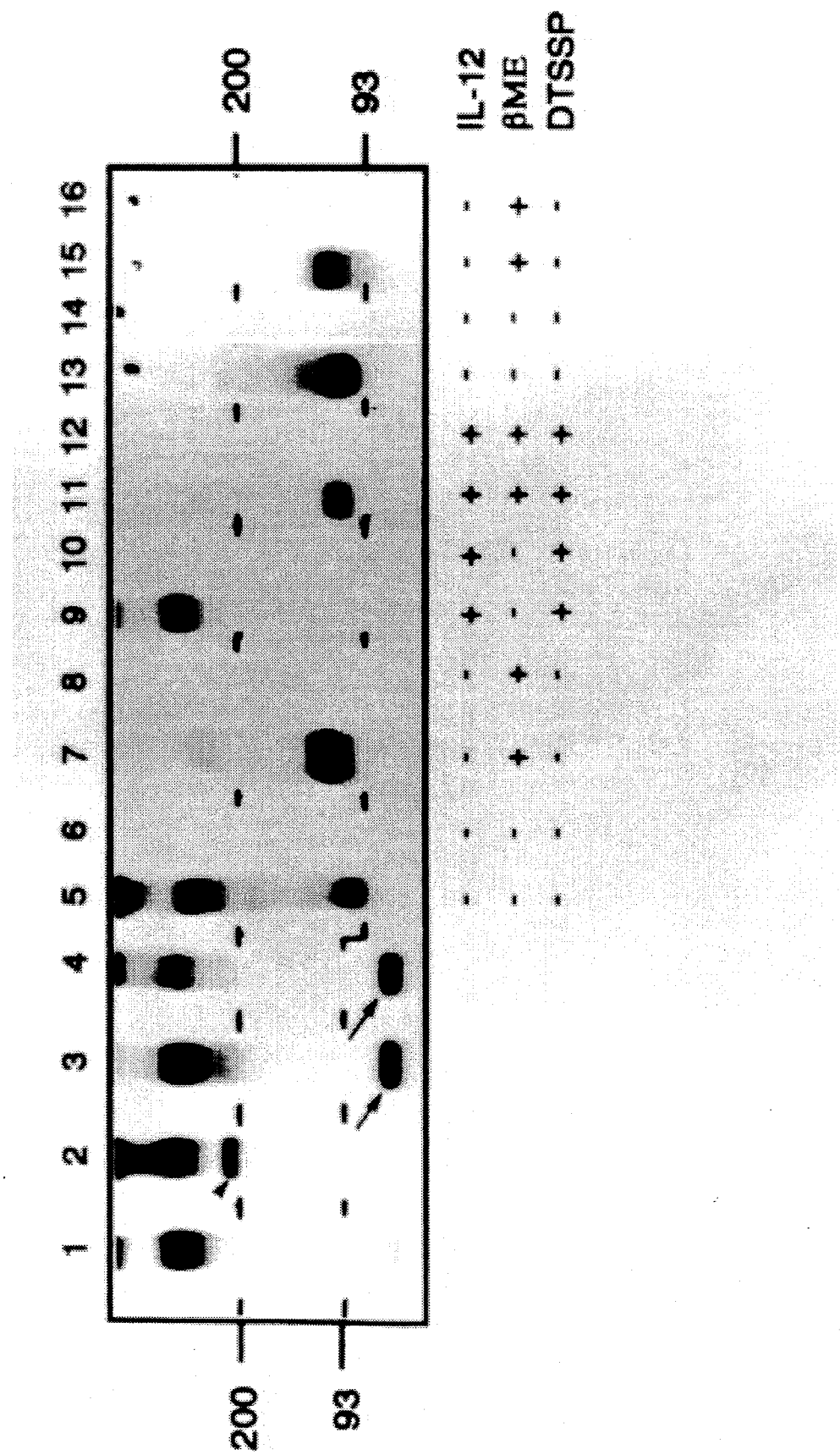
FIG. 17: Size of the IL-12 receptor subunit on the surface of transfected COS and CTLL cells. 8% gels were used and marker sizes in KDa are indicated. Lanes 1–4: Analysis of affinity crosslinked complexes under non-reducing conditions. Arrowhead=labeled, uncrosslinked 2- 4E6 antibody. Arrows=labeled, uncrosslinked IL-12. Lanes 5–12: Analysis of $^{125}$I-COS Cell Surface Proteins. Sample reduction, binding of 25 nM unlabeled IL-12 to the cells prior to analysis and use of 1 mM DTSSP crosslinker are indicated below the lanes. Lanes 13–16: Analysis of $^{125}$I-CTLL cell surface proteins.

Metabolic labeling and immunoprecipitation of the IL-12 receptor subunit expressed in COS cells indicated its size to be about 100 KDa as determined by gel analysis under reducing conditions (FIG. 5). To analyze the size of the receptor at the cell surface, affinity crosslinking studies were performed. Unless otherwise stated, characterization of the IL-12 receptor protein was done on SEQ ID NO:2. Crosslinking of 0.2 nM $^{125}$I-labeled IL-12 to either transfected COS cells, PHA-activated PBMC or K6 cells gave rise to complexes that migrate at >200 KDa (FIG. 17, lanes 1,3 and 4; arrow indicates uncrosslinked IL-12). Crosslinking at 2 nM $^{125}$I-IL-12 (a concentration equivalent to the KD) gave identical results (not shown). The size of a complex composed of one receptor subunit and one IL-12 ligand is expected to be about 175 KDa. However, FIG. 17 shows that the 175 KDa complex is present only at very low levels, if at all. Since the 150 kDA Ig and the 200 KDa markers are not separated on the gel system used, the 175 KDa IL-12/IL-12 receptor complex is expected to comigrate with them. For comparison, lane 2 shows transfected COS cells crosslinked to labeled 2-4E6 antibody (arrowhead=uncrosslinked 2-4E6). Crosslinking labeled IL-12 to i) cells that do not bind IL-12 (e.g. Raji cells), ii) mocktransfected COS cells or iii) transfected COS cells in the presence of an excess of cold IL-12 did not yield any products (not shown). For FIG. 17, labeled IL-12 (0.2 nM) was bound and crosslinked with BS3 (0.4 mM) to transfected COS cells (lane 1), PHA-activated PBMC (lane 3) or K6 cells (lane 4). Labeled 2-4E6 antibody (0.5 nM) was bound and crosslinked with BS3 (0.4 mM) to transfected COS cells (lane 2). Anti-IL-12 receptor antibody 2-4E6 (lanes 5,7), anti-ILl2 antibody 4D6 (lanes 9,11) and control antibody (lanes 6,8,10,12,) were used. Antibody 2-4E6 (lanes 13,15) and control antibody (lanes 14,16) were used.

Since crosslinking of labeled IL-12 to IL-12 receptor gave rise to products that are larger than what is expected for a complex of one receptor and one IL-12 ligand but whose size is difficult to estimate, cell surface labeling and immunoprecipitation experiments of transfected COS cells were performed. Samples were analyzed under reducing and nonreducing conditions (FIG. 17, lanes 5–12). The results can be summarized as follows: i) transfected COS cells express the IL-12 receptor subunit both as monomers and as a second, larger product that could be dimers or oligomers. Both these products are present at about equal levels (lane 5); ii) the dimerization/oligomerization does not depend on IL-12 binding. If IL-12 is prebound to the cells, the resulting banding pattern does not change (not shown); and iii) The dimers/oligomers can be converted to the monomers by reduction and must therefore be disulfide-bonded (lane 7). The data from the crosslinking and surface labeling experiments thus suggested that only the dimeric/oligomeric receptor subunit form binds IL-12 with the 3 nM affinity measured on transfected COS cells. This possibility was further investigated as follows. Complexes produced by binding unlabeled IL-12 to $^{125}$I-surface labeled COS cells and crosslinking with a cleavable crosslinker were immunoprecipitated by an anti-IL-12 antibody and analyzed under non-reducing and reducing conditions (FIG. 17, lanes 9–12). The anti-IL-12 antibody only precipitated a complex corresponding to IL-12 bound to the dimer/oligomer but not the monomer of the IL-12 receptor subunit (lane 9). Analysis of this complex under reducing conditions identified a labeled protein that comigrated with the IL-12 receptor monomer (lane 11). Experiments with a murine CTLL cell transfectant stably expressing the IL-12 receptor subunit lend further support to our findings. These cells express about 3000 to 5000 receptor subunits per cell, as measured by 2-4E6 antibody binding; however, the cells bind IL-12 very inefficiently, with an estimated Kd of 50 nM or greater (not shown). The results from surface labeling and immunoprecipitation experiments with the CTLL transfectants clearly indicate that they only express IL-12 receptor subunit monomers (FIG. 17, lanes 13–16). Taken together, the data support the hypothesis that only the receptor subunit dimers/oligomers bind IL-12 with the low affinity (3 nM) measured on transfected COS cells.

Discussion

We report here the isolation of a cDNA (clone no. 5; SEQ ID NO:1) coding for a type I transmembrane protein that represents a low affinity component of the functional IL-12 receptor (SEQ ID NO:2) found on PHA-activated PBMC. Several lines of evidence are available to support this claim. i) When transfected into COS cells, the cDNA confers specific IL-12 binding to the cells. ii) The affinity of this receptorligand interaction is about 3 nM, which corresponds to the low affinity IL-12 receptor component observed on PHA blasts. iii) The recombinant IL-12 receptor component expressed in COS cells binds both human and murine IL-12 ligands with comparable affinity. This is expected, since it was shown that similar concentrations of human and murine IL-12 transduce a signal through the human IL-12 receptor (D. S. Schoenhaut, et al., 1992, J. Immunol., 148:3433). iv) The 2-4E6 antibody recognizes both the recombinant receptor component expressed in COS cells and a component of the IL-12 receptor expressed on PHA-activated PBMC and K6 cells. 2-4E6 immunoprecipitates the complex of $^{125}$I-IL-12 affinity crosslinked to the functional IL-12 receptor on activated PBMC and K6 cells. v) Polyclonal antiserum from a rat immunized with whole COS cells transfected with the IL-12 receptor subunit inhibits proliferation of PHA-activated PBMC induced by IL-12, but not IL-2 or IL-7 induced proliferation. Whether it also plays an essential role in other IL-12-induced responses, such as IFN-gamma production by resting PBMC or NK cell activation, remains to be determined. Dual label flow cytometry has shown that the IL-12 receptor subunit is upregulated on NK-cells cultured with IL-2, consistent with our previous observations that IL-2 caused upregulation of IL-12 receptors on NK-cells (B. B. Desai, et al., 1992, J. Immunol., 148:3125). No neutralizing monoclonal antibodies to the IL-12 receptor subunit are currently available.

The size of the IL-12 receptor subunit at the cell surface was estimated by affinity crosslinking of labeled IL-12 as well as cellsurface labeling studies. Transfected COS cells express the IL-12 receptor subunit as a protein of about 100 KDa size. The calculated molecular weight for the mature form of the protein is 70,426; thus, about 25% of the molecular weight of the surface expressed protein is likely to be carbohydrate. Transfected COS cells also express a larger molecular weight form of the IL-12 receptor subunit. Our present working hypothesis, but to which we do not wish to be bound, is that this form is a disulfide-bonded dimer or oligomer of the receptor subunit. In our hands, none of the available gel systems allows the reliable separation of proteins with sizes over 150 KDa. Thus, the exact size of the receptor complexes formed is not known at this time.

The available evidence supports the conclusion that the IL-12 receptor dimerization/oligomerization is independent of IL-12 binding. Similar to these findings, it has been reported for the EPO receptor that disulfide-bonded receptor dimers and oligomers are formed and that EPO stimulation had no detectable effect on receptor dimerization (0. Miura, et al., 1993, Archives Biochem. Biophys., 306:200). Our data also indicate that only the IL-12 receptor dimers/oligomers bind IL-12 with the 2–5 nM affinity observed on intact transfected COS cells. i) An anti-IL-12 antibody only immunoprecipitates an affinity crosslinked complex corresponding to one IL-12 and a receptor dimer/oligomer. ii) Affinity crosslinked complexes of the size expected for one receptor subunit and one IL-12 are formed very inefficiently at IL-12 concentrations corresponding to the $K_D$ measured on transfected COS cells. iii) Murine CTLL cells stably expressing the receptor subunit bind IL-12 very inefficiently (estimated $K_D$=50 nM or lower); these cells also do not express subunit dimers/oligomers. It was unexpected to find that COS cells and CTLL cells differ in their ability to express the IL-12 receptor subunit in a way that allows IL-12 binding. This could be due to species specificity: murine CTLL cells are somehow unable to "process" the human IL-12 receptor protein correctly, resulting in inefficient dimerization/oligomerization and IL-12 binding. Conceivably, COS cells could express an endogenous protein that allows the IL-12 receptor dimerization/oligomerization to occur. Since under the experimental conditions used, the number of low-affinity IL-12 receptor sites per transfected COS cell is always greater than $10^5$, it seems unlikely that an endogenous COS cell component forms dimers or oligomers with the receptor subunit, although this possibility cannot be completely ruled out. Further studies will be required to evaluate these possibilities.

The IL-12 receptor subunit that we have isolated is a member of the hemopoietin receptor superfamily. Within that family, it is most closely related over its entire length to gp130 and the receptors for GCSF and LIF. The extracellular portion of the IL-12 receptor subunit can also be divided into five fibronectin type III repeats, similar to what was reported for gp130 (M. Hibi, et al., 1990, Cell, 63:1149). It is interesting to note that the ligands for IL-12 receptor and gp130, i.e. IL-12 p40 and IL-6 receptor, both also contain such fibronectin type III repeats (M. Hibi, et al., 1990, Cell, 63:1149; D. S. Schoenhaut, et al., 1992, J. Immunol., 148:3433). Some features of the cytoplasmic portion of the IL-12 receptor subunit merit further comment. Compared to the corresponding areas in gp130 (276 AA) and the receptor for LIF (237 AA), it is rather short. However, mutagenesis studies have shown that for gp130, only about 100 amino acids in the cytoplasmic region are sufficient to transduce a signal (M. Murakami, et al., 1991, Proc. Natl. Acad. Sci. (USA), 88:11349). The potential functionality of the IL-12 receptor cytoplasmic portion appears to be borne out further by the presence of a number of features conserved in other functional hemopoietic receptors (among them the receptors for G-CSF, EPO and GM-CSF): conserved areas 1 and 2 (M. Murakami, et al., 1991, Proc. Natl. Acad. Sci. (USA), 88:11349) are clearly present and thus give the low affinity IL-12 receptor component the makeup of a beta type subunit (N. Stahl, et al., 1993, Cell, 74:587).

Some reports in the past have drawn analogies between the IL-6 and IL-12 systems. Because homologies exist between i) the IL-12 p35 subunit and IL-6 (D. M. Merberg, et al., 1991, Immunology Today, 13:78) and ii) the IL-12 p40 subunit and the extracellular domain of the IL-6 receptor, IL-12 has been viewed as a complex between a soluble receptor (p40) and a cytokine (p35) (D. P. Gearing, et al., 1991, Cell, 66:9). It was predicted that the IL-12 receptor would be homologous to gp130 (D. Cosman, 1993, Cytokine, 5:95). Our results clearly support this prediction; however, they also demonstrate differences between the IL-6/soluble IL-6 receptor/gp130 system and the IL-12/IL-12 receptor system. Expression of gp130 occurs in a wide variety of cells and in an almost constitutive fashion (T. Taga, et al., 1992, FASEB J., 6:3387); the IL-12 receptor subunit and its mRNA are highly inducible in PBMC. Gp130 acts as an affinity converter for the IL-6/IL-6 receptor interaction (T. Taga, et al., 1992, FASEB J., 6:3387); the IL-12 receptor subunit simply binds IL-12 heterodimer composed of covalently bound p35 and p40 chains with low affinity. Upon binding of IL-6/soluble IL- 6R, gp130 dimerizes and a signal is transduced (M. Murakami, et al., 1993, Science, 260:1808); IL-12 receptor dimerization/oligomerization appears to be ligand independent, and a further receptor subunit is likely to be required to yield a high-affinity, functional IL-12 receptor. In that context, it is interesting to note that a previous analysis of the IL-12 receptor on PHA blasts identified an IL-12 binding protein of about 110 KDa and a receptor associated protein of about 85 KDa (R. Chizzonite, et al., 1992, J. Immunol.,148:3117). It is possible that the 110 KDa protein represents the subunit whose structure is reported here. It will be interesting to characterize the additional IL-12 receptor component and evaluate its effects on IL-12 binding and signal transduction.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

---

We claim:

1. A substantially pure, homogenous and isolated DNA encoding a human low affinity Interleukin-12 receptor protein comprising an amino acid sequence selected from SEQ ID NO:2 or SEQ ID NO:3, and which binds specifically to Interleukin-12.

2. The DNA of claim 1 which encodes an Interleukin-12 receptor protein exhibiting Interleukin-12 binding activity, said protein having the amino acid sequence SEQ ID NO:2.

3. The DNA of claim 1 which encodes an Interleukin-12 receptor protein exhibiting Interleukin-12 binding activity, said protein having the amino acid sequence SEQ ID NO:3.

4. A recombinant expression vector comprising a substantially pure, homogenous and isolated DNA encoding a human low affinity Interleukin-12 receptor protein comprising an amino acid sequence selected from SEQ ID NO:2 or SEQ ID NO:3, and which binds specifically to Interleukin-12.

5. The recombinant expression vector of claim 4 wherein the DNA encodesanInterleukin- 12 receptor protein exhibiting Interleukin-12 binding activity, said protein having the amino acid sequence SEQ ID NO:2.

6. The recombinant expression vector of claim 4 wherein the DNA encodes an Interleukin- 12 receptor protein exhibiting Interleukin-12 binding activity, said protein having the amino acid sequence SEQ ID NO:3.

7. A host cell which has been transformed by a recombinant expression vector comprising a substantially pure, homogenous and isolated DNA encoding a human low affinity Interleukin-12 receptor protein comprising an amino acid sequence selected from SEQ ID NO:2 or SEQ ID NO:3, and which binds specifically to Interleukin-12.

8. The host cell of claim 7 wherein the DNA encodes an Interleukin-12 receptor protein exhibiting Interleukin-12 binding activity, said protein having the amino acid sequence SEQ ID NO:2.

9. The host cell of claim 7 wherein the DNA encodes an Interleukin- 12 receptor protein exhibiting Interleukin-12 binding activity, said protein having the amino acid sequence SEQ ID NO:3.

10. The host cell of claim 7 which is a mammalian cell.

* * * * *